US010894786B2

(12) United States Patent
Poddutoori et al.

(10) Patent No.: US 10,894,786 B2
(45) Date of Patent: Jan. 19, 2021

(54) SUBSTITUTED PYRAZOLE DERIVATIVES AS SELECTIVE CDK12/13 INHIBITORS

(71) Applicant: Aurigene Discovery Technologies Limited, Bangalore (IN)

(72) Inventors: Ramulu Poddutoori, Telangana (IN); Susanta Samajdar, Bangalore (IN); Subhendu Mukherjee, Hooghly (IN)

(73) Assignee: Aurigene Discovery Technologies Limited, Bangalore (IN)

( * ) Notice: Subject to any disclaimer, the term of this patent is extended or adjusted under 35 U.S.C. 154(b) by 0 days.

(21) Appl. No.: 16/374,842

(22) Filed: Apr. 4, 2019

(65) Prior Publication Data

US 2019/0308951 A1    Oct. 10, 2019
US 2020/0308142 A9    Oct. 1, 2020

(30) Foreign Application Priority Data

Apr. 4, 2018   (IN) .............................. 201841012850

(51) Int. Cl.

| | |
|---|---|
| *A61K 31/4439* | (2006.01) |
| *C07D 401/12* | (2006.01) |
| *C07D 401/14* | (2006.01) |
| *A61P 35/00* | (2006.01) |
| *C07D 403/12* | (2006.01) |
| *C07D 413/14* | (2006.01) |
| *C07D 231/40* | (2006.01) |

(52) U.S. Cl.
CPC ............ *C07D 401/12* (2013.01); *A61P 35/00* (2018.01); *C07D 231/40* (2013.01); *C07D 401/14* (2013.01); *C07D 403/12* (2013.01); *C07D 413/14* (2013.01)

(58) Field of Classification Search
None
See application file for complete search history.

(56) References Cited

U.S. PATENT DOCUMENTS 6,218,418 B1 *  4/2001  Pevarello ............. C07D 231/16
                                              514/404

* cited by examiner

*Primary Examiner* — Samantha L Shterengarts
(74) *Attorney, Agent, or Firm* — Benjamin Aaron Adler

(57) ABSTRACT

The present invention provides substituted pyrazole derivatives of formula (I)

which are therapeutically useful as selective CDK12/13 inhibitors. These compounds are useful in the treatment and/or prevention of diseases and/or disorders associated with CDK12/13 in a mammal. The present invention also provides preparation of the compounds and pharmaceutical compositions with at least one of the substituted pyrazole derivatives of formula (I) or a pharmaceutically acceptable salt, an N-oxide or a stereoisomer thereof.

25 Claims, No Drawings

SUBSTITUTED PYRAZOLE DERIVATIVES AS SELECTIVE CDK12/13 INHIBITORS

CROSS-REFERENCE TO RELATED APPLICATIONS

This non-provisional application claims benefit under 35 U.S.C. § 119(a) of Indian provisional application number 201841012850, filed Apr. 4, 2018, the entirety of which is hereby incorporated by reference.

BACKGROUND OF THE INVENTION

Field of the Invention

This invention relates to substituted pyrazole derivatives useful for treatment of cancer and inflammatory diseases associated with CDK12/13. The invention also provides pharmaceutically acceptable compositions comprising compounds of the present invention and methods of using said compositions in the treatment of diseases associated with CDK12/13.

Description of the Related Art

Cyclin dependent kinases (CDKs) are a family of Ser/Thr kinases that integrate various signal transduction pathways and play a key role in several key cellular processes. CDK12 and its orthologue CDK13 belong to the class of 'transcriptional' CDKs. CDK12/Cyclin K regulates transcriptional elongation, pre-mRNA splicing and alternate splicing. The Cancer Genome Atlas (TCGA) project has identified CDK12 mutations in several breast and ovarian cancers, implicating its role as tumour suppressor. Mutation of CDK12 in serous ovarian carcinoma is associated with decreased expression of DNA damage response (DDR) genes such as BRCA1, FANCI, ATM, ATR or FANCD2 and increased sensitivity to PARP inhibitors. (Cancer Res, 2016, 76(7) 1182; Nucleic Acids Research, 2015, Vol. 43, 2575-2589). Hence, maintenance of genomic stability appears to be the key role of this protein.

Transcription of protein-coding genes is controlled by RNA Polymerase II. Phosphorylation of residues in its C-terminal domain (CTD) orchestrate the production of mature mRNA transcript. Phosphorylation of Ser2, which promotes elongation of RNA Pol II through the gene body, is a key mechanism of CDK12 transcriptional regulation (Genes & Development 2010, 24:2303-2316). As a consequence, CDK12 knockdown has also been associated with downregulation of genes involved in homologous recombination (Genes & Development 2011, 25:2158-2172). The emergence of increasingly significant role of CDK12 in genomic stability and oncogenesis provides new insight towards deciphering the function of CDK12 in genome maintenance and oncogenesis.

The frequency and distribution of CDK12 protein expression was assessed by Immuno Hito Chemistry (IHC) in independent cohorts of breast cancer and this was correlated with outcome and genomic status. It was found that 21% of primary unselected breast cancers were CDK12 high, and 10.5% were absent. CDK12 overexpression in breast cancer cells has been demonstrated to regulate splicing of pre-mRNA involved in DDR and tumorigenesis. (Nucleic Acids Res., 2017, Jun. 20; 45(11):6698-6716). Disruption of Cyclin-Dependent Kinase 12 (CDK12) is known to lead to defects in DNA repair and sensitivity to platinum salts and PARP1/2 inhibitors. Interestingly, absence of CDK12 protein was associated with reduced expression of a number of DDR proteins including ATR, Ku70/Ku80, PARP1, DNA-PK, and γH2AX, suggesting a novel mechanism of CDK12-associated DDR dysregulation in breast cancer. This may have important therapeutic implications, particularly for triple-negative breast cancers (Molecular Cancer Therapeutics (2018), 17(1), 306-315).

As transcription is a highly critical cellular process and is controlled by different transcription regulating kinases it is desirable to have as selective a compound as possible to overcome unwanted side effects. For example, CDK-7 is reported to control transcription initiation by phosphorylation of Ser5 and Ser7 residue of RNA polymerase II, whereas CDK-12 is reported to be responsible for elongation of transcription through phosphorylation of Ser2 residue of RNA polymerase II (Nucleic Acids Research, 2015, Vol. 43, No. 5, 2575-2589).

It is reported that the inhibition of both initiation and elongation at the same time modulate a much longer number of gene transcription (Popova, T. et. al. Cancer Res. 2016, 76, 1882). Consistent with this notion, the findings from a recent study in which genome-scale CRISPR-Cas9 screening across 341 cancer cell lines representing diverse cancer cell types indicated that CDK7 disruption was pan-lethal similar to the depletion seen for known essential genes in the screen, raising some concerns about the therapeutic window of a potent CDK7 inhibitor (Cancer Cell 2018, Vol. 33, 1-15). In contrast to the dependency of 100% of cancer cell lines for CDK7, CDK12 and CDK13 showed differential dependencies only in a subset of cell lines (10.2% and 3.8% respectively) included in the screen supporting the advantages of a selective CDK12/13 inhibitor in a subset of cancer indications over a CDK7 inhibitor (Cancer Cell 2018, Vol. 33, 1-15).

WO 2016/193939 discloses compounds that inhibit activity of certain transcriptional cyclin dependent kinases (CDKs) including CDK7, CDK9, CDK12, CDK13 and CDK18, with particular focus on the inhibition of transcriptional cyclin dependent kinase-7 (CDK7). The present inventors have found that the compounds disclosed in WO 2016/193939 do indeed inhibit CDK7 and CDK12/13, however, they are not selective towards CDK12/13.

There remains a need in the art to find compounds which selectively inhibit CDK12/13 over other CDKs. It is, therefore, an objective of this invention to provide compounds useful in the treatment and/or prevention or amelioration of diseases and/or disorders associated with CDK12/13.

SUMMARY OF THE INVENTION

Provided herein are substituted pyrazole derivatives and pharmaceutical compositions thereof, which are useful as selective CDK12/13 inhibitors.

In one aspect of the present invention, it comprises compounds of formula (I):

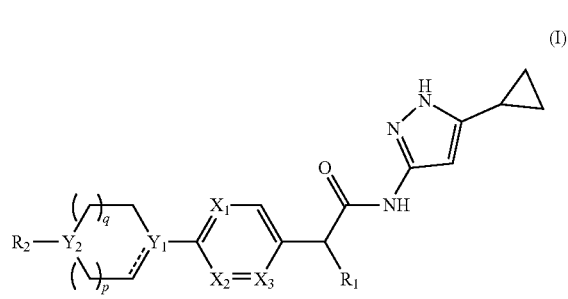

or a pharmaceutically acceptable salt, a N-oxide or a stereoisomer thereof;
wherein,
------ is an optional bond;
each $X_1$, $X_2$ and $X_3$ are independently $CR_3$ or N;
each $Y_1$ and $Y_2$ are independently C, CH or N;
$R_1$ is hydrogen or alkyl;
$R_2$ is

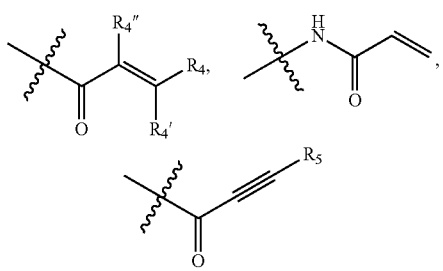

or —C≡N;
each $R_3$ is independently selected from hydrogen, halogen, cyano and alkyl;
$R_4$ is hydrogen, alkyl or —$(CH_2)_n$—$NR_aR_b$;
$R_4'$ & $R_4''$ are each independently hydrogen or alkyl;
$R_5$ is hydrogen or alkyl;
$R_a$ and $R_b$ are each independently hydrogen or alkyl; alternatively, $R_a$ and $R_b$ together with the nitrogen atom to which they are attached form an optionally substituted heterocyclic ring containing 0-2 additional heteroatoms independently selected from N, O and S;
n is 1 to 3; and
p and q are each independently selected from 0 to 2.

In yet another aspect, the present invention provides a pharmaceutical composition comprising a compound of formula (I) or a pharmaceutically acceptable salt thereof and at least one pharmaceutically acceptable excipient (such as a pharmaceutically acceptable carrier or diluent).

In yet another aspect, the present invention relates to the preparation of compounds of formula (I).

In yet another aspect of the present invention, provided herein are substituted pyrazole derivatives of formula (I), which selectively inhibit CDK12/13 and therapeutic uses thereof.

In a still further aspect, the invention provides methods of treating diseases and/or disorders or conditions mediated by CDK12/13 in a subject comprising administration of compounds of formula (I) or compositions thereof.

DETAILED DESCRIPTION OF THE INVENTION

The present invention provides substituted pyrazole derivatives of formula (I), which are useful as selective CDK12/13 inhibitors.

The present invention further provides pharmaceutical compositions comprising the said substituted pyrazole compounds of formula (I) and their derivatives as therapeutic agents.

In one embodiment, the present invention provides compounds of formula (I),

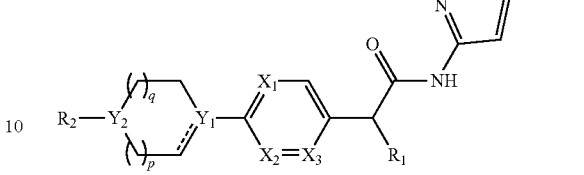

or a pharmaceutically acceptable salt, a N-oxide or a stereoisomer thereof;
wherein,
------ is an optional bond;
each $X_1$, $X_2$ and $X_3$ are independently $CR_3$ or N;
each $Y_1$ and $Y_2$ are independently C, CH or N;
$R_1$ is hydrogen or alkyl;
$R_2$ is

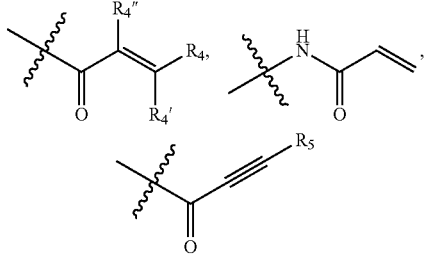

or —C≡N;
each $R_3$ is independently selected from hydrogen, halogen, cyano and alkyl;
$R_4$ is hydrogen, alkyl or —$(CH_2)_n$—$NR_aR_b$;
$R_4'$ & $R_4''$ are each independently hydrogen or alkyl;
$R_5$ is hydrogen or alkyl;
$R_a$ and $R_b$ are each independently hydrogen or alkyl; alternatively, $R_a$ and $R_b$ together with the nitrogen atom to which they are attached form an optionally substituted heterocyclic ring containing 0-2 additional heteroatoms independently selected from N, O and S;
n is 1 to 3; and
p and q are each independently selected from 0 to 2.

In another embodiment of the present invention, it provides compounds of formula (I),
wherein,
------ is an optional bond;
$X_1$ is N; $X_2$ and $X_3$ are each $CR_3$;
each $Y_1$ and $Y_2$ are independently CH or N;
$R_1$ is alkyl;
$R_2$ is

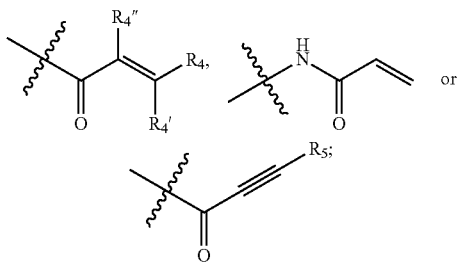

each $R_3$ independently is hydrogen or halogen; and
$R_4$, $R_4'$, $R_4''$ & $R_5$ are each independently hydrogen or alkyl.

In another embodiment of the present invention, it provides compounds of formula (I),
wherein,
------ is a bond;
$X_1$ is N; $X_2$ and $X_3$ are each $CR_3$;
$Y_1$ is C; $Y_2$ is N;
$R_1$ is hydrogen or alkyl;
$R_2$ is

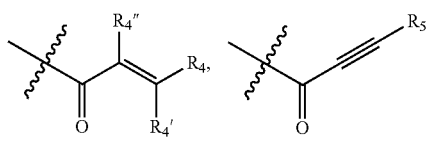

or —C≡N;
each $R_3$ independently is hydrogen or halogen; and
$R_4$, $R_4'$, $R_4''$ & $R_5$ are each independently hydrogen or alkyl.

In another embodiment of the present invention, it provides compounds of formula (I),
wherein,
------ is a bond;
$X_1$ is N; $X_2$ and $X_3$ are each $CR_3$;
$Y_1$ is C; $Y_2$ is N;
$R_1$ is hydrogen;
$R_2$ is

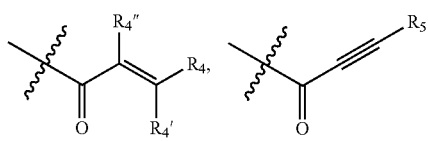

or —C≡N;
each $R_3$ independently is hydrogen or halogen; and
$R_4$, $R_4'$, $R_4''$ & $R_5$ are each independently hydrogen or alkyl.

In another embodiment of the present invention, it provides compounds of formula (I),
wherein,
------ is a bond;
$X_1$ is N; $X_2$ and $X_3$ are each $CR_3$;
each $Y_1$ and $Y_2$ are independently CH or N;
$R_1$ is alkyl;
$R_2$ is

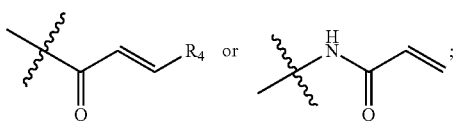

$R_3$ is hydrogen, halogen, cyano or alkyl; and
$R_4$ is hydrogen.

In another embodiment of the present invention, it provides compounds of formula (I) wherein,
------ is a bond;
each $X_1$, $X_2$ and $X_3$ are independently $CR_3$ or N;
$Y_1$ is C and $Y_2$ is N;

$R_1$ is alkyl;
$R_2$ is

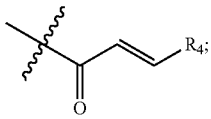

$R_3$ is hydrogen, halogen, cyano or alkyl; and
$R_4$ is hydrogen.

In another embodiment of the present invention, it provides compounds of formula (I)
wherein,

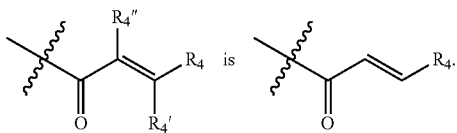

In yet another embodiment of the present invention, it provides compounds of formula (IA), (IA)

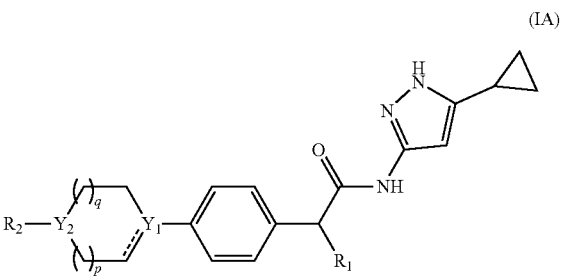

or a pharmaceutically acceptable salt thereof or a stereoisomer thereof;
wherein, $Y_1$, $Y_2$, $R_1$, $R_2$, p and q are same as defined in formula (I).

In yet another embodiment of the present invention, it provides compounds of formula (IB), (IB)

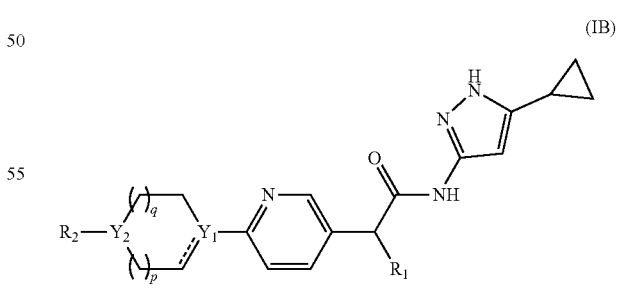

or a pharmaceutically acceptable salt, a N-oxide or a stereoisomer thereof;
wherein, $Y_1$, $Y_2$, $R_1$, $R_2$, p and q are same as defined in formula (I).

In yet another embodiment of the present invention, it provides compounds of formula (IC),

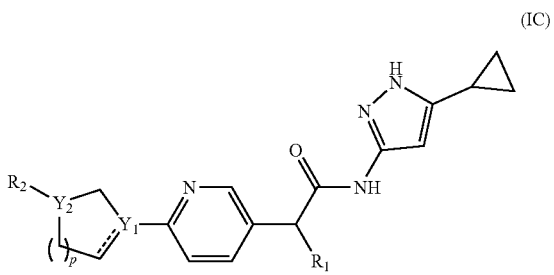
(IC)

or a pharmaceutically acceptable salt, a N-oxide or a stereoisomer thereof;

wherein, $Y_1$, $Y_2$, $R_1$, $R_2$ and p are same as defined in formula (I).

In yet another embodiment of the present invention, it provides compounds of formula (ID),

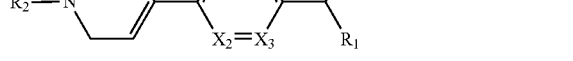
(ID)

or a pharmaceutically acceptable salt, a N-oxide or a stereoisomer thereof;

wherein, $X_1$, $X_2$, $X_3$, $R_1$ and $R_2$ are same as defined in formula (I).

In yet another embodiment of the present invention, it provides compounds of formula (IE),

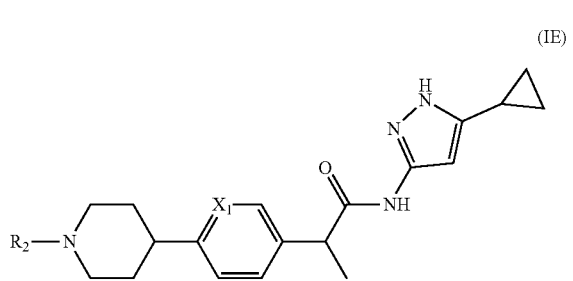
(IE)

or a pharmaceutically acceptable salt, N-oxide or a stereoisomer thereof;

wherein, $X_1$ and $R_2$ are same as defined in formula (I).

In yet another embodiment of the present invention, it provides compounds of formula (IF),

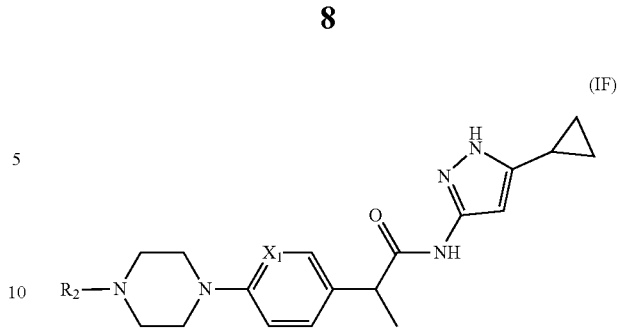
(IF)

or a pharmaceutically acceptable salt, a N-oxide or a stereoisomer thereof;

wherein, $X_1$ and $R_2$ are same as defined in formula (I).

In yet another embodiment of the present invention, it provides compounds of formula (IG),

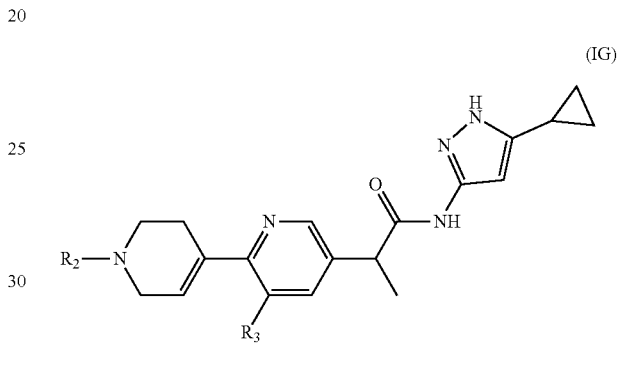
(IG)

or a pharmaceutically acceptable salt, a N-oxide or a stereoisomer thereof;

wherein, $R_2$ and $R_3$ are same as defined in formula (I).

In yet another embodiment of the present invention, it provides compounds of formula (IH),

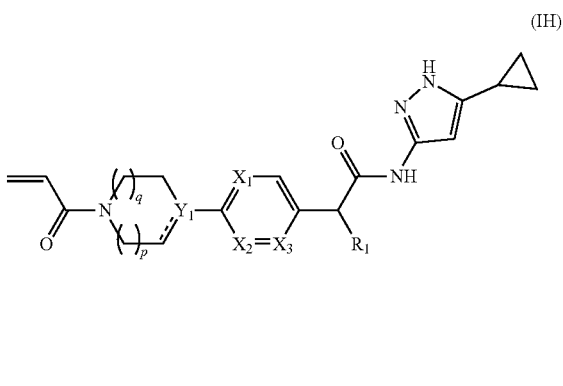
(IH)

or a pharmaceutically acceptable salt, a N-oxide or a stereoisomer thereof;

wherein, $X_1$, $X_2$, $X_3$, $Y_1$, $R_1$, p and q are same as defined in formula (I).

In yet another embodiment of the present invention, it provides compounds of formula (IJ), (IJ)

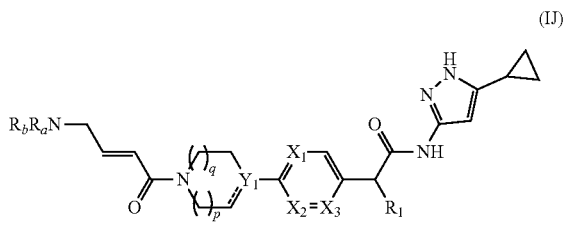

or a pharmaceutically acceptable salt, a N-oxide or a stereoisomer thereof;

wherein, $X_1$, $X_2$, $X_3$, $Y_1$, $R_1$, $R_a$, $R_b$, p and q are same as defined in formula (I).

In yet another embodiment of the present invention, it provides compounds of formula (IK), (IK)

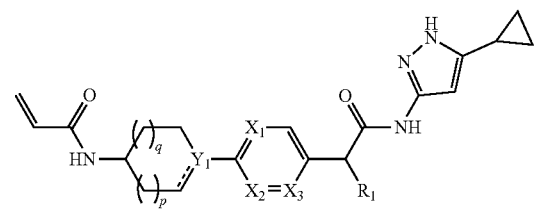

or a pharmaceutically acceptable salt, a N-oxide or a stereoisomer thereof;

wherein, $X_1$, $X_2$, $X_3$, $Y_1$, $R_1$, p and q are same as defined in formula (I).

In yet another embodiment of the present invention, it provides compounds of formula (IL), (IL)

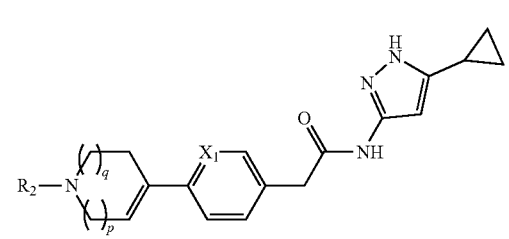

or a pharmaceutically acceptable salt thereof, a N-oxide or a stereoisomer thereof;

wherein, $X_1$, $R_2$, p and q are same as defined in formula (I).

In yet another embodiment of the present invention, it provides compounds of formula (IM), (IM)

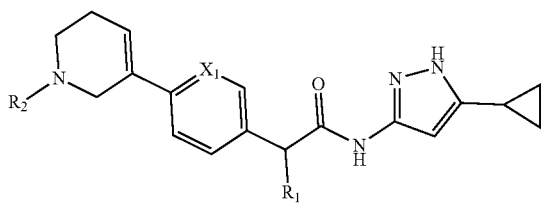

or a pharmaceutically acceptable salt thereof, a N-oxide or a stereoisomer thereof;

wherein, $X_1$, $R_1$ and $R_2$ are same as defined in formula (I).

The embodiments below are illustrative of the present invention and are not intended to limit the claims to the specific embodiments exemplified.

According to one embodiment, specifically provided are compounds of formula (I), wherein, $X_1$ is $CR_3$, $X_2$ is $CR_3$ and $X_3$ is $CR_3$; wherein the said $R_3$ at each occurrence independently is hydrogen or halogen.

According to one embodiment, specifically provided are compounds of formula (I), wherein, $X_1$ is CH, $X_2$ is N and $X_3$ is N.

According to one embodiment, specifically provided are compounds of formula (I), wherein, $X_1$ is N, $X_2$ is $CR_3$ and $X_3$ is $CR_3$; wherein the said $R_3$ at each occurrence independently is hydrogen, halogen, cyano or alkyl.

According to one embodiment, specifically provided are compounds of formula (I), wherein, $X_1$ is N, $X_2$ is N and $X_3$ is CH.

According to one embodiment, specifically provided are compounds of formula (I), wherein, $X_1$ is N, $X_2$ is CH and $X_3$ is N.

According to one embodiment, specifically provided are compounds of formula (I), wherein, ring

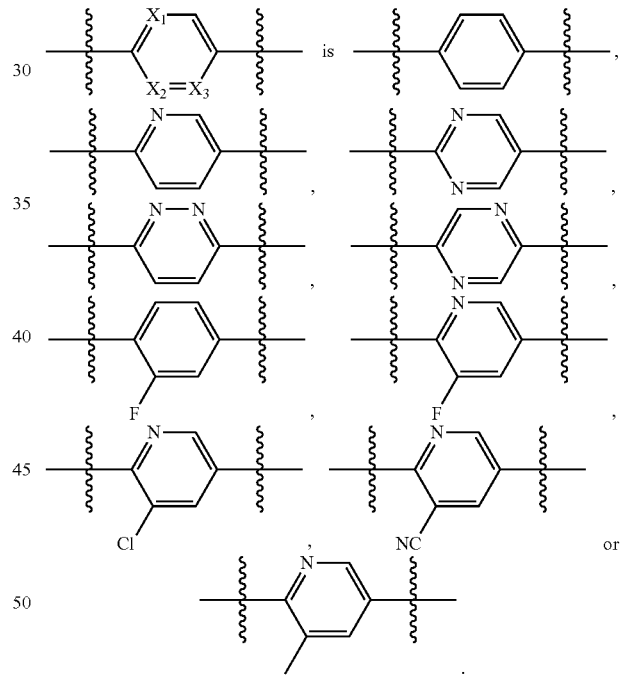

In yet another embodiment, specifically provided are compounds of formula (I), wherein the ring

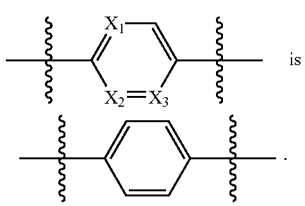

is

.

In yet another embodiment, specifically provided are compounds of formula (I), wherein the ring

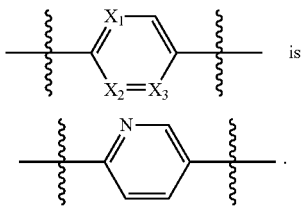 is

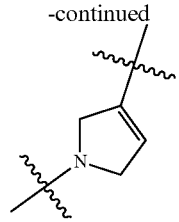.

In yet another embodiment, it provides compounds of formula (I), wherein, ring

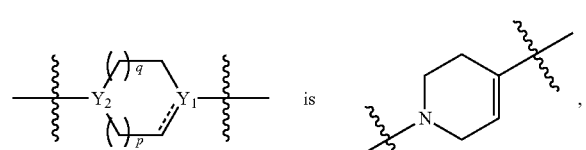 is

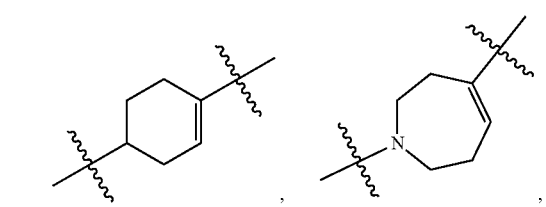,

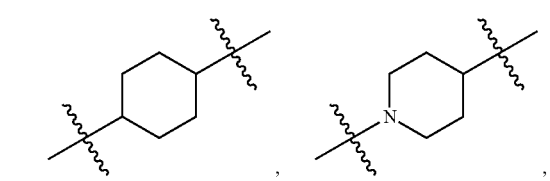,

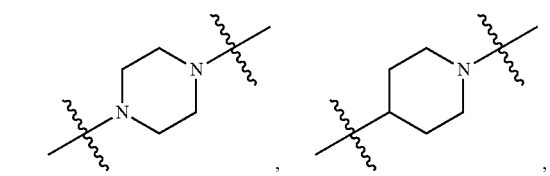,

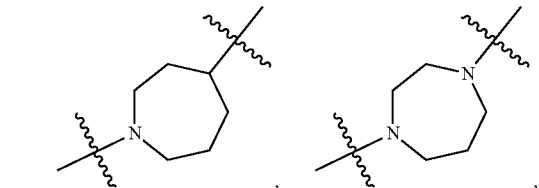,

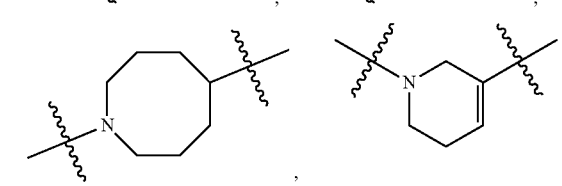,

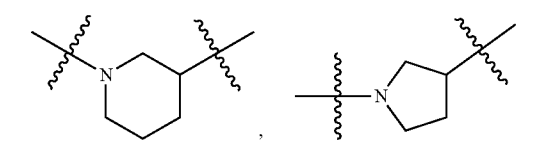

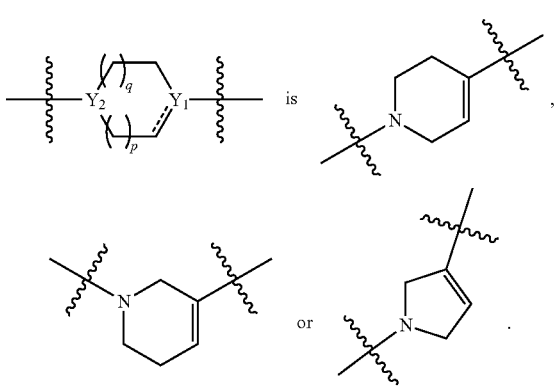

In yet another embodiment, specifically provided are compounds of formula (I), wherein, $R_1$ is alkyl; the said alkyl is methyl, ethyl or isopropyl.

In yet another embodiment, specifically provided are compounds of formula (I), wherein, $R_1$ is hydrogen.

In yet another embodiment, specifically provided are compounds of formula (I), wherein the ring

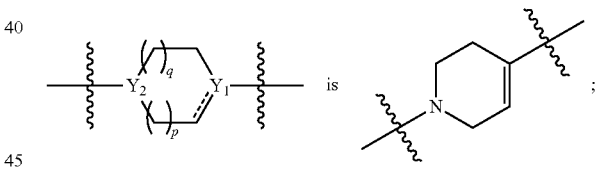;

ring

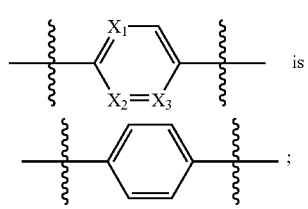;

$R_1$ is methyl; $R_2$ is

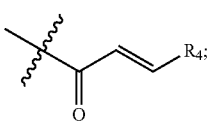

wherein the $R_4$ is hydrogen.

In yet another embodiment, specifically provided are compounds of formula (I), wherein the ring

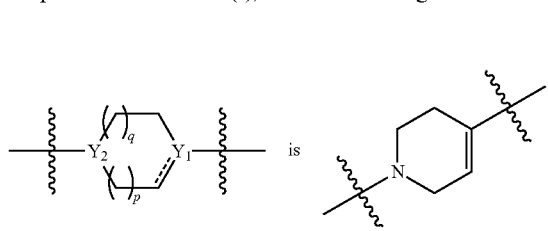 is 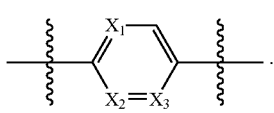

wherein * is the point of attachment with ring

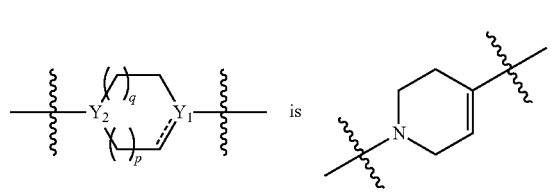.

In yet another embodiment, specifically provided are compounds of formula (I), wherein the ring

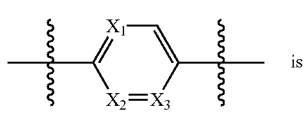 is 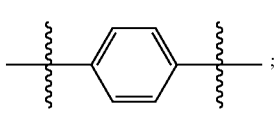 ;

ring

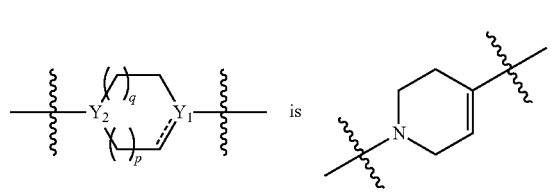 ;

$R_1$ is methyl; $R_2$ is

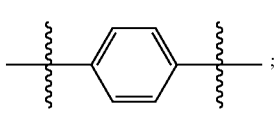 ;

$R_4$ is —$CH_2$—$NR_aR_b$; wherein $R_a$ and $R_b$ are each independently hydrogen or alkyl; alternatively, $R_a$ and $R_b$ together with the nitrogen atom to which they are attached form an optionally substituted heterocyclic ring containing 0-2 additional heteroatoms independently selected from N, O and S.

In yet another embodiment, specifically provided are compounds of formula (I), wherein the ring

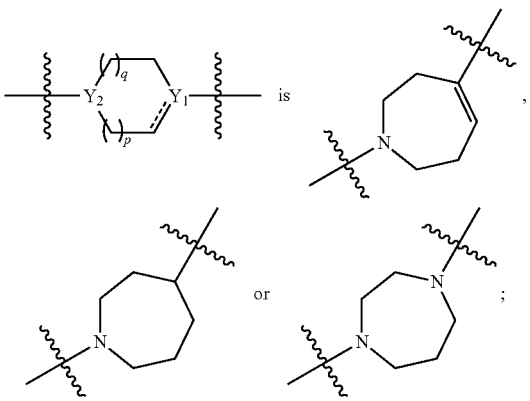

ring

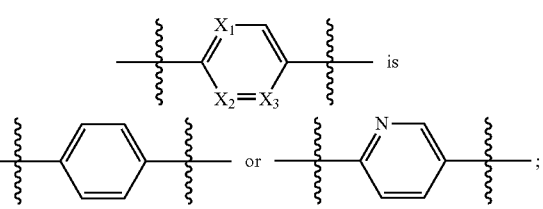

$R_1$ is methyl; $R_2$ is

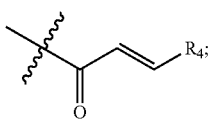

wherein the $R_4$ is hydrogen.

In yet another embodiment, specifically provided are compounds of formula (I), wherein, ring

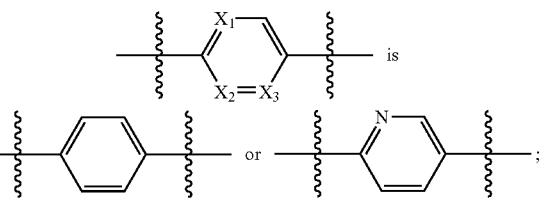

ring

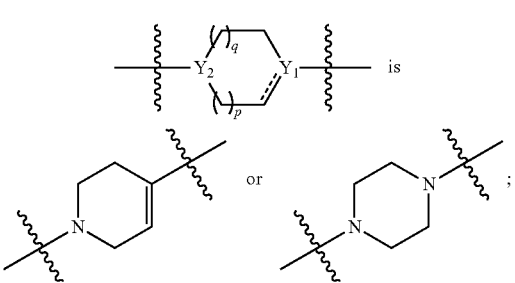

$R_1$ is methyl; $R_2$ is

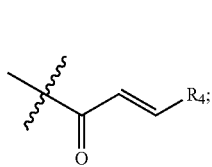

and $R_4$ is hydrogen.

In yet another embodiment, specifically provided are compounds of formula (I), wherein, ring

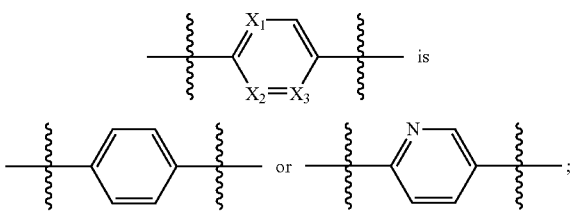

ring

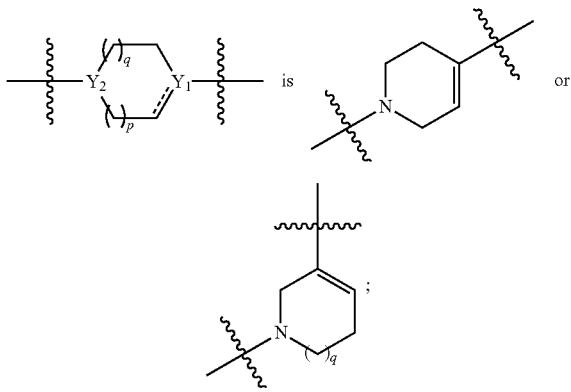

$R_1$ is hydrogen or methyl; $R_2$ is

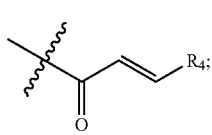

and $R_4$ is hydrogen.

In yet another embodiment, specifically provided are compounds of formula (I), wherein, ring

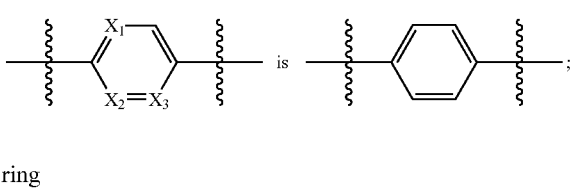

ring

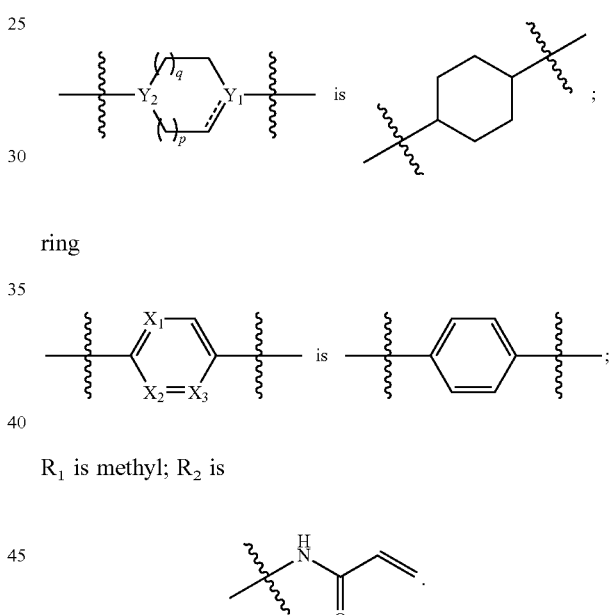

$R_1$ is methyl; and $R_2$ is wherein $R_4$ is hydrogen.

In yet another embodiment, specifically provided are compounds of formula (I), wherein, the ring ring $R_1$ is methyl; $R_2$ is In yet another embodiment, specifically provided are compounds of formula (I), wherein, $R_2$ is

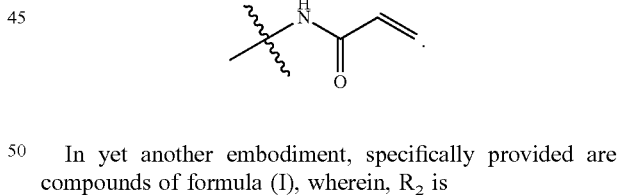

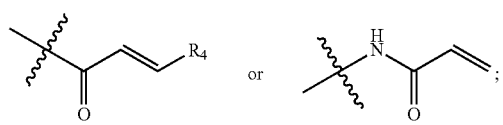

$R_4$ is hydrogen or —($CH_2$)—$NR_aR_b$; $R_a$ and $R_b$ are each independently hydrogen or alkyl; alternatively, $R_a$ and $R_b$ together with the nitrogen atom to which they are attached form an optionally substituted ring containing 0-2 additional heteroatoms independently selected from N, O and S.

In yet another embodiment, specifically provided are compounds of formula (I), wherein, R₁ is hydrogen; ring

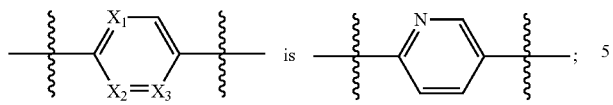

Y₁ is C;
Y₂ is N;
R₂ is

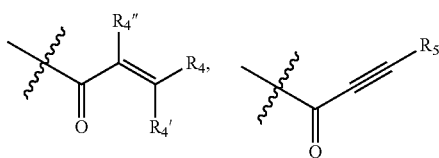

or —C≡N;
R₄, R₄', R₄" and R₅ are each independently hydrogen or alkyl.

In yet another embodiment, specifically provided are compounds of formula (I), wherein,
R₁ is hydrogen;
ring

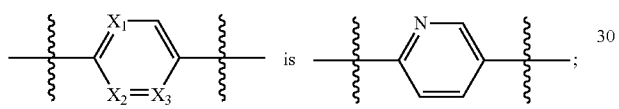

Y₁ is C;
Y₂ is N;
R₂ is

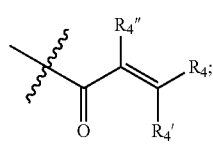

R₄, R₄' and R₄" are each independently hydrogen or alkyl.

In yet another embodiment, specifically provided are compounds of formula (I), wherein,
R₁ is hydrogen;
ring

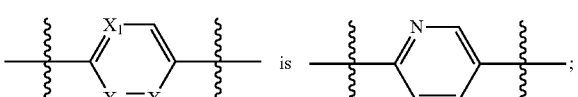

ring

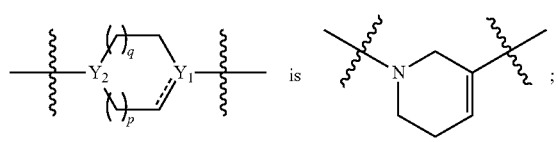

and
R₂ is

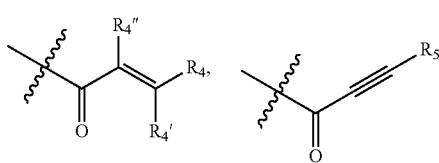

or —C≡N.

In yet another embodiment, specifically provided are compounds of formula (I), wherein, Y₁ is C; Y₂ is CH; and R₂ is

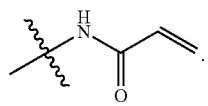 [SMILES: *NC(=O)C=C]

In yet another embodiment, specifically provided are compounds of formula (I), wherein, Y₁ is N; Y₂ is CH; and R₂ is

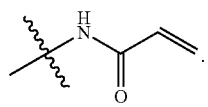 [SMILES: *NC(=O)C=C]

In yet another embodiment, specifically provided are compounds of formula (I), wherein, Y₁ is C; Y₂ is N; and R₂ is

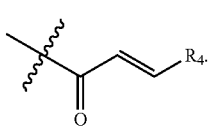

In yet another embodiment, specifically provided are compounds of formula (I), wherein, Y₂ is CH and R₂ is

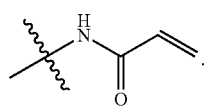 [SMILES: *NC(=O)C=C]

In yet another embodiment, specifically provided are compounds of formula (I), wherein, Y₂ is N and R₂ is

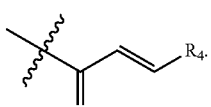

In yet another embodiment, specifically provided are compounds of formula (I), wherein, Y₁ and Y₂ each are N.

In yet another embodiment, specifically provided are compounds of formula (I), wherein, Y₁ is C when '-----' is a bond.

In yet another embodiment, specifically provided are compounds of formula (I), wherein, $Y_1$ is CH when '-----' is absent.

In yet another embodiment, specifically provided are compounds of formula (I), wherein, $Y_1$ is N when '-----' is absent.

In yet another embodiment, specifically provided are compounds of formula (I), wherein, the bond between chiral carbon atom and $R_1$ can be represented as , —, — or .

In yet another embodiment, provided are compounds of formula (I), wherein, the pyrazole ring is in equilibrium stage as shown here:

In yet another embodiment, the present invention provides a compound of formula (I),

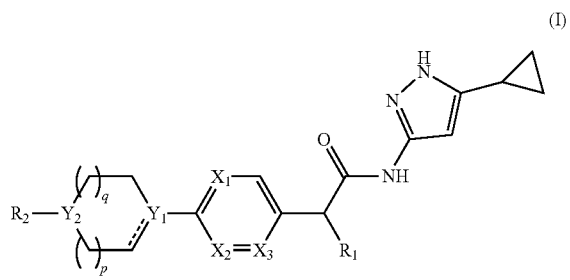

(I)

or a pharmaceutically acceptable salt, a N-oxide or a stereoisomer thereof, for use in the treatment of cancer, wherein, -----' is an optional bond;

each $X_1$, $X_2$ and $X_3$ are independently $CR_3$ or N;

each $Y_1$ and $Y_2$ are independently C, CH or N;

$R_1$ is hydrogen or alkyl;

$R_2$ is

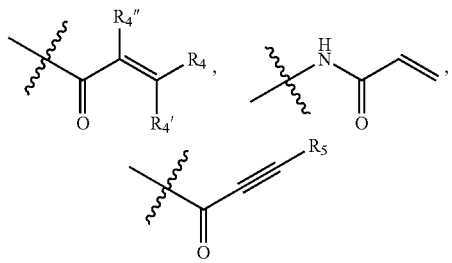

or —C≡N;

each $R_3$ is independently selected from hydrogen, halogen, cyano and alkyl;

$R_4$ is hydrogen, alkyl or —$(CH_2)_n$—$NR_aR_b$;

$R_4'$ & $R_4''$ are each independently hydrogen or alkyl;

$R_5$ is hydrogen or alkyl;

$R_a$ and $R_b$ are each independently hydrogen or alkyl; alternatively, $R_a$ and $R_b$ together with the nitrogen atom to which they are attached form an optionally substituted heterocyclic ring containing 0-2 additional heteroatoms independently selected from N, O and S;

n is 1 to 3; and p and q are each independently selected from 0 to 2.

In certain embodiments, the present invention provides a compound of formula (I) selected from:

| Comp. No. | IUPAC Name |
|---|---|
| 1 | 2-(4-(1-acryloyl-1,2,3,6-tetrahydropyridin-4-yl)phenyl)-N-(5-cyclopropyl-1H-pyrazol-3-yl)propanamide; |
| 2 | (S)-2-(4-(1-acryloyl-1,2,3,6-tetrahydropyridin-4-yl)phenyl)-N-(5-cyclopropyl-1H-pyrazol-3-yl)propanamide; |
| 3 | 2-(4-(1-acryloyl-1,2,3,6-tetrahydropyridin-4-yl)phenyl)-N-(5-cyclopropyl-1H-pyrazol-3-yl)-3-methylbutanamide; |
| 4 | 2-(1'-acryloyl-1',2',3',6'-tetrahydro-[2,4'-bipyridin]-5-yl)-N-(5-cyclopropyl-1H-pyrazol-3-yl)propanamide; |
| 5 | 2-(1'-acryloyl-1',2',3',6'-tetrahydro-[2,4'-bipyridin]-5-yl)-N-(5-cyclopropyl-1H-pyrazol-3-yl)propanamide (Isomer-1 of compound-4); |
| 6 | 2-(1'-acryloyl-1',2',3',6'-tetrahydro-[2,4'-bipyridin]-5-yl)-N-(5-cyclopropyl-1H-pyrazol-3-yl)propanamide (Isomer-2 of compound-4); |
| 7 | 2-(1'-acryloyl-1',2',3',6'-tetrahydro-[2,4'-bipyridin]-5-yl)-N-(5-cyclopropyl-1H-pyrazol-3-yl)-3-methylbutanamide; |
| 8 | N-(4'-(1 ((5-cyclopropyl-1H-pyrazol-3-yl)amino)-1-oxopropan-2-yl)-2,3,4,5-tetrahydro-[1,1'-biphenyl]-4-yl)acrylamide; |
| 9 | 2-(4-(1-acryloyl-2,3,6,7-tetrahydro-1H-azepin-4-yl)phenyl)-N-(5-cyclopropyl-1H-pyrazol-3-yl)propanamide; |
| 10 | N-(4-(4-(1-((5-cyclopropyl-1H-pyrazol-3-yl)amino)-1-oxopropan-2-yl)phenyl)cyclohexyl)acrylamide; |
| 11 | N-(4-(4-(1-((5-cyclopropyl-1H-pyrazol-3-yl)amino)-1-oxopropan-2-yl)phenyl)cyclohexyl)acrylamide; |
| 12 | (S)-2-(4-(1-acryloylpiperidin-4-yl)phenyl)-N-(5-cyclopropyl-1H-pyrazol-3-yl)propanamide; |
| 13 | 2-(6-(1-acryloylpiperidin-4-yl)pyridin-3-yl)-N-(5-cyclopropyl-1H-pyrazol-3-yl)propanamide; |
| 14 | (S,E)-N-(5-cyclopropyl-1H-pyrazol-3-yl)-2-(4-(1-(4-(diethylamino)but-2-enoyl)-1,2,3,6-tetrahydropyridin-4-yl)phenyl)propanamide; |

-continued

| Comp. No. | IUPAC Name |
|---|---|
| 15 | (S,E)-N-(5-cyclopropyl-1H-pyrazol-3-yl)-2-(4-(1-(4-(dimethylamino)but-2-enoyl)-1,2,3,6-tetrahydropyridin-4-yl)phenyl)propanamide; |
| 16 | (S,E)-N-(5-cyclopropyl-1H-pyrazol-3-yl)-2-(4-(1-(4-morpholinobut-2-enoyl)-1,2,3,6-tetrahydropyridin-4-yl)phenyl)propanamide; |
| 17 | 2-(4-(4-acryloylpiperazin-1-yl)phenyl)-N-(5-cyclopropyl-1H-pyrazol-3-yl)propanamide; |
| 18 | 2-(4-(4-acryloylpiperazin-1-yl)phenyl)-N-(5-cyclopropyl-1H-pyrazol-3-yl)propanamide (Isomer-1 of compound-17); |
| 19 | 2-(4-(4-acryloylpiperazin-1-yl)phenyl)-N-(5-cyclopropyl-1H-pyrazol-3-yl)propanamide (Isomer-2 of compound-17); |
| 20 | 2-(6-(4-acryloylpiperazin-1-yl)pyridin-3-yl)-N-(5-cyclopropyl-1H-pyrazol-3-yl)propanamide; |
| 21 | N-(1-(4-(1-((5-cyclopropyl-1H-pyrazol-3-yl)amino)-1-oxopropan-2-yl)phenyl)piperidin-4-yl)acrylamide; |
| 22 | 2-(1'-acryloyl-1',2',3',6'-tetrahydro-[2,4'-bipyridin]-5-yl)-N-(5-cyclopropyl-1H-pyrazol-3-yl)butanamide; |
| 23 | 2-(4-(1-acryloylazepan-4-yl)phenyl)-N-(5-cyclopropyl-1H-pyrazol-3-yl)propanamide; |
| 24 | 2-(6-(4-acryloyl-1,4-diazepan-1-yl)pyridin-3-yl)-N-(5-cyclopropyl-1H-pyrazol-3-yl)propanamide; |
| 25 | 2-(4-(1-acryloylazocan-5-yl)phenyl)-N-(5-cyclopropyl-1H-pyrazol-3-yl)propanamide; |
| 26 | 2-(2-(1-acryloyl-1,2,3,6-tetrahydropyridin-4-yl)pyrimidin-5-yl)-N-(5-cyclopropyl-1H-pyrazol-3-yl)propanamide; |
| 27 | 2-(6-(1-acryloyl-1,2,3,6-tetrahydropyridin-4-yl)pyridazin-3-yl)-N-(5-cyclopropyl-1H-pyrazol-3-yl)propanamide; |
| 28 | 2-(5-(1-acryloyl-1,2,3,6-tetrahydropyridin-4-yl)pyrazin-2-yl)-N-(5-cyclopropyl-1H-pyrazol-3-yl)propanamide; |
| 29 | 2-(4-(1-acryloyl-1,2,3,6-tetrahydropyridin-4-yl)-3-fluorophenyl)-N-(5-cyclopropyl-1H-pyrazol-3-yl)propanamide; |
| 30 | 2-(1'-acryloyl-3-fluoro-1',2',3',6'-tetrahydro-[2,4'-bipyridin]-5-yl)-N-(5-cyclopropyl-1H-pyrazol-3-yl)propanamide; |
| 31 | 2-(1'-acryloyl-3-chloro-1',2',3',6'-tetrahydro-[2,4'-bipyridin]-5-yl)-N-(5-cyclopropyl-1H-pyrazol-3-yl)propanamide; |
| 32 | 2-(1'-acryloyl-3-cyano-1',2',3',6'-tetrahydro-[2,4'-bipyridin]-5-yl)-N-(5-cyclopropyl-1H-pyrazol-3-yl)propanamide; |
| 33 | 2-(1'-acryloyl-3-methyl-1',2',3',6'-tetrahydro-[2,4'-bipyridin]-5-yl)-N-(5-cyclopropyl-1H-pyrazol-3-yl)propanamide; |
| 34 | (S)-2-(4-(1-acryloyl-1,2,5,6-tetrahydropyridin-3-yl)phenyl)-N-(5-cyclopropyl-1H-pyrazol-3-yl)propanamide; |
| 35 | 2-(1'-acryloyl-1',2',5',6'-tetrahydro-[2,3'-bipyridin]-5-yl)-N-(5-cyclopropyl-1H-pyrazol-3-yl)propanamide; |
| 36 | (Isomer-1 of compound-35): 2-(1'-acryloyl-1',2',5',6'-tetrahydro-[2,3'-bipyridin]-5-yl)-N-(5-cyclopropyl-1H-pyrazol-3-yl)propanamide; |
| 37 | (Isomer-2 of compound-35): 2-(1'-acryloyl-1',2',5',6'-tetrahydro-[2,3'-bipyridin]-5-yl)-N-(5-cyclopropyl-1H-pyrazol-3-yl)propanamide; |
| 38 | 2-(6-(1-acryloyl-2,5-dihydro-1H-pyrrol-3-yl)pyridin-3-yl)-N-(5-cyclopropyl-1H-pyrazol-3-yl)propanamide; |
| 39 | 2-(1'-acryloyl-1',2',5',6'-tetrahydro-[2,3'-bipyridin]-5-yl)-N-(5-cyclopropyl-1H-pyrazol-3-yl)butanamide; |
| 40 | 2-(4-(1-acryloyl-1,2,5,6-tetrahydropyridin-3-yl)phenyl)-N-(5-cyclopropyl-1H-pyrazol-3-yl)-3-methylbutanamide; |
| 41 | 2-(6-(1-acryloylpiperidin-3-yl)pyridin-3-yl)-N-(5-cyclopropyl-1H-pyrazol-3-yl)propanamide; |
| 42 | 2-(4-(1-acryloyl-1,2,5,6-tetrahydropyridin-3-yl)-3-fluorophenyl)-N-(5-cyclopropyl-1H-pyrazol-3-yl)propanamide; |
| 43 | 2-(1'-acryloyl-1',2',5',6'-tetrahydro-[2,3'-bipyridin]-5-yl)-N-(5-cyclopropyl-1H-pyrazol-3-yl)-3-methylbutanamide; |
| 44 | 2-(4-(1-acryloyl-1,2,3,6-tetrahydropyridin-4-yl)-3-fluorophenyl)-N-(5-cyclopropyl-1H-pyrazol-3-yl)propanamide; |
| 45 | 2-(4-(1-acryloyl-1,2,3,6-tetrahydropyridin-4-yl)-3-fluorophenyl)-N-(5-cyclopropyl-1H-pyrazol-3-yl)propanamide; |
| 46 | 2-(6-(1-acryloyl-2,5-dihydro-1H-pyrrol-3-yl)pyridin-3-yl)-N-(5-cyclopropyl-1H-pyrazol-3-yl)propanamide; |
| 47 | 2-(6-(1-acryloyl-2,5-dihydro-1H-pyrrol-3-yl)pyridin-3-yl)-N-(5-cyclopropyl-1H-pyrazol-3-yl)propanamide; |
| 48 | 2-(6-(1-acryloylpyrrolidin-3-yl)pyridin-3-yl)-N-(5-cyclopropyl-1H-pyrazol-3-yl)propanamide; |
| 49 | 2-(1'-acryloyl-1',2',5',6'-tetrahydro-[2,3'-bipyridin]-5-yl)-N-(5-cyclopropyl-1H-pyrazol-3-yl)acetamide; |
| 50 | N-(5-cyclopropyl-1H-pyrazol-3-yl)-2-(1'-propioloyl-1',2',3',6'-tetrahydro-[2,4'-bipyridin]-5-yl)propanamide; |
| 51 | 2-(1'-(but-2-ynoyl)-1',2',3',6'-tetrahydro-[2,4'-bipyridin]-5-yl)-N-(5-cyclopropyl-1H-pyrazol-3-yl)propanamide; |
| 52 | 2-(1'-(but-2-ynoyl)-1',2',5',6'-tetrahydro-[2,3'-bipyridin]-5-yl)-N-(5-cyclopropyl-1H-pyrazol-3-yl)propanamide; |

| Comp. No. | IUPAC Name |
|---|---|
| 53 | 2-(6-(1-acryloyl-2,5-dihydro-1H-pyrrol-3-yl)pyridin-3-yl)-N-(5-cyclopropyl-1H-pyrazol-3-yl)acetamide; |
| 54 | (E)-2-(1'-(but-2-enoyl)-1',2',5',6'-tetrahydro-[2,3'-bipyridin]-5-yl)-N-(5-cyclopropyl-1H-pyrazol-3-yl)acetamide; |
| 55 | N-(5-cyclopropyl-1H-pyrazol-3-yl)-2-(1'-(3-methylbut-2-enoyl)-1',2',5',6'-tetrahydro-[2,3'-bipyridin]-5-yl)acetamide; |
| 56 | 2-(1'-(but-2-ynoyl)-1',2',5',6'-tetrahydro-[2,3'-bipyridin]-5-yl)-N-(5-cyclopropyl-1H-pyrazol-3-yl)acetamide; |
| 57 | N-(5-cyclopropyl-1H-pyrazol-3-yl)-2-(1'-methacryloyl-1',2',5',6'-tetrahydro-[2,3'-bipyridin]-5-yl)acetamide; |
| 58 | N-(5-cyclopropyl-1H-pyrazol-3-yl)-2-(1'-propioloyl-1',2',5',6'-tetrahydro-[2,3'-bipyridin]-5-yl)acetamide; |
| 59 | 2-(1'-acryloyl-1',2',3',6'-tetrahydro-[2,4'-bipyridin]-5-yl)-N-(5-cyclopropyl-1H-pyrazol-3-yl)acetamide; |
| 60 | N-(5-cyclopropyl-1H-pyrazol-3-yl)-2-(6-(1-propioloyl-2,5-dihydro-1H-pyrrol-3-yl)pyridin-3-yl)acetamide; |
| 61 | 2-(1'-cyano-1',2',5',6'-tetrahydro-[2,3'-bipyridin]-5-yl)-N-(5-cyclopropyl-1H-pyrazol-3-yl)acetamide; and |
| 62 | 2-(1'-cyano-1',2',3',6'-tetrahydro-[2,4'-bipyridin]-5-yl)-N-(5-cyclopropyl-1H-pyrazol-3-yl)acetamide; | or a pharmaceutically acceptable salt thereof or a stereoisomer thereof.

In a certain embodiment, the present invention relates to a pharmaceutical composition, comprising at least one compound of formula (I), or a pharmaceutically acceptable salt or a stereoisomer thereof, and a pharmaceutically acceptable carrier or excipient.

In a certain embodiment, the present invention relates to a compound or a pharmaceutically acceptable salt or a stereoisomer thereof, for use as a medicament.

Pharmaceutical Compositions

In certain embodiments, present invention provides a pharmaceutical composition comprising the compound of formula (I) and a pharmaceutically acceptable salt or a stereoisomer thereof, and a pharmaceutically acceptable carrier or excipient.

In certain embodiments, the pharmaceutical composition of the present invention further comprises at least one agent selected from an anticancer agent, a chemotherapy agent, and an antiproliferative compound.

In certain embodiments, the present invention provides a pharmaceutical composition comprising a compound of formula (I), or a pharmaceutically acceptable salt thereof or a stereoisomer thereof as described herein and at least one pharmaceutically acceptable excipient (such as a pharmaceutically acceptable carrier or diluent). Preferably, the pharmaceutical composition comprises a therapeutically effective amount of at least one compound described herein. The compounds described in the present invention may be associated with a pharmaceutically acceptable excipient (such as a carrier or a diluent) or be diluted by a carrier or enclosed within a carrier which can be in the form of a capsule, sachet, paper or other container.

The compounds of the present invention may be used as single drug or as a pharmaceutical composition in which the compound is mixed with various pharmacologically acceptable materials.

The compounds of the invention are typically administered in the form of a pharmaceutical composition. Such compositions can be prepared using procedures well known in the pharmaceutical art and comprise at least one compound of the invention. The pharmaceutical composition of the present invention comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents, solvents and the like.

The pharmaceutical composition can be administered by oral, parenteral or inhalation routes. Examples of the parenteral administration include administration by injection, percutaneous, transmucosal, intranasal and transpulmonary administrations.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters and polyoxyethylene.

The pharmaceutical composition may also include one or more pharmaceutically acceptable auxiliary agents, wetting agents, suspending agents, preserving agents, buffers, sweetening agents, flavouring agents, colorants or any combination of the foregoing.

The pharmaceutical compositions may be in conventional forms, for example, tablets, capsules, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the invention to the appropriate or desired site of action. Suitable routes of administration include, but are not limited to, oral, nasal, buccal, dermal, intradermal, transdermal, parenteral, rectal, subcutaneous, intravenous, intraurethral, intramuscular or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions, suspensions, sterile injectable liquids and solutions.

Topical dosage forms of the compounds include ointments, pastes, creams, lotions, powders, solutions, eye or ear drops, impregnated dressings, and may contain appropriate conventional additives such as preservatives and solvents to assist drug penetration.

The pharmaceutical compositions of the present invention may be prepared by conventional techniques known in literature.

Suitable doses of the compounds for use in treating the diseases or disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms, and suitable pharmaceutical excipients can also be well used and adjusted by those skilled in the art. All changes and modifications are envisioned within the scope of the present invention.

According to one embodiment, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Isotopically labeled compounds of the present inventions can generally be prepared by following procedures analogous to those disclosed in the schemes and/or in the examples herein below, by substituting an isotopically labeled reagent for a non-isotopically labeled reagent.

Methods of Treatment

In certain embodiments, the present invention provides compounds of formula (I) for use as a medicament.

In certain embodiments, the invention provides the use of the compounds of the present invention in the manufacture of a medicament.

In certain embodiments, the invention provides a method of treating cancer or proliferative disorder, comprising administration of a therapeutically effective amount of a compound of formula (I) or a pharmaceutically acceptable salt or a stereoisomer thereof.

In certain embodiments, the present invention provides methods for inhibiting growth of tumour cells and/or metastasis by administering a therapeutically effective amount of a compound of formula (I) or a pharmaceutically acceptable salt or a stereoisomer thereof.

In certain embodiments, the present invention provides methods for treating cancer or proliferative disorder, by administering a therapeutically effective amount of a compound of formula (I) or a pharmaceutically acceptable salt or a stereoisomer thereof.

According to yet another embodiment, the compounds of formula (I) are useful in the treatment of proliferative diseases such as cancer, viral diseases, fungal diseases, neurological/neurodegenerative disorders, autoimmune diseases, inflammation, arthritis, anti-proliferative (e.g., ocular retinopathy), neuronal, alopecia and cardiovascular disease.

According to yet another embodiment, the cancer is selected from the group consisting of a carcinoma, including that of the breast, liver, lung, colon, kidney, bladder, including small cell lung cancer, non-small cell lung cancer, head and neck, thyroid, esophagus, stomach, pancreas, ovary, gall bladder, cervix, prostate, and skin, including squamous cell carcinoma; hematopoietic tumors of lymphoid lineage, including leukemia, acute lymphoblastic leukemia, acute lymphocytic leukemia, Hodgkins lymphoma, non-Hodgkins lymphoma, B-cell lymphoma, T-cell lymphoma, hairy cell lymphoma, myeloma, mantle cell lymphoma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including seminoma, melanoma, osteosarcoma, teratocarcinoma, keratoacanthoma, xenoderma pigmentosum, thyroid follicular cancer and Kaposi's sarcoma.

According to yet another embodiment, the present invention provides a compound of formula (I) for use in the treatment of Myotonic Dystrophy type 1, Myotonic Dystrophy type 2, Fragile X associated tremor/ataxia syndrome, amylotrophic lateral sclerosis (ALS) and frontotemporal dementia, Huntington's disease like 2, Huntington's disease, several types of Spinocerebellar Ataxia, Dentatorubral-pallidoluysian atrophy and Spinal and Bulbar Muscular Atrophy.

In certain embodiments, the compounds of the present invention are selective CDK12/13 inhibitors (e.g., being selective for inhibition of CDK12/13 over CDK7).

In another embodiment, the present invention provides a method of inhibiting CDK12/13 in a subject, comprising administering to the subject a compound of formula (I).

In another embodiment, the present invention provides a method of selectively inhibiting CDK12/13 in a subject, comprising administering to the subject in need thereof a therapeutically effective amount of a compound of the present invention.

In another embodiment, the present invention provides a pharmaceutical composition for use in treating and/or preventing a disease and/or disorder associated with aberrant activity of CDK12/13.

In another embodiment, the present invention provides a pharmaceutical composition for use in treating a subject suffering from a disease or condition associated with aberrant activity of CDK12/13.

In another embodiment, the present invention provides pharmaceutical composition comprising the compound of formula (I), for use in treating a subject suffering from a disease or condition associated with aberrant activity of CDK12/13.

In another embodiment, the present invention provides a method of treating diseases and/or disorders or condition mediated by CDK12/13 in a subject comprising administering to the subject in need thereof a therapeutically effective amount of a compound of formula (I) of the present invention.

In another embodiment, the present invention provides a method of treating diseases and/or disorder or condition mediated by CDK12/13 in a subject comprising administering a therapeutically effective amount of a compound of formula (I).

According to the foregoing embodiment, the CDK12/13 mediated disorder or disease or condition is selected from the group consisting of a cancer, an inflammatory disorder, an auto-inflammatory disorder and an infectious disease.

In yet another embodiment, the compounds of formula (I) as disclosed in the present invention are formulated for pharmaceutical administration.

Yet another embodiment of the present invention provides use of compounds of formula (I) of the present invention in the treatment and prevention of diseases or disorder associated with the aberrant activity of CDK12/13.

Yet another embodiment of the present invention provides use of compounds of formula (I) of the present invention in the treatment of a cancer, an inflammatory disorder, an auto-inflammatory disorder or an infectious disease.

Yet another embodiment of the present invention provides the use of a compound of formula (I) or a pharmaceutically acceptable salt thereof, in treating and/or preventing a disease for which the symptoms thereof are treated, improved, diminished and/or prevented by selective inhibition of CDK12/13.

According to yet another embodiment, the CDK12/13 mediated disorder and/or disease or condition is proliferative disease or disorder or condition.

In yet another embodiment, the diseases and/or disorder mediated by CDK12/13 is selected from the group consisting of a cancer, an inflammatory disorder, an auto-inflammatory disorder and an infectious disease.

In other embodiments, the proliferative disease to be treated or prevented using the compounds of formula (I) will typically be associated with aberrant activity of CDK12/13.

In certain embodiments, CDK12/13 refers to CDK 12 or CDK 13 or CDK 12 and CDK13.

According to yet another embodiment, the disorder or condition mediated by CDK12/13 is Myotonic Dystrophy type 1, Myotonic Dystrophy type 2, Fragile X associated tremor/ataxia syndrome, amylotrophic lateral sclerosis (ALS) and frontotemporal dementia, Huntington's disease like 2, Huntington's disease, several types of Spinocerebellar Ataxia, Dentatorubral-pallidoluysian atrophy and Spinal and Bulbar Muscular Atrophy.

According to yet another embodiment, the diseases and/or disorder mediated by CDK12/13 is Myotonic dystrophy.

According to yet another embodiment, the compounds of formula (I) of the present invention are useful in the treatment of Myotonic dystrophy.

According to yet another embodiment, the present invention provides a method of treating Myotonic dystrophy by administering a therapeutically effective amount of a compound of formula (I).

According to yet another embodiment, the present invention provides compounds of formula (I) in the manufacture of a medicament for treating Myotonic dystrophy.

According to yet another embodiment, the subject is a mammal including human.

According to yet another embodiment, the present invention provides compounds of formula (I) or pharmaceutically acceptable salts or stereoisomers thereof, for use as a medicament.

According to yet another embodiment, the invention provides the use of the compounds of formula (I) of the present invention in the manufacture of a medicament.

According to yet another embodiment, the present invention provides compounds of formula (I) or pharmaceutically acceptable salts or stereoisomers thereof, for use in the treatment of cancer.

According to yet another embodiment, the present invention provides compounds of formula (I) or pharmaceutically acceptable salts or stereoisomers thereof, for use in the treatment of an inflammatory disorder, an auto-inflammatory disorder or an infectious disease.

According to yet another embodiment, the invention provides the use of the compounds of formula (I) of the present invention in the manufacture of a medicament for the treatment of diseases and/or disorder associated with the aberrant activity of CDK12/13.

In yet another embodiment, the invention provides the use of the compounds of formula (I) of the present invention in the manufacture of a medicament for the treatment of cancer.

In yet another embodiment, the invention provides the use of the compounds of formula (I) of the present invention in the manufacture of a medicament for the treatment of an inflammatory disorder, an auto-inflammatory disorder or an infectious disease.

According to yet another embodiment, the present invention provides compounds of formula (I) for use as a medicament for treating a subject suffering from diseases and/or disorder associated with aberrant activity of CDK12/13.

According to yet another embodiment, the present invention comprises administering to the subject in need thereof a therapeutically effective amount of a compound of formula (I) of the present invention along with one or more additional chemotherapeutic agents independently selected from anti-proliferative agents, anti-cancer agents, immunosuppressant agents and pain-relieving agents.

The method(s) of treatment of the present invention comprises administering a safe and effective amount of a compound according to formula (I) or a pharmaceutically acceptable salt thereof to a patient (particularly a human) in need thereof.

Compounds of the invention are indicated both in the therapeutic and/or prophylactic treatment of the above-mentioned conditions. For the above-mentioned therapeutic uses the dosage administered will, of course, vary with the compound employed, the mode of administration, the treatment desired and the disorder or disease indicated.

Definitions

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used herein, the term "optionally substituted" refers to replacement of one or more hydrogen radicals in a given structure with a radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, am inocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, am inocarbonylalkyl, acyl, aralkoxycarbonyl, carboxylic acid, sulfonic acid, sulfonyl, phosphonic acid, cycloalkyl, heteroaryl, and aliphatic. It is understood that the substituent may be further substituted.

As used herein, unless otherwise defined the term "alkyl" alone or in combination with other term(s) means saturated aliphatic hydrocarbon chain, including $C_1$-$C_{10}$ straight or $C_1$-$C_{10}$ branched alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include but are not limited to methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

As used herein, the term "halo" or "halogen" alone or in combination with other term(s) means fluorine, chlorine, bromine or iodine.

As used herein, the term "cyano" refers to a —CN group.

The term "heteroatom" as used herein designates a sulfur, nitrogen or oxygen atom.

As used herein, the term "heterocycloalkyl" refers to a non-aromatic, saturated or partially saturated, bridged bicyclic, spirocyclic, monocyclic or polycyclic ring system of 3 to 15 member having at least one heteroatom or heterogroup selected from O, N, S, S(O), S(O)$_2$, NH or C(O) with the remaining ring atoms being independently selected from the group consisting of carbon, oxygen, nitrogen, and sulfur. The term "heterocycloalkyl" also refers to the bridged bicyclic ring system having at least one heteroatom or hetero group selected from O, N, S, S(O), S(O)$_2$, NH or C(O). Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, aza-bicyclooctanyl, azocinyl, chromanyl, isochromanyl xanthenyl, 2-oxa-6-azaspiro[3.3]heptanyl, 3-oxa-8-azabicyclo[3.2.1]octanyl and N-oxides thereof. Attachment of a heterocycloalkyl substituent can occur via either a carbon atom or a heteroatom. A heterocycloalkyl group can be optionally further substituted.

As used herein, the term "heteroaryl" refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. Preferably, "heteroaryl" is a 5- to 6-membered ring. The rings may contain from 1 to 4 heteroatoms selected from N, O and S, wherein the N or S atom is optionally oxidized or the N atom is optionally quarternized. Any suitable ring position of the heteroaryl moiety may be covalently linked to the defined chemical structure. Examples of "heteroaryl" include but are not limited to furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, 3-fluoropyridyl, pyrimidinyl, pyrazinyl, pyridazinyl, benzoxazolyl, benzisoxazolyl; benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carbolinyl, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl and the like. Heteroaryl group may be optionally further substituted.

As used herein, the term "heterocyclyl" or "heterocyclic" alone or in combination with other term(s) includes both "heterocycloalkyl" and "heteroaryl" groups which are as defined above.

Certain of the compounds disclosed herein can exist as N-oxides. For example, it is known that the pyrazoles can form N-oxides on treatment with a suitable oxidizing agent. Similarly, it is known that the pyridine ring nitrogen can be oxidized on treatment with a suitable oxidizing agent to form an N-oxide.

As used herein, the term "compound(s)" comprises the compounds disclosed in the present invention.

As used herein, the term "comprise" or "comprising" is generally used in the sense of include, that is to say permitting the presence of one or more features or components.

As used herein, the term "or" means "and/or" unless stated otherwise.

As used herein, the term "including" as well as other forms, such as "include", "includes" and "included" is not limiting.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the term "pharmaceutical composition" refers to a composition(s) containing a therapeutically effective amount of at least one compound of formula (I) or its pharmaceutically acceptable salt; and a conventional pharmaceutically acceptable carrier.

The pharmaceutical composition(s) of the present invention can be administered orally, for example in the form of tablets, coated tablets, pills, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of ointments or creams or transdermals, in the form of patches, or in other ways, for example in the form of aerosols or nasal sprays.

The pharmaceutical composition(s) usually contain(s) about 1% to 99%, for example, about 5% to 75%, or from about 10% to about 30% by weight of the compound of formula (I) or pharmaceutically acceptable salts thereof. The amount of the compound of formula (I) or pharmaceutically acceptable salts thereof in the pharmaceutical composition (s) can range from about 1 mg to about 1000 mg or from about 2.5 mg to about 500 mg or from about 5 mg to about 250 mg or in any range falling within the broader range of 1 mg to 1000 mg or higher or lower than the afore mentioned range.

As used herein, the term "treat", "treating" and "treatment" refer to any treatment of a disease in a mammal, including: (a) Inhibiting the disease, i.e., slowing or arresting the development of clinical symptoms; and/or (b) relieving the disease, i.e., causing the regression of clinical symptoms and/or (c) alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "therapeutically effective amount" refers to that amount of a compound of formula (I) or a pharmaceutically acceptable salt or a stereoisomer thereof; or a composition comprising the compound of formula (I) or a pharmaceutically acceptable salt or a stereoisomer thereof, effective in producing the desired therapeutic response in a particular patient suffering from a diseases or disorder, in particular their use in diseases or disorder associated with cancer. Particularly, the term "therapeutically effective amount" includes the amount of the compound of formula (I) or a pharmaceutically acceptable salt or a stereoisomer thereof, when administered, that induces a positive modification in the disease or disorder to be treated or is sufficient to prevent development of, or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed the particular pharmaceutically acceptable carrier utilized.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

"Pharmaceutically acceptable salt" refers to a product obtained by reaction of the compound of the present invention with a suitable acid or a base and that possesses the desired pharmacological activity of the parent compound. Pharmaceutically acceptable salts of the compounds of this invention include those derived from suitable inorganic and organic acids and bases. Such salts include: acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methane sulfonic acid, ethane sulfonic acid, 1,2-ethane-disulfonic acid, 2-hydroxyethanesulfonic acid, benzene sulfonic acid, 4-chlorobenzenesulfonic acid, 2-naphthalenesulfonic acid, 4-toluenesulfonic acid, camphor sulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxyl naphthoic acid, salicylic acid, stearic acid, muconic acid, and the like. Certain compounds of the invention (compounds of formula (I)) can form pharmaceutically acceptable salts with various organic bases such as lysine, arginine, guanidine, diethanolamine or metformin.

The term "stereoisomers" refers to any enantiomers, diastereoisomers, or geometrical isomers of the compounds of Formula (I), wherever they are chiral or when they bear one or more double bonds. When the compounds of the Formula (I) and related formulae are chiral, they can exist in racemic or in optically active form. It should be understood that the invention encompasses all stereochemical isomeric forms, including diastereomeric, enantiomeric and epimeric forms, as well as d-isomers and l-isomers and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E) and zusammen (Z) isomers as well as the appropriate mixtures thereof.

EXPERIMENTAL SECTION

Development of CDK12/13 Specific Inhibitor

The primary aim of the present invention was to improve the CDK12/13 specificity of the compounds disclosed in WO 2016/193939. Surprisingly, it was found that by altering the substituent relationship of the central aromatic ring from a 1,3 relationship (i.e. meta substituted) to a 1,4 relationship (i.e. para substituted), the selectivity of the compound for the CDK12/13 receptor was greatly improved.

For example, modifying compound-A (compound no. 84 in WO 2016/193939) by changing the substituent relationship of the central aromatic moiety from meta to para (thereby producing compound-15 of the present invention) resulted in a significant loss of binding at the CDK7 receptor whilst maintaining excellent binding at the CDK12/13 receptor.

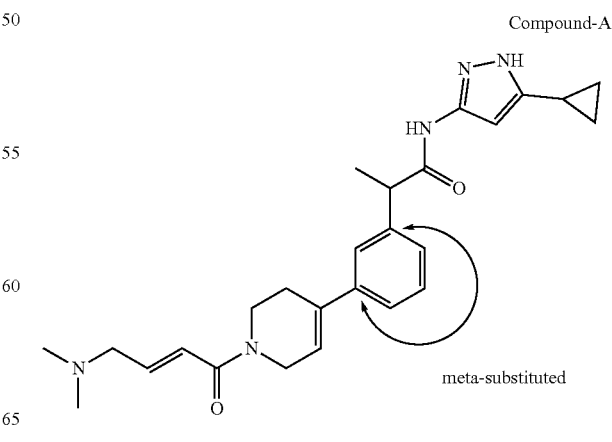

Compound-A meta-substituted

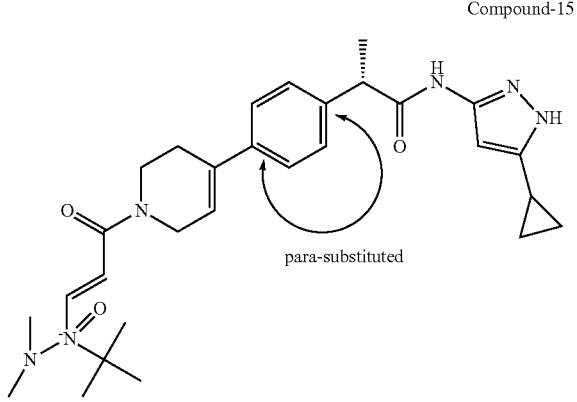

Compound-15 para-substituted

| Parameter | Compound A | Compound 15 |
|---|---|---|
| Jurkat Cells, CDK12 Target $Occ_{50}$ (nM) | 305.4 | 204.4 |
| Jurkat Cells, CDK7 Target $Occ_{50}$ (nM) | 129.9 | 1671 |
| Ratio CDK7/CDK12 | 0.425 | 8.175 |

Compound-15 shows >8 folds binding affinity towards CDK12 in comparison to CDK7; whereas Compound-A shows 0.4 fold binding affinity towards CDK12 as compared to that in CDK7.

Accordingly, reducing the binding affinity of the compound for CDK7 whilst maintaining or improving the binding affinity for CDK12/13 results in an inhibitor that selectively targets CDK12/13 over CDK7. The following sets out the synthesis and evaluation of further exemplary CDK12/13 inhibitors of the invention having a central aromatic group with the 1,4 substituent relationship.

General Modes of Preparation:

Following general guidelines applies to all experimental procedures described here. Until otherwise stated, experiments are performed under positive pressure of nitrogen, temperature describes are the external temperature (i.e. oil bath temperature). Reagents and solvents received from vendors are used as such without any further drying or purification. Molarities mentioned here for reagents in solutions are approximate were not verified by a prior titration with a standard. All reactions were stirred under magnetic stir bar. Cooling to temperatures below 0° C. was done using a bath of either acetone/dry ice or wet ice/salts. Magnesium sulfate and sodium sulfate were used as solvent drying agent after reaction work up and are interchangeable. Removing of solvents under reduced pressure or under vacuum means distilling of solvents in rotary evaporator.

Compounds of this invention may be made by synthetic chemical processes, examples of which are shown herein. It is meant to be understood that the order of the steps in the processes may be varied, that reagents, solvents and reaction conditions may be substituted for those specifically mentioned and that vulnerable moieties may be protected and deprotected, as necessary.

The specifics of the process for preparing compounds of the present invention are detailed in the experimental section.

The present invention shall be illustrated by means of some examples, which are not construed to be viewed as limiting the scope of the invention.

Unless otherwise stated, work-up includes distribution of the reaction mixture between the organic and aqueous phases, separation of layers and drying the organic layer over anhydrous sodium sulphate, filtration and evaporation of the solvent. Purification, unless otherwise mentioned, includes purification by silica gel chromatographic techniques, generally using ethyl acetate/petroleum ether mixture of a suitable polarity as the mobile phase.

Analysis for the compounds of the present invention unless mentioned, was conducted in the general methods well known to the person skilled in the art. Having described the invention with reference to certain preferred embodiments, other embodiments will become apparent to one skilled in the art from consideration of the specification. The invention is further defined by reference to the following examples, describing in detail the analysis of the compounds of the invention.

It will be apparent to those skilled in the art that many modifications, both to materials and methods, may be practiced without departing from the scope of the invention. Some of the intermediates were taken to next step based on TLC results, without further characterization, unless otherwise specified.

The following abbreviations refer respectively to the definitions herein: EtOH (Ethanol); rt (Retention time); RT (Room temperature); DMF (Dimethylformamide); h (hour); THF (tetrahydrofuran); HATU (1-[Bis(dimethylamino)methylene]-1H-1,2,3-triazolo[4,5-b]pyridinium 3-oxidhexafluorophosphate); LCMS (Liquid chromatography mass spectroscopy); HCl (Hydrochloric acid); DCM, $CH_2Cl_2$ (Dichloromethane); TFA (Trifluoroacetic acid); TLC (Thin layer chromatography); DIPEA (Diisopropyl Ethyl amine); $Na_2SO_4$ (Sodium sulphate); ACN/$CH_3CN$ (Acetonitrile); Pd(PPh$_3$)$_4$ (Tetrakis[triphenylphosphine]palladium(0)); MeOH (Methanol); (COCl)$_2$ (Oxalyl chloride); DMSO-D$_6$ (Dimethyl sulfoxide-d); HPLC (High pressure liquid chromatography); TEA (triethyl amine), $Cs_2CO_3$ (Cesium carbonate); MHz (megahertz); s (singlet); m (multiplet); and d (doublet).NMM (N-Methylmorpholine); n-BuLi (n-Butyl lithium); $H_2O_2$ (Hydrogen peroxide); LiOH (Lithium hydroxide); $PtO_2$ (Platinum(IV) oxide); KHMDS (Potassium bis(trimethylsilyl)amide solution); TBAF (Tetra-n-butylammonium fluoride).

Synthesis of Intermediates

Intermediate-1: Synthesis of
2-(6-chloropyridin-3-yl)-3-methylbutanoic acid

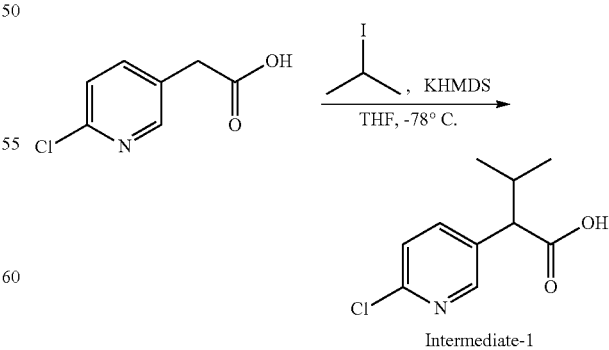

Intermediate-1

2-(6-chloropyridin-3-yl)acetic acid (4 g, 24 mmol) in THF (30 mL) was added to a solution of 1M KHMDS (55 mL, 55 mmol) in THF at −78° C. over a period of 10 min.

Reaction mass was stirred for 1 h at the same temperature, followed by drop wise addition of isopropyl iodide (5.17 g, 30 mmol) over a period of 5 min. Reaction mixture was warm to room temperature and stirred overnight. Reaction mass was quenched with 2N HCl and organic layer was separated from aqueous layer. Aqueous layer was further extracted with ethyl acetate and combined organic layer was dried over anhydrous sodium sulphate and concentrated under reduced pressure to afford crude compound. Crude was further purified with silica column chromatography by eluting with ethylacetate:hexane (30:70) mixture as mobile phase to afford pure title compound (3.7 g, 74%). LCMS: m/z=214 (M+H)$^+$.

Intermediate-2: Synthesis of tert-butyl 5-(2-(4-bromophenyl)propanamido)-3-cyclopropyl-1H-pyrazole-1-carboxylate

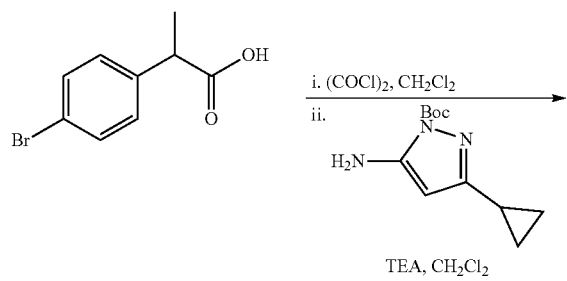

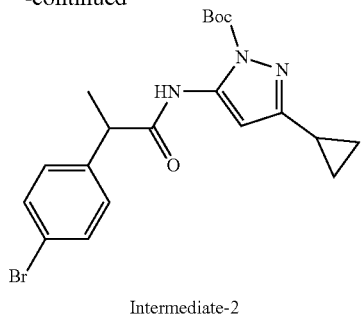

Intermediate-2

2-(4-bromophenyl)propanoic acid (1 g, 4.36 mmol) (synthesis carried out as described in reference WO2016/193939 A1) was taken in DCM (10 mL) at 0° C. with catalytic amount of DMF and added oxalyl chloride (0.82 g, 6.54 mmol), allowed to stir the reaction mass at room temperature for 1.5 h. Concentrated the reaction mass under vacuum and the residue was dissolved in dry DCM (5 mL) and added to the cooled solution of tert-butyl 5-amino-3-cyclopropyl-1H-pyrazole-1-carboxylate (0.97 g, 4.36 mmol) (synthesis carried out as described in reference *Tetrahedron Letters*, 2005, vol. 46, #6 p. 933-935), TEA (1.1 mL, 8.72 mmol) in DCM (10 mL) at 0° C. The resultant reaction mass was stirred at room temperature for 2 h, and diluted with DCM then washed with water followed by brine solution. The organic layer was dried over anhydrous sodium sulphate, concentrated under vacuum and crude compound was purified with silica column chromatography by eluting with 10%-30% hexane-ethyl acetate to afford the title compound (1 g, 53%). LCMS: m/z=336.1 (M-Boc+2).

The compounds listed in below Table-1 was prepared by procedure similar to the one described in Intermediate-2 with appropriate variations in reactants. The characterization data of the compounds are summarized herein the below table.

TABLE 1

| Intermediate No. | Structure | Characterization data |
|---|---|---|
| 3 | 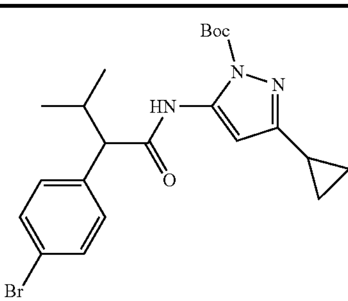 | $^1$HNMR (DMSO-d$_6$, 400 MHz): δ 10.15 (s, 1H), 7.55 (d, 2H), 7.35 (d, 2H), 6.33 (s, 1H), 3.54-3.51 (m, 1H), 2.30-2.20 (m, 1H), 1.84-1.78 (m, 1H), 1.42 (s, 9H), 0.98-0.96 (m, 3H), 0.88-0.86 (m, 2H), 0.67-0.64 (m, 5H). LCMS: m/z = 464.05 (M + H)$^+$. |
| 4 | 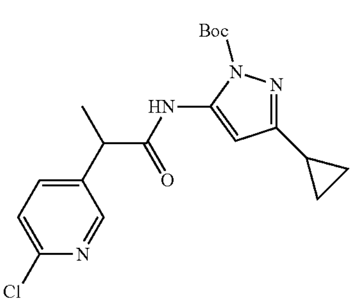 [SMILES: CC(C(=O)Nc1cc(C2CC2)nn1C(=O)OC(C)(C)C)c1ccc(Cl)nc1] | $^1$HNMR (CDCl3, 400 MHz): δ 10.36 (s, 1H), 8.37 (d, 1H), 7.28-7.09 (m, 1H), 7.34-7.31 (m, 1H), 6.37 (s, 1H), 3.77-3.69 (m, 1H), 1.99-1.93 (m, 1H), 1.63 (d, 3H), 1.53 (s, 9H), 0.96-0.91 (m, 2H), 0.95-0.70 (m, 2H). LCMS: m/z = 391.9 (M + H)$^+$. |

TABLE 1-continued

| Intermediate No. | Structure | Characterization data |
|---|---|---|
| 5 | 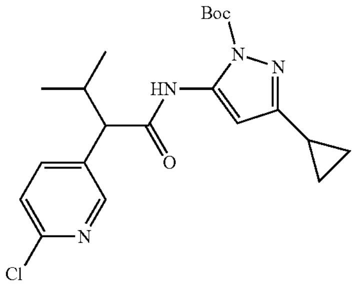 [SMILES: CC(C)C(C(=O)Nc1cc(C2CC2)nn1C(=O)OC(C)(C)C)c1ccc(Cl)nc1] | $^1$HNMR (CDCl3, 400 MHz): δ 10.41 (s, 1H), 8.34 (d, 1H), 7.84 (m, 1H), 7.30-7.26 (m, 1H), 6.39 (s, 1H), 3.06-3.02 (m, 1H), 2.44-2.36 (m, 1H), 1.98-1.92 (m, 1H), 1.54 (s, 9H), 1.12-0.98 (m, 3H), 0.88-0.86 (m, 2H), 0.75-0.70 (m, 5H). LCMS: m/z = 419.2 (M + H)$^+$. |
| 7 | 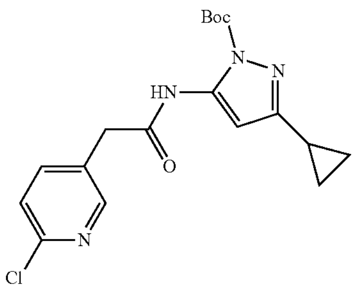 [SMILES: CC(C)(C)OC(=O)n1nc(C2CC2)cc1NC(=O)Cc1ccc(Cl)nc1] | $^1$HNMR (DMSO-d$_6$, 400 MHz): δ 10.20 (s, 1H), 8.34-8.33 (m, 1H), 7.81-7.78 (m, 1H), 7.51-7.48 (m, 1H), 6.31 (s, 1H), 3.89 (s, 2H), 1.90-1.85 (m, 1H), 1.56 (s, 9H), 0.93-0.86 (m, 2H), 0.68-0.63 (m, 2H). LCMS: m/z = 377.10 (M + H)$^+$. |

Intermediate-6: Synthesis of tert-butyl (S)-5-(2-(4-bromophenyl)propanamido)-3-cyclopropyl-1H-pyrazole-1-carboxylate

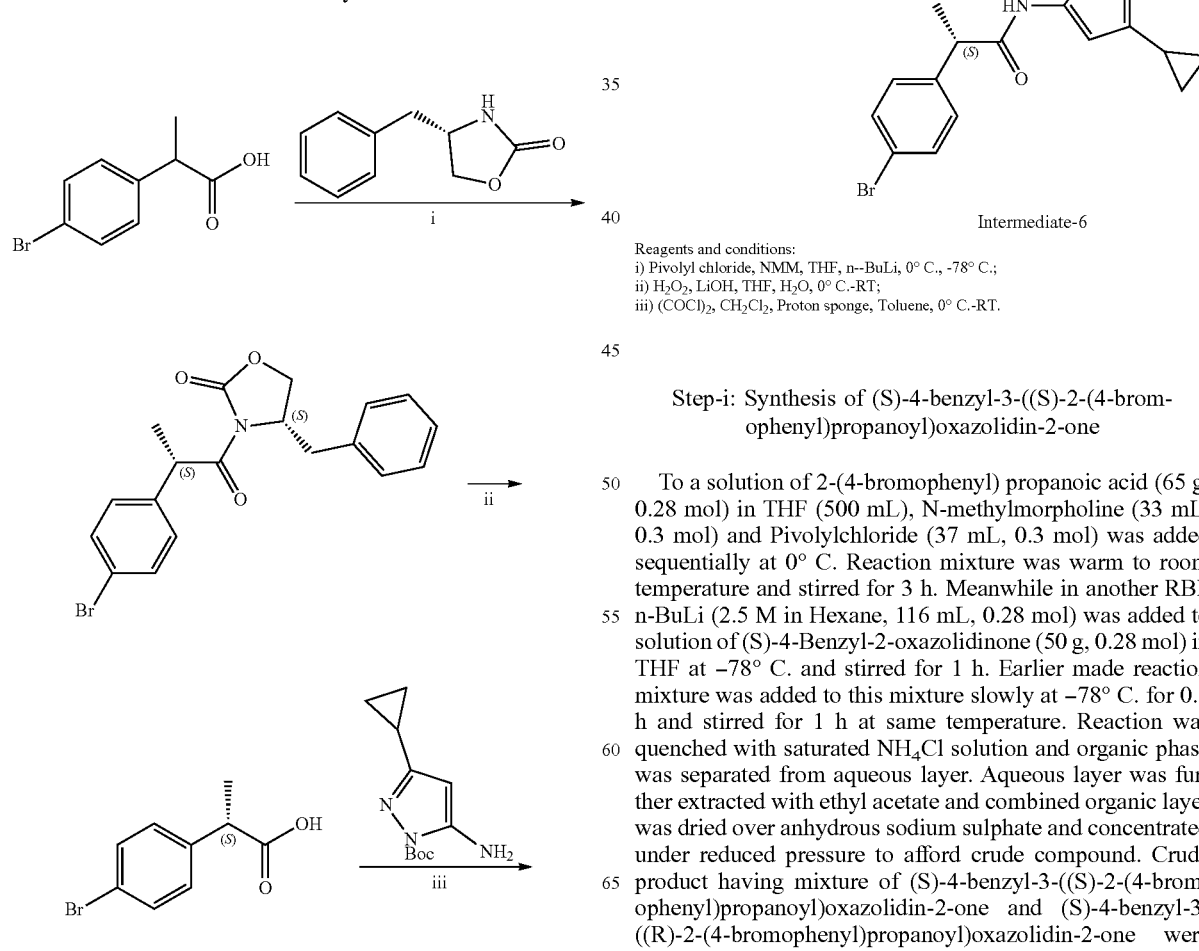

Reagents and conditions:
i) Pivolyl chloride, NMM, THF, n--BuLi, 0° C., -78° C.;
ii) H$_2$O$_2$, LiOH, THF, H$_2$O, 0° C.-RT;
iii) (COCl)$_2$, CH$_2$Cl$_2$, Proton sponge, Toluene, 0° C.-RT.

Step-i: Synthesis of (S)-4-benzyl-3-((S)-2-(4-bromophenyl)propanoyl)oxazolidin-2-one To a solution of 2-(4-bromophenyl) propanoic acid (65 g, 0.28 mol) in THF (500 mL), N-methylmorpholine (33 mL, 0.3 mol) and Pivolylchloride (37 mL, 0.3 mol) was added sequentially at 0° C. Reaction mixture was warm to room temperature and stirred for 3 h. Meanwhile in another RBF n-BuLi (2.5 M in Hexane, 116 mL, 0.28 mol) was added to solution of (S)-4-Benzyl-2-oxazolidinone (50 g, 0.28 mol) in THF at -78° C. and stirred for 1 h. Earlier made reaction mixture was added to this mixture slowly at -78° C. for 0.5 h and stirred for 1 h at same temperature. Reaction was quenched with saturated NH$_4$Cl solution and organic phase was separated from aqueous layer. Aqueous layer was further extracted with ethyl acetate and combined organic layer was dried over anhydrous sodium sulphate and concentrated under reduced pressure to afford crude compound. Crude product having mixture of (S)-4-benzyl-3-((S)-2-(4-bromophenyl)propanoyl)oxazolidin-2-one and (S)-4-benzyl-3-((R)-2-(4-bromophenyl)propanoyl)oxazolidin-2-one were purified with silica column chromatography by eluting with 97%-30% hexane-ethyl acetate to isolate desired product (S)-4-benzyl-3-((S)-2-(4-bromophenyl)propanoyl)oxazolidin-2-one (42 g, 38.5%), LCMS: m/z=386 (M−H)⁻, Chiral HPLC: 98.84%, rt: 7.54 min.

Step-ii: Synthesis of (S)-2-(4-bromophenyl)propanoic acid

LiOH (9.3 g, 0.22 mol) was dissolved in water (150 mL) and added to solution of (S)-4-benzyl-3-((S)-2-(4-bromophenyl)propanoyl)oxazolidin-2-one (42 g, 0.11 mol) in THF (250 mL) and H$_2$O$_2$(30% w/v solution, 40 mL, 0.33 mol) at 0° C. Resultant mixture was brought to room temperature and stir for 2 h. Reaction mass was quenched with saturated Na$_2$SO$_3$ solution and diluted with ether. Organic phase was separated from aqueous layer and washed with ethyl acetate twice. Separated aqueous layer was acidified using 2N HCl and extracted with DCM twice, washed with brine, dried over anhydrous sodium sulphate and concentrated under vacuum to get crude compound. Crude was further purified by using ethylacetate:hexane (3:97) mixture as mobile phase to afford pure title compound (17 g, 67%). ¹HNMR (DMSO-d$_6$, 400 MHz): δ 12.4 (s, 1H), 7.53-7.49 (m, 2H), 7.27-7.22 (m, 2H), 3.71-3.64 (m, 1H), 1.33 (d, 3H), LCMS: m/z=228.9 (M−H)⁺, HPLC: 99.60%, rt: 6.51 min, Chiral HPLC; 99.33%, rt: 8.91 min.

Step-iii: Synthesis of tert-butyl (S)-5-(2-(4-bromophenyl)propanamido)-3-cyclopropyl-1H-pyrazole-1-carboxylate (S)-2-(4-bromophenyl) propanoic acid (16.5 g, 73 mmol) was dissolved in dry DCM (100 mL) and added oxalyl chloride (11.1 g, 88 mmol) at 0° C. followed by dropwise addition of catalytic amount of DMF and stirred for 30 min at the same temperature. Reaction mass was warm to room temperature and stirred for another 2 h. Excess of solvent and oxalyl chloride was evaporated under normal reduce pressure. Residue was re-dissolved in toluene and added to the solution of tert-butyl 5-amino-3-cyclopropyl-1H-pyrazole-1-carboxylate (16.5 g, 73.6 mmol) and 1,8-Bis(dimethylamino)naphthalene (Proton sponge) (15.6 g, 73 mmol) in toluene (250 mL) at 0° C. Reaction mixture was stirred for 2 h then solvent was removed under reduce pressure and residue was dissolved in DCM, washed with water, dried over anhydrous sodium sulphate and evaporated to get brown residue. Crude compound was further purified by silica column chromatography (10% of Ethyl acetate in hexane) to get the pure compound (15 g, 47%). LCMS: m/z=434.05 (M+H)⁺, HPLC: 96.10%, rt: 5.44 min, Chiral HPLC; 98.84%, rt: 6.64 min.

Intermediate-7: Synthesis of tert-butyl 4-(4-(1-methoxy-1-oxopropan-2-yl)phenyl)piperazine-1-carboxylate

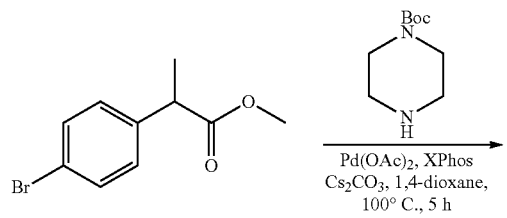

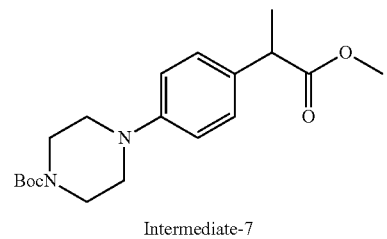

Intermediate-7

To a degassed solution of methyl 2-(4-bromophenyl) propanoate (5 g, 20.5 mmol) and tert-butyl piperazine-1-carboxylate (3.83 g, 20.5 mmol) in 1,4-Dioxane (50 mL) was added Cs$_2$CO$_3$ (13.37 g, 41.16 mmol). The reaction mass was allowed to stir for 10 min with degassing and added Xphos (1.95 g, 4.1 mmol) followed by Pd(OAc)$_2$ (0.46 g, 2.05 mmol), heated the reaction mass for 5 h at 100° C. in a sealed tube. Reaction mixture cooled to RT and filtered on celite bed, layers were separated for filtrate and re-extracted aqueous layer with ethyl acetate. The combined organic layer was evaporated to dryness and crude material was purified by silica column chromatography by eluting with 30%-50% ethyl acetate in hexane to get desired pure compound (6 g, 83%). LCMS: m/z=349.1 (M+H)⁺.

The present invention is further exemplified, but not limited, by the following examples that illustrate the preparation of compounds according to the invention.

Example 1

Synthesis of 2-(4-(1-acryloyl-1,2,3,6-tetrahydropyridin-4-yl)phenyl)-N-(5-cyclopropyl-1H-pyrazol-3-yl) propanamide. (Compound 1)

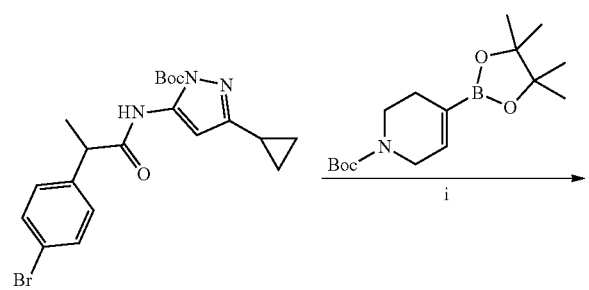

Intermediate-2

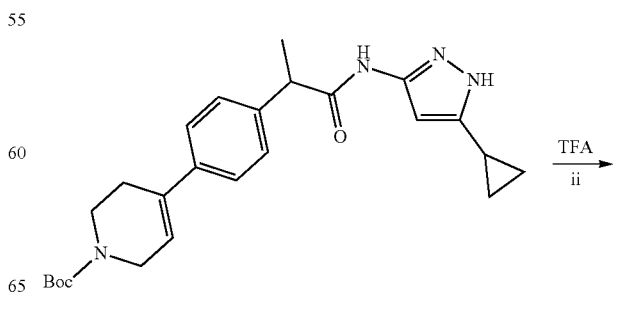

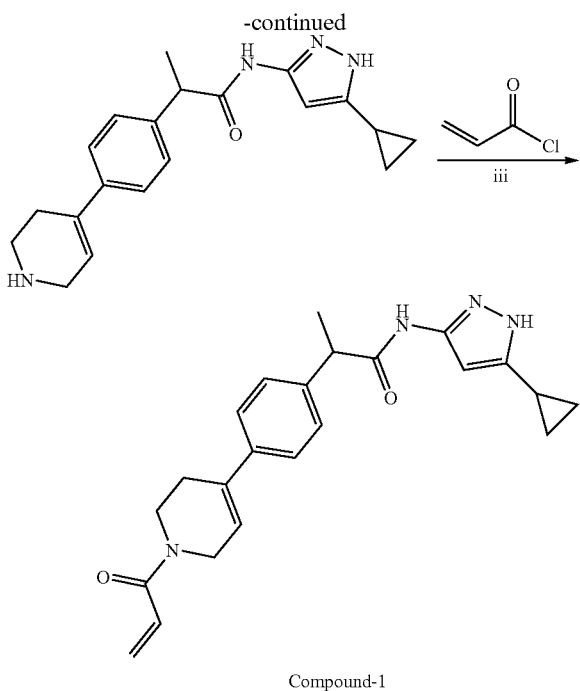

Compound-1

Reagents and conditions:
i) Cs₂CO₃, Pd(PPh₃)₄, 1,4-Dioxane-Water, 100° C., 4 h;
ii) TFA, DCM, RT, 3 h;
iii) DIPEA, Acetonitrile-water, 0° C.-RT, 0.5 h.

Step i: Synthesis of tert-butyl 4-(4-(1-((5-cyclopropyl-1H-pyrazol-3-yl)amino)-1-oxopropan-2-yl)phenyl)-3,6-dihydropyridine-1(2H)-carboxylate To a degas solution of tert-butyl 5-(2-(4-bromophenyl)propanamido)-3-cyclopropyl-1H-pyrazole-1-carboxylate (1.5 g, 3.45 mmol) (Intermediate-2) in 1,4-dioxane (40 mL), Cesium carbonate (2.25 g, 6.9 mmol) dissolved in water (2.0 M solution) and tert-butyl 4-(4,4,5,5-tetramethyl-1,3,2-dioxaborolan-2-yl)-3,6-dihydropyridine-1(2H)-carboxylate (1.5 g, 4.8 mmol) were added and resultant solution was degassed for 10 min. Pd(PPh₃)₄ (0.2 g, 5 mol %) was added and mixture was heated at 100° C. for 4 h. Reaction mass filtered through celite and organic layer was separated, washed with brine and dried over anhydrous sodium sulphate to yield crude title compound. Crude was further purified using flash chromatography using ethylacetate: hexane (1:1) mixture as eluent to afford title compound (1.25 g, 83%), LCMS: m/z=437.1 (M+H)⁺.

Step ii: Synthesis of N-(5-cyclopropyl-1H-pyrazol-3-yl)-2-(4-(1,2,3,6-tetrahydropyridin-4-yl)phenyl)propanamide To a solution of tert-butyl 4-(4-(1-((5-cyclopropyl-1H-pyrazol-3-yl)amino)-1-oxopropan-2-yl)phenyl)-3,6-dihydropyridine-1(2H)-carboxylate (0.7 g, 1.6 mmol) in DCM (10 mL), Triflouroaceticacid (1.0 mL) was added at 0° C. Resultant mixture was slowly brought to room temperature and stir for 3 h. Excess of solvent was removed under reduce pressure and residue was suspended in saturated sodium bicarbonate solution. Aqueous layer was extracted thrice with ethyl acetate and combined organic layer was dried over sodium sulphate and concentrated to afford title compound (0.53 g, 99%), LCMS: m/z=337.1 (M+H)⁺.

Step iii: Synthesis of 2-(4-(1-acryloyl-1,2,3,6-tetrahydropyridin-4-yl)phenyl)-N-(5-cyclopropyl-1H-pyrazol-3-yl)propanamide N-(5-cyclopropyl-1H-pyrazol-3-yl)-2-(4-(1,2,3,6-tetrahydropyridin-4-yl)phenyl) propanamide (0.2 g, 0.6 mmol) was dissolved in mixture of 10 mL ACN:H₂O (9:1). DIPEA (0.2 mL, 1.55 mmol) and acryloyl chloride (0.05 g, 0.6 mmol) were added to above solution at 0° C. and resultant mixture was stirred for 30 min. Reaction mass was quenched with water and diluted with DCM. Organic layer was separated and aqueous layer was further extracted with DCM. Combined organic layer was dried over sodium sulphate and concentrated to afford crude compound. Crude was further purified using flash chromatography using MeOH:DCM (2:98) mixture as eluent to afford title compound (0.1 g, 42%). ¹HNMR (DMSO-d₆, 400 MHz): δ 12.1 (s, 1H), 10.39 (s, 1H), 7.39-7.31 (m, 4H), 6.92-6.72 (m, 1H), 6.15-6.12 (m, 3H), 5.72-5.68 (m, 1H), 4.24-4.15 (m, 2H), 3.83-3.70 (m, 3H), 2.43-2.41 (m, 2H), 1.84-1.78 (m, 1H), 1.34 (d, 3H), 0.88-0.86 (m, 2H), 0.62-0.58 (m, 2H). LCMS: m/z=391.3 (M+H)⁺; HPLC: 95.62%, rt: 6.87 min.

The compounds listed in below Table-2 were prepared by procedure similar to the one described in Example 1 with appropriate variations in reactants, quantities of reagents, protections and de-protections, solvents and reaction conditions. The characterization data of the compounds are summarized herein the below table.

TABLE 2

| Comp. No. | Structure | Characterization data |
| --- | --- | --- |
| 2 | <img structure of (S)-enantiomer> | ¹HNMR (DMSO-d₆, 400 MHz): δ 12.1 (s, 1H), 10.39 (s, 1H), 7.39-7.31 (m, 4H), 6.92-6.72 (m, 1H), 6.15-6.12 (m, 3H), 5.72-5.68 (m, 1H), 4.24-4.15 (m, 2H), 3.83-3.70 (m, 3H), 2.43-2.41 (m, 2H), 1.84-1.78 (m, 1H), 1.34 (d, 3H), 0.88-0.86 (m, 2H), 0.62-0.58 (m, 2H). LCMS: m/z = 391.3 (M + H)⁺; HPLC: 98.85%, rt: 6.88 min.; Chiral HPLC: 99.05%, rt: 6.04 min. |

TABLE 2-continued

| Comp. No. | Structure | Characterization data |
|---|---|---|
| 3 | 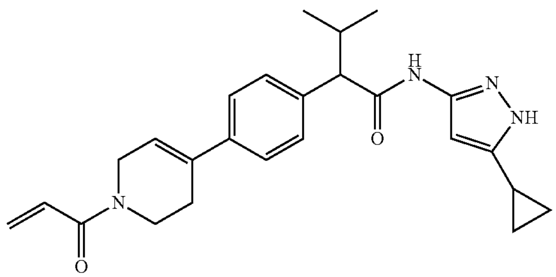 [SMILES: C=CC(=O)N1CC=C(c2ccc(C(C(=O)Nc3cc(C4CC4)[nH]n3)C(C)C)cc2)CC1] | $^1$HNMR (DMSO-d$_6$, 400 MHz): δ 12.1 (s, 1H), 10.41 (s, 1H), 7.37-7.32 (m, 4H), 6.95-6.80 (m, 1H), 6.15-6.12 (m, 3H), 5.71-5.68 (m, 1H), 4.25-4.15 (m, 2H), 3.75-3.72 (m, 3H), 3.28-3.25 (m, 2H), 2.51-2.49 (m, 1H), 1.84-1.80 (m, 1H), 0.95-0.93 (m, 3H), 0.86-0.84 (m, 2H), 0.63-0.60 (m, 5H). LCMS: m/z = 419.65 (M + H)$^+$; HPLC: 95.42%, rt: 11.24 min. |
| 4 | 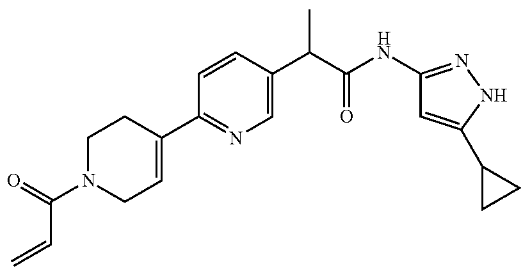 [SMILES: C=CC(=O)N1CC=C(c2ccc(C(C)C(=O)Nc3cc(C4CC4)[nH]n3)cn2)CC1] | $^1$HNMR (DMSO-d$_6$, 400 MHz): δ 12.1 (s, 1H), 10.51 (s, 1H), 8.50 (s, 1H), 7.75-7.70 (m, 1H), 7.52-7.51 (m, 1H), 6.92-6.72 (m, 1H), 6.66-6.11 (m, 1H), 6.15-6.12 (m, 3H), 5.72-5.68 (m, 1H), 4.41-4.21 (m, 2H), 3.90-3.80 (m, 1H), 3.78-3.62 (m, 1H), 2.53-2.51 (m, 2H), 1.84-1.78 (m, 1H), 1.39 (d, 3H), 0.88-0.86 (m, 2H), 0.62-0.60 (m, 2H). LCMS: m/z = 392.35 (M + H)$^+$; HPLC: 97.18%, rt: 6.02 min. |
| 5 | 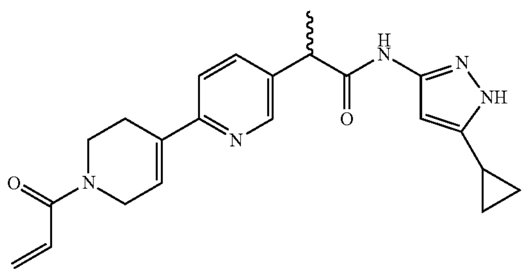 [SMILES: C=CC(=O)N1CC=C(c2ccc(C(C)C(=O)Nc3cc(C4CC4)[nH]n3)cn2)CC1] | $^1$HNMR (DMSO-d$_6$, 400 MHz): δ 12.1 (s, 1H), 10.51 (s, 1H), 8.50 (s, 1H), 7.75-7.70 (m, 1H), 7.52-7.51 (m, 1H), 6.92-6.72 (m, 1H), 6.66-6.11 (m, 1H), 6.15-6.12 (m, 3H), 5.72-5.68 (m, 1H), 4.41-4.21 (m, 2H), 3.90-3.80 (m, 1H), 3.78-3.62 (m, 1H), 2.53-2.51 (m, 2H), 1.84-1.78 (m, 1H), 1.39 (d, 3H), 0.88-0.86 (m, 2H), 0.62-0.60 (m, 2H). LCMS: m/z = 392.35 (M + H)$^+$; HPLC: 90%, rt: 7.88 min.; Chiral HPLC: 90.01%, rt: 5.48 min. |
| 6 | 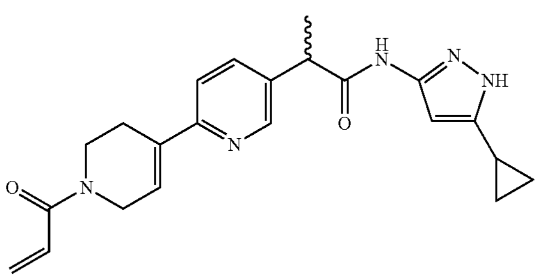 [SMILES: C=CC(=O)N1CC=C(c2ccc(C(C)C(=O)Nc3cc(C4CC4)[nH]n3)cn2)CC1] | $^1$HNMR (DMSO-d$_6$, 400 MHz): δ 12.1 (s, 1H), 10.51 (s, 1H), 8.50 (s, 1H), 7.75-7.70 (m, 1H), 7.52-7.51 (m, 1H), 6.92-6.72 (m, 1H), 6.66-6.11 (m, 1H), 6.15-6.12 (m, 3H), 5.72-5.68 (m, 1H), 4.41-4.21 (m, 2H), 3.90-3.80 (m, 1H), 3.78-3.62 (m, 1H), 2.53-2.51 (m, 2H), 1.84-1.78 (m, 1H), 1.39 (d, 3H), 0.88-0.86 (m, 2H), 0.62-0.60 (m, 2H). LCMS: m/z = 392.35 (M + H)$^+$; HPLC: 95.38%, rt: 5.03 min.; Chiral HPLC: 94.01%, rt: 10.22 min. |
| 7 | 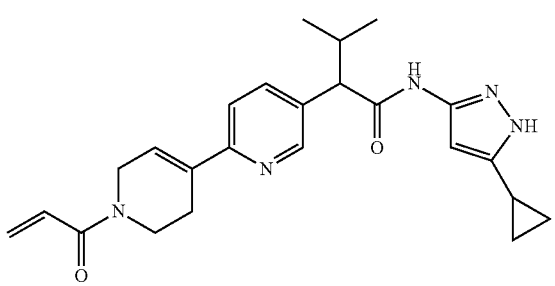 [SMILES: C=CC(=O)N1CC=C(c2ccc(C(C(=O)Nc3cc(C4CC4)[nH]n3)C(C)C)cn2)CC1] | $^1$HNMR (CDCl$_3$, 400 MHz): δ 8.45 (s, 1H), 7.93-7.91 (m, 1H), 7.82-7.78 (m, 1H), 7.34-7.31 (m, 1H), 6.70-6.55 (m, 2H), 6.34-6.25 (m, 1H), 5.50-5.48 (m, 1H), 4.33-423 (m, 2H), 3.90-3.88 (m, 1H), 3.78-3.62 (m, 1H), 2.95-2.93 (m, 1H), 2.72-2.62 (m, 2H), 1.88-1.84 (m, 1H), 1.08-1.07 (m, 3H), 0.93-0.91 (m, 2H), 0.73-0.69 (m, 5H). LCMS: m/z = 420.0 (M + H)$^+$; HPLC: 98.57%, rt: 5.74 min. |

TABLE 2-continued

| Comp. No. | Structure | Characterization data |
|---|---|---|
| 8 | 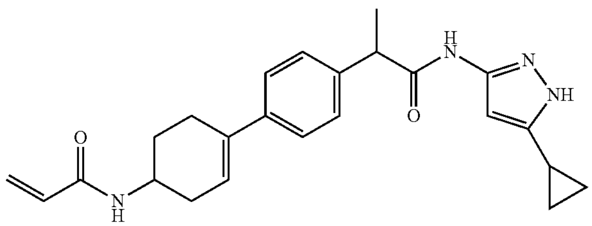 [SMILES: C=CC(=O)NC1CC=C(c2ccc(C(C)C(=O)Nc3cc(C4CC4)[nH]n3)cc2)CC1] | ¹HNMR (DMSO-d₆, 400 MHz): δ 12.1 (s, 1H), 10.41 (s, 1H), 8.11 (d, 1H), 7.36-7.30 (m, 4H), 6.27-6.24 (m, 1H), 6.14-6.05 (m, 3H), 5.60 (d, 1H), 3.92-3.85 (m, 1H), 3.83-3.80 (m, 1H), 2.51-2.39 (m, 3H), 2.10-2.06 (m, 1H), 1.95-1.92 (m, 1H), 1.82-1.80 (m, 1H), 1.63-1.60 (m, 1H), 1.36 (d, 3H), 0.89-0.87 (m, 2H), 0.62-0.61 (m, 2H). LCMS: m/z = 405.4 (M + H)⁺; HPLC: 99.32%, rt: 6.90 min. |
| 9 | 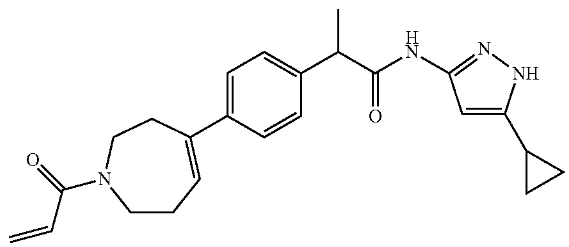 [SMILES: C=CC(=O)N1CCC=C(c2ccc(C(C)C(=O)Nc3cc(C4CC4)[nH]n3)cc2)CC1] | ¹HNMR (DMSO-d₆, 400 MHz): δ 12.1 (s, 1H), 10.37 (s, 1H), 7.30-7.24 (m, 4H), 6.79-6.76 (m, 1H), 6.12-6.06 (m, 3H), 5.66 (m, 1H), 4.18-4.13 (m, 2H), 3.81-3.69 (m, 4H), 2.66-2.57 (m, 1H), 1.86-1.80 (m, 3H), 1.34 (d, 3H), 0.89-0.87 (m, 2H), 0.62-0.61 (m, 2H). LCMS: m/z = 405.1 (M + H)⁺; HPLC: 94.63%, rt: 10.31 min. |
| 29 | 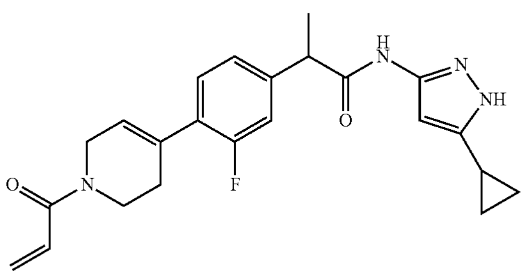 [SMILES: C=CC(=O)N1CC=C(c2ccc(C(C)C(=O)Nc3cc(C4CC4)[nH]n3)cc2F)CC1] | 1HNMR (DMSO-d6, 400 MHz): δ 12.10 (s, 1H), 10.44 (s, 1H), 7.30-7.28 (m, 1H), 7.17-7.14 (m, 2H), 6.90-6.50 (m, 2H), 6.15-6.12 (m, 1H), 5.95-5.94 (m, 1H), 5.71-5.69 (m, 1H), 4.25-4.15 (m, 2H), 3.85-3.83 (m, 1H), 3.75-3.71 (m, 2H), 2.40-2.32 (m, 2H), 1.81-1.80 (m, 1H), 1.36-1.34 (m, 3H), 0.89-0.86 (m, 2H), 0.62-0.61 (m, 2H). LCMS: m/z = 408.90 (M + H)+; HPLC: 94.37%, rt: 6.30 min. |
| 34 | 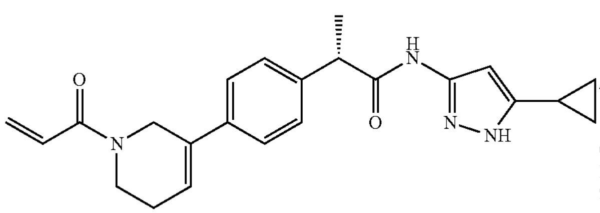 | ¹HNMR (CDCl₃, 400 MHz): δ 8.29-8.15 (d, 1H), 7.33-7.31 (m, 4H), 6.67-6.58 (m, 1H), 6.33-6.27 (m, 3H), 5.72-5.68 (m, 1H), 4.46-4.34 (m, 2H), 3.80-3.77 (m, 1H), 3.68-3.64 (m, 2H), 2.38-2.36 (m, 2H), 1.80-1.77 (m, 1H), 1.55 (d, 3H), 0.91-0.89 (m, 2H), 0.69-0.67 (m, 2H). LCMS: m/z = 391.60 (M + H)⁺; HPLC: 97.52%, rt: 6.88 min.; Chiral HPLC: 96.88%, rt: 7.96 min. |
| 35 | 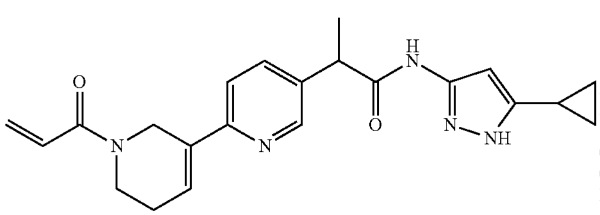 [SMILES: C=CC(=O)N1CCC=C(c2ccc(C(C)C(=O)Nc3cc(C4CC4)[nH]n3)cn2)C1] | ¹HNMR (DMSO-d₆, 400 MHz): δ 12.1 (s, 1H), 10.41 (s, 1H), 8.50 (s, 1H), 7.74 (d, 1H), 6.95-6.80 (m, 2H), 6.15-6.12 (m, 2H), 5.81-5.68 (m, 1H), 4.61-4.50 (m, 2H), 3.89-3.87 (m, 2H), 3.68-3.66 (m, 2H), 2.41-2.30 (m, 2H), 1.88-1.81 (m, 1H), 1.39 (d, 3H), 0.89-0.87 (m, 2H), 0.86-0.84 (m, 2H), 0.63-0.60 (m, 5H). LCMS: m/z = 392.35 (M + H)⁺; HPLC: 95.61%, rt: 9.07 min. |
| 36 | 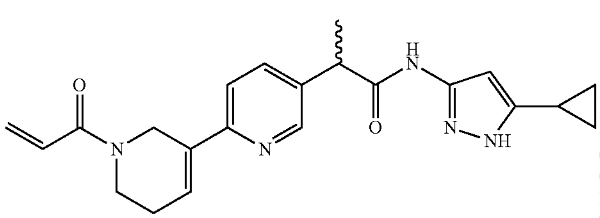 [SMILES: C=CC(=O)N1CCC=C(c2ccc(C(C)C(=O)Nc3cc(C4CC4)[nH]n3)cn2)C1] | ¹HNMR (DMSO-d₆, 400 MHz): δ 12.1 (s, 1H), 10.41 (s, 1H), 8.50 (s, 1H), 7.74 (d, 1H), 6.95-6.80 (m, 2H), 6.15-6.12 (m, 2H), 5.81-5.68 (m, 1H), 4.61-4.50 (m, 2H), 3.89-3.87 (m, 2H), 3.68-3.66 (m, 2H), 2.41-2.30 (m, 2H), 1.88-1.81 (m, 1H), 1.39 (d, 3H), 0.89-0.87 (m, 2H), 0.86-0.84 (m, 2H), 0.63-0.60 (m, 5H). LCMS: m/z = 392.35 (M + H)⁺; HPLC: 96.62%, rt: 9.07 min, Chiral HPLC: 99.06%, rt; 17.5 min. |

TABLE 2-continued

| Comp. No. | Structure | Characterization data |
|---|---|---|
| 37 | 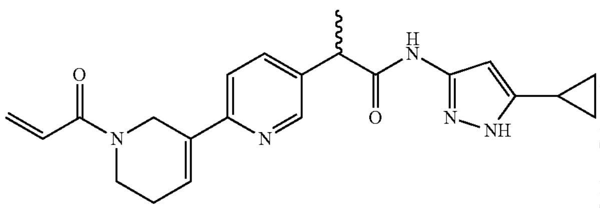 [SMILES: C=CC(=O)N1CCC=C(c2ccc(C(C)C(=O)Nc3cc(C4CC4)[nH]n3)cn2)C1] | ¹HNMR (DMSO-d₆, 400 MHz): δ 12.1 (s, 1H), 10.41 (s, 1H), 8.50 (s, 1H), 7.74 (d, 1H), 6.95-6.80 (m, 2H), 6.15-6.12 (m, 2H), 5.81-5.68 (m, 1H), 4.61-4.50 (m, 2H), 3.89-3.87 (m, 2H), 3.68-3.66 (m, 2H), 2.41-2.30 (m, 2H), 1.88-1.81 (m, 1H), 1.39 (d, 3H), 0.89-0.87 (m, 2H), 0.86-0.84 (m, 2H), 0.63-0.60 (m, 5H). LCMS: m/z = 392.35 (M + H)⁺; HPLC: 99.84%, rt: 9.07 min, Chiral HPLC: 99.33%, rt: 22.57 min. |
| 38 | 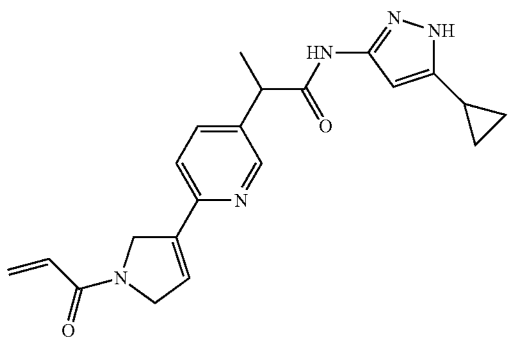 [SMILES: C=CC(=O)N1CC=C(c2ccc(C(C)C(=O)Nc3cc(C4CC4)[nH]n3)cn2)C1] | ¹HNMR (CDCl₃, 400 MHz): 9.49-9.31 (m, 1H), 8.47-8.39 (m, 1H), 7.69-7.64 (m, 1H), 7.39-7.22 (m, 1H), 6.58-6.42 (m, 3H), 6.32-6.30 (m, 1H), 6.22-6.20 (m, 1H), 5.77-5.73 (m, 1H), 4.72-4.68 (m, 2H), 4.54-4.52 (m, 1H), 3.76-3.69 (m, 1H), 1.83-1.77 (m, 1H), 1.52 (d, 3H), 0.92-0.87 (m, 2H), 0.71-0.68 (m, 2H). LCMS: m/z = 378.12 (M + H)⁺; HPLC: 96.64%, rt: 6.23 min. |
| 39 | 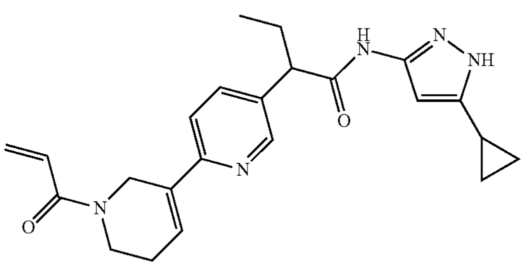 [SMILES: C=CC(=O)N1CCC=C(c2ccc(C(CC)C(=O)Nc3cc(C4CC4)[nH]n3)cn2)C1] | ¹HNMR (CDCl₃, 400 MHz): δ 8.47-8.45 (m, 1H), 7.88-7.85 (m, 1H), 7.73-7.71 (m, 1H), 7.52-7.45 (m, 1H), 6.74-6.61 (m, 2H), 6.34-6.31 (m, 2H), 5.73-5.70 (m, 1H), 4.62-4.58 (m, 2H), 3.83-3.80 (m, 1H), 3.70-3.67 (m, 1H), 3.36-3.33 (m, 1H), 2.42-2.38 (m, 1H), 2.26-2.17 (m, 1H), 1.88-1.76 (m, 2H), 0.93-0.91 (m, 5H), 0.73-0.69 (m, 2H). LCMS: m/z = 406.4 (M + H)⁺; HPLC: 99.44%, rt: 6.66 min. |
| 40 | 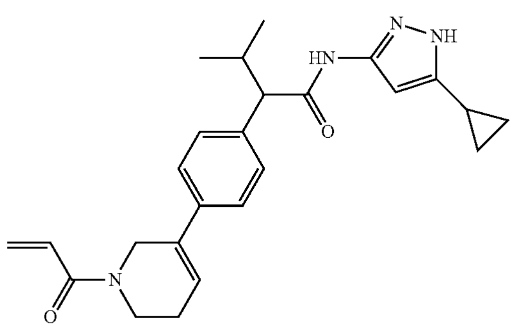 [SMILES: C=CC(=O)N1CCC=C(c2ccc(C(C(=O)Nc3cc(C4CC4)[nH]n3)C(C)C)cc2)C1] | ¹HNMR (DMSO-d₆, 400 MHz): δ 12.1 (s, 1H), 10.41 (s, 1H), 7.86-7.38 (m, 4H), 7.07-6.85 (m, 2H), 6.29-6.26 (m, 1H), 6.15-6.11 (m, 2H), 5.76-5.66 (m, 1H), 4.54-4.21 (m, 2H), 3.83-3.68 (m, 2H), 3.34-3.26 (m, 1H), 2.41-2.31 (m, 2H), 1.82-1.80 (m, 1H), 0.96-0.94 (m, 3H), 0.93-0.87 (m, 2H), 0.85-0.61 (m, 5H). LCMS: m/z = 418.19 (M + H)⁺; HPLC: 95.12%, rt: 12.60 min. |
| 42 | 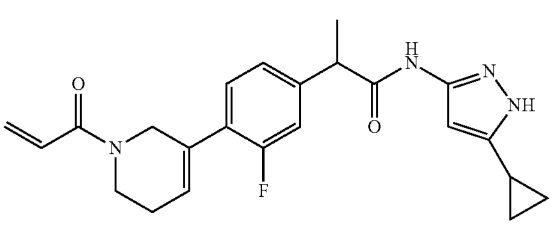 [SMILES: C=CC(=O)N1CCC=C(c2ccc(C(C)C(=O)Nc3cc(C4CC4)[nH]n3)cc2F)C1] | 1HNMR (DMSO-d6, 400 MHz): 12.05 (s, 1H), 10.45 (s, 1H), 7.33-7.30 (m, 1H), 7.20-7.16 (m, 2H), 6.87-6.83 (m, 1H), 6.14-6.06 (m, 3H), 5.75-5.65 (m, 1H), 4.31 (s, 2H), 3.87-3.85 (m, 1H), 3.70-3.67 (m, 2H), 2.31-2.27 (m, 2H), 1.84-1.82 (m, 1H), 1.38-1.35 (m, 3H), 0.90-0.88 (m, 2H), 0.65-0.62 (m, 2H). LCMS: m/z = 408.90 (M + H)+; HPLC: 95.80%, rt: 11.80 min. |

TABLE 2-continued

| Comp. No. | Structure | Characterization data |
|---|---|---|
| 43 | 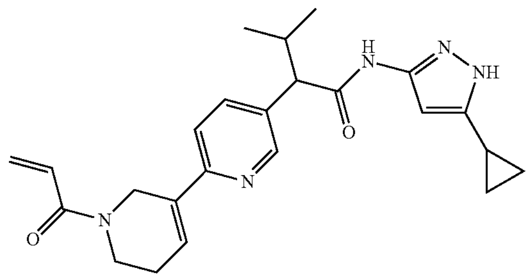 [SMILES: C=CC(=O)N1CCC=C(c2ccc(C(C(=O)Nc3cc(C4CC4)[nH]n3)C(C)C)cn2)C1] | 1HNMR (DMSO-d6, 400 MHz): 12.40 (s, 1H), 10.53 (s, 1H), 8.46 (s, 1H), 7.77-7.75 (m, 1H), 7.65-7.61 (m, 1H), 6.90-6.86 (m, 1H), 6.79-6.74 (m, 1H), 6.14-6.09 (m, 2H), 5.70-5.68 (m, 1H), 4.53-4.49 (m, 2H), 3.69-3.65 (m, 2H), 2.47-3.30 (m, 4H), 1.81-1.80 (m, 1H), 0.97-0.96 (m, 3H), 0.88-0.86 (m, 2H). 0.64-0.60 (m, 5H) LCMS: m/z = 420.20 (M + H)+; HPLC: 98.30%, rt: 6.91 min. |
| 44 | (Isomer-1 of compd-29) | 1HNMR (DMSO-d6, 400 MHz): 12.10 (s, 1H), 10.44 (s, 1H), 7.30-7.28 (m, 1H), 7.17-7.14 (m, 2H), 6.90-6.50 (m, 2H), 6.15-6.12 (m, 1H), 5.95-5.94 (m, 1H), 5.71-5.69 (m, 1H), 4.25-4.15 (m, 2H), 3.85-3.83 (m, 1H), 3.75-3.71 (m, 2H), 2.40-2.32 (m, 2H), 1.81-1.80 (m, 1H), 1.36-1.34 (m, 3H), 0.89-0.86 (m, 2H), 0.62-0.61 (m, 2H). LCMS: m/z = 408.90 (M + H)+; HPLC: 96.47%, rt: 6.31 min; Chiral HPLC: 99.26%, rt: 7.95 min. |
| 45 | (Isomer-2 of compd-29) | 1HNMR (DMSO-d6, 400 MHz): 12.10 (s, 1H), 10.44 (s, 1H), 7.30-7.28 (m, 1H), 7.17-7.14 (m, 2H), 6.90-6.50 (m, 2H), 6.15-6.12 (m, 1H), 5.95-5.94 (m, 1H), 5.71-5.69 (m, 1H), 4.25-4.15 (m, 2H), 3.85-3.83 (m, 1H), 3.75-3.71 (m, 2H), 2.40-2.32 (m, 2H), 1.81-1.80 (m, 1H), 1.36-1.34 (m, 3H), 0.89-0.86 (m, 2H), 0.62-0.61 (m, 2H). LCMS: m/z = 408.90 (M + H)+; HPLC: 98.34%, rt: 6.33 min; Chiral HPLC: 98.35%, rt: 9.59 min. |
| 46 | (Isomer-1 of compd-38) | $^1$HNMR (CDCl$_3$, 400 MHz): 9.49-9.31 (m, 1H), 8 47-8.39 (m, 1H), 7.69-7.64 (m, 1H), 7.39-7.22 (m, 1H), 6.58-6.42 (m, 3H), 6.32-6.30 (m, 1H), 6.22-6.20 (m, 1H), 5.77-5.73 (m, 1H), 4.72-4.68 (m, 2H), 4.54-4.52 (m, 1H), 3.76-3.69 (m, 1H), 1.83-1.77 (m, 1H), 1.52 (d, 3H), 0.92-0.87 (m, 2H). 0.71-0.68 (m, 2H). LCMS: m/z = 378.12 (M + H)$^+$; HPLC: 96.64%, rt: 6.20 min, Chiral HPLC: 98.16%, rt: 7.76 min. |
| 47 | (Isomer-2 of compd-38) | $^1$HNMR (CDCl$_3$, 400 MHz): 9.49-9.31 (m, 1H), 8.47-8.39 (m, 1H), 7.69-7.64 (m, 1H), 7.39-7.22 (m, 1H), 6.58-6.42 (m, 3H), 6.32-6.30 (m, 1H), 6.22-6.20 (m, 1H), 5.77-5.73 (m, 1H), 4.72-4.68 (m, 2H), 4.54-4.52 (m, 1H), 3.76-3.69 (m, 1H), 1.83-1.77 (m, 1H), 1.52 (d, 3H), 0.92-0.87 (m, 2H), 0.71-0.68 (m, 2H). LCMS: m/z = 378.12 (M + H)$^+$; HPLC: 96.64%, rt: 6.21 min, Chiral HPLC: 98.00%, rt: 8.84 min. |

TABLE 2-continued

| Comp. No. | Structure | Characterization data |
|---|---|---|
| 49 | 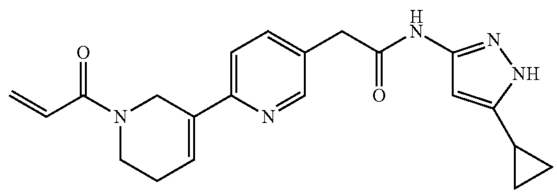 | $^1$HNMR (DMSO-d$_6$, 400 MHz): δ 12.06 (s, 1H), 10.56 (s, 1H), 8.44 (s, 1H), 7.70-7.67 (m, 1H), 7.64-7.59 (m, 1H), 6.88-6.74 (m, 2H), 6.21-6.06 (m, 2H), 5.76-5.68 (m, 1H), 4.53-4.50 (m, 2H), 3.71-3.66 (m, 2H), 3.61 (s, 2H), 2.35-2.32 (m, 2H), 1.84-1.80 (m, 1H), 0.87-0.86 (m, 2H), 0.64-0.60 (m, 2H). LCMS: m/z = 392.30 (M + H)$^+$; HPLC: 97.83%, rt: 5.65 min. |
| 51 | 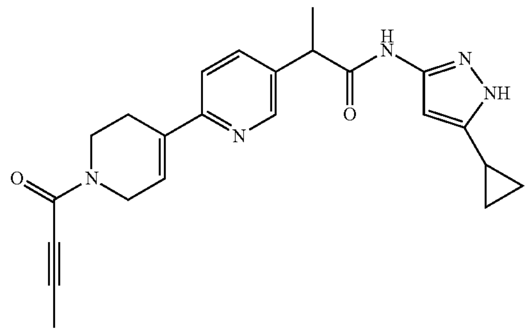 [SMILES: CC#CC(=O)N1CC=C(c2ccc(C(C)C(=O)Nc3cc(C4CC4)[nH]n3)cn2)CC1] | $^1$HNMR (CDCl$_3$, 400 MHz): δ 8.50 (s, 1H), 7.75-7.65 (m, 2H), 7.38-7.30 (m, 1H), 6.61-7.55 (m, 2H), 5.71-5.82 (m, 1H), 4.45-4.41 (m, 1H), 4.38-4.32 (m, 1H), 3.94-3.91 (m, 1H), 3.85-3.80 (m, 1H), 3.65-3.60 (m, 1H), 2.81-2.61 (m, 2H), 2.04-2.02 (m, 3H), 1.85-1.72 (m, 1H), 1.57 (s, 3H), 0.96-0.93 (m, 2H), 0.72-0.71 (m, 2H). LCMS: m/z = 404.15 (M + H)$^+$; HPLC: 97.21%, rt: 6.73 min. |
| 52 | 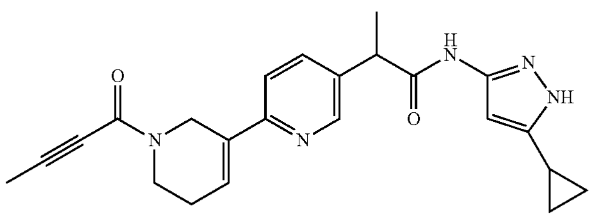 [SMILES: CC#CC(=O)N1CCC=C(c2ccc(C(C)C(=O)Nc3cc(C4CC4)[nH]n3)cn2)C1] | $^1$HNMR (CDCl$_3$, 400 MHz): δ 8.55-8.45 (m, 1H), 8.21-8.13 (m, 1H), 7.98-7.95 (m, 1H), 7.71-7.65 (m, 1H), 7.46-7.35 (m, 1H), 6.75-6.60 (m, 1H), 6.32-6.20 (m, 1H), 4.74-4.72 (m, 1H), 4.55-4.52 (m, 1H), 3.84-3.81 (m, 1H), 3.79-3.76 (m, 1H), 3.75-3.65 (m, 1H), 2.49-2.35 (m, 2H), 2.03-2.02 (m, 3H), 1.85-1.72 (m, 1H), 1.25 (s, 3H), 0.95-0.92 (m, 2H), 0.87-0.83 (m, 2H) LCMS: m/z = 404.15 (M + H)$^+$; HPLC: 97.21%, rt: 6.73 min. |
| 53 | 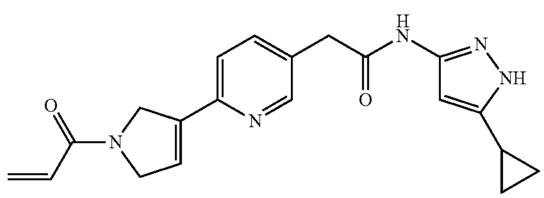 [SMILES: C=CC(=O)N1CC=C(c2ccc(CC(=O)Nc3cc(C4CC4)[nH]n3)cn2)C1] | $^1$HNMR (DMSO-d$_6$, 400 MHz): δ 12.06 (s, 1H), 10.56 (s, 1H), 8.44-8.46 (m, 1H), 7.74-7.65 (m, 2H), 7.75-7.59 (m, 2H), 6.23-6.22 (m, 2H), 5.75-5.71 (m, 1H), 4.80-4.79 (m, 1H), 4.62-4.56 (m, 2H), 4.38-4.37 (m, 1H), 3.63 (m, 2H), 1.84-1.80 (m, 1H), 0.89-0.86 (m, 2H), 0.64-0.60 (m, 2H). LCMS: m/z = 364.05 (M + H)$^+$; HPLC: 98.79%, rt: 5.89 min. |
| 54 | 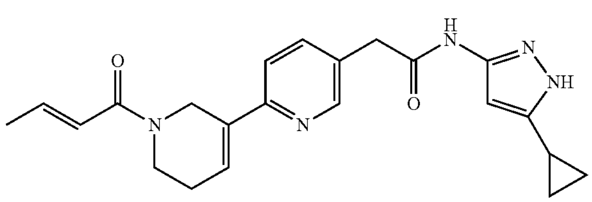 [SMILES: C/C=C/C(=O)N1CCC=C(c2ccc(CC(=O)Nc3cc(C4CC4)[nH]n3)cn2)C1] | $^1$HNMR (DMSO-d$_6$, 400 MHz): δ 12.1 (s, 1H), 10.55 (s, 1H), 8.44 (s, 1H), 7.69-7.68 (m, 1H), 7.63-7.58 (m, 1H), 6.78-6.67 (m, 1H), 6.60-6.52 (m, 1H), 6.11 (s, 1H), 4.51-4.47 (m, 2H), 3.67-3.64 (m, 4H), 2.34-2.28 (m, 2H), 1.84-1.79 (m, 4H), 0.89-0.87 (m, 2H), 0.62-0.61 (m, 2H) LCMS: m/z = 392.30 (M + H)$^+$; HPLC: 95.03%, rt: 5.47 min. |
| 55 | 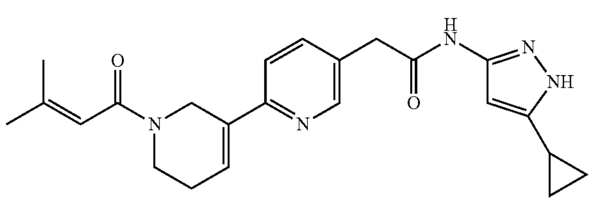 [SMILES: CC(C)=CC(=O)N1CCC=C(c2ccc(CC(=O)Nc3cc(C4CC4)[nH]n3)cn2)C1] | $^1$HNMR (DMSO-d$_6$, 400 MHz): δ 12.1 (s, 1H), 10.55 (s, 1H), 8.43 (s, 1H), 7.69-7.67 (m, 1H), 7.62-7.57 (m, 1H), 6.76-6.73 (m, 1H), 6.11 (s, 1H), 5.98-5.96 (m, 1H), 4.44 (s, 2H), 3.64-3.62 (m, 4H), 2.33-2.29 (m, 2H), 1.86-1.80 (m, 7H), 0.90-0.86 (m, 2H), 0.64-0.61 (m, 2H). LCMS: m/z = 406.20 (M + H)$^+$; HPLC: 97.39%, rt: 5.68 min. |
| 56 | 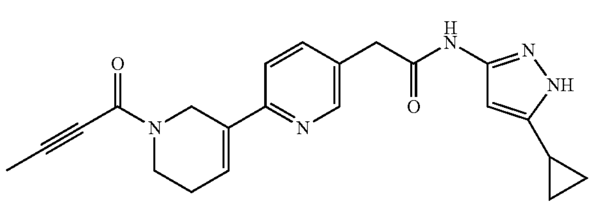 [SMILES: CC#CC(=O)N1CCC=C(c2ccc(CC(=O)Nc3cc(C4CC4)[nH]n3)cn2)C1] | $^1$HNMR (DMSO-d$_6$, 400 MHz): δ 12.1 (s, 1H), 10.55 (s, 1H), 8.44-8.43 (m, 1H), 7.71-7.60 (m, 2H), 6.75 (s, 1H), 6.11 (s, 1H), 4.68-4.67 (m, 1H), 4.45-4.44 (m, 1H), 3.84-3.81 (m, 1H), 3.62-3.61 (m, 3H), 2.39-2.29 (m, 1H), 2.28-2.08 (m, 1H), 2.03 (s, 3H), 1.83-1.79 (m, 1H), 0.89-0.87 (m, 2H), 0.64-0.60 (m, 2H). LCMS: m/z = 392.30 (M + H)$^+$; HPLC: 98.93%, rt: 6.68 min. |

TABLE 2-continued
| Comp. No. | Structure | Characterization data |
|---|---|---|
| 57 | 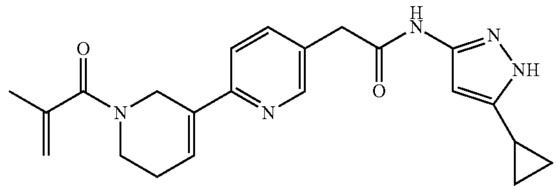 [SMILES: C=C(C)C(=O)N1CCC=C(c2ccc(CC(=O)Nc3cc(C4CC4)[nH]n3)cn2)C1] | ¹HNMR (DMSO-d₆, 400 MHz): δ 12.1 (s, 1H), 10.54 (s, 1H), 8.44 (s, 1H), 7.72-7.56 (m, 2H), 6.58-6.56 (m, 1H), 6.15-6.21 (m, 1H), 5.31-5.21 (m, 1H), 5.11-5.05 (m, 1H), 4.41-4.55 (s, 2H), 3.51-2.95 (m, 5H), 2.29-2.38 (m, 2H), 1.91-1.71 (m, 3H), 0.89-0.87 (m, 2H), 0.62-0.61 (m, 2H). LCMS: m/z = 392.30 (M + H)⁺; HPLC: 98.21%, rt: 6.36 min. |
| 59 | 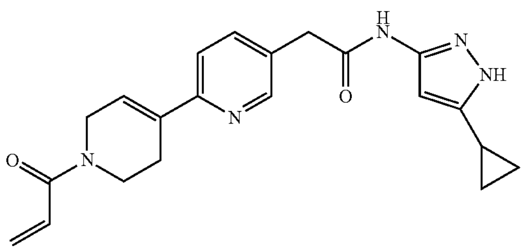 | ¹HNMR (DMSO-d₆, 400 MHz): δ 12.1 (s, 1H), 10.54 (s, 1H), 8.44 (s, 1H), 7.69-7.67 (m, 1H), 7.53-7.51 (m, 1H), 6.90-6.86 (m, 1H), 6.67 (s, 1H), 6.15-6.11 (m, 2H), 5.72-5.69 (m, 1H), 4.31-4.20 (m, 2H), 3.77 (s, 2H), 3.60 (s, 2H), 2.67-2.52 (m, 2H), 1.84-1.80 (m, 1H), 0.90-0.86 (m, 2H), 0.63-0.60 (m, 2H). LCMS: m/z = 392.30 (M + H)⁺; HPLC: 97.83%, rt: 5.65 min. |
Example 2
Synthesis of N-(4-(4-(1-((5-cyclopropyl-1H-pyrazol-3-yl)amino)-1-oxopropan-2-yl)phenyl)cyclohexyl)acrylamide (Compound 10 and Compound 11)
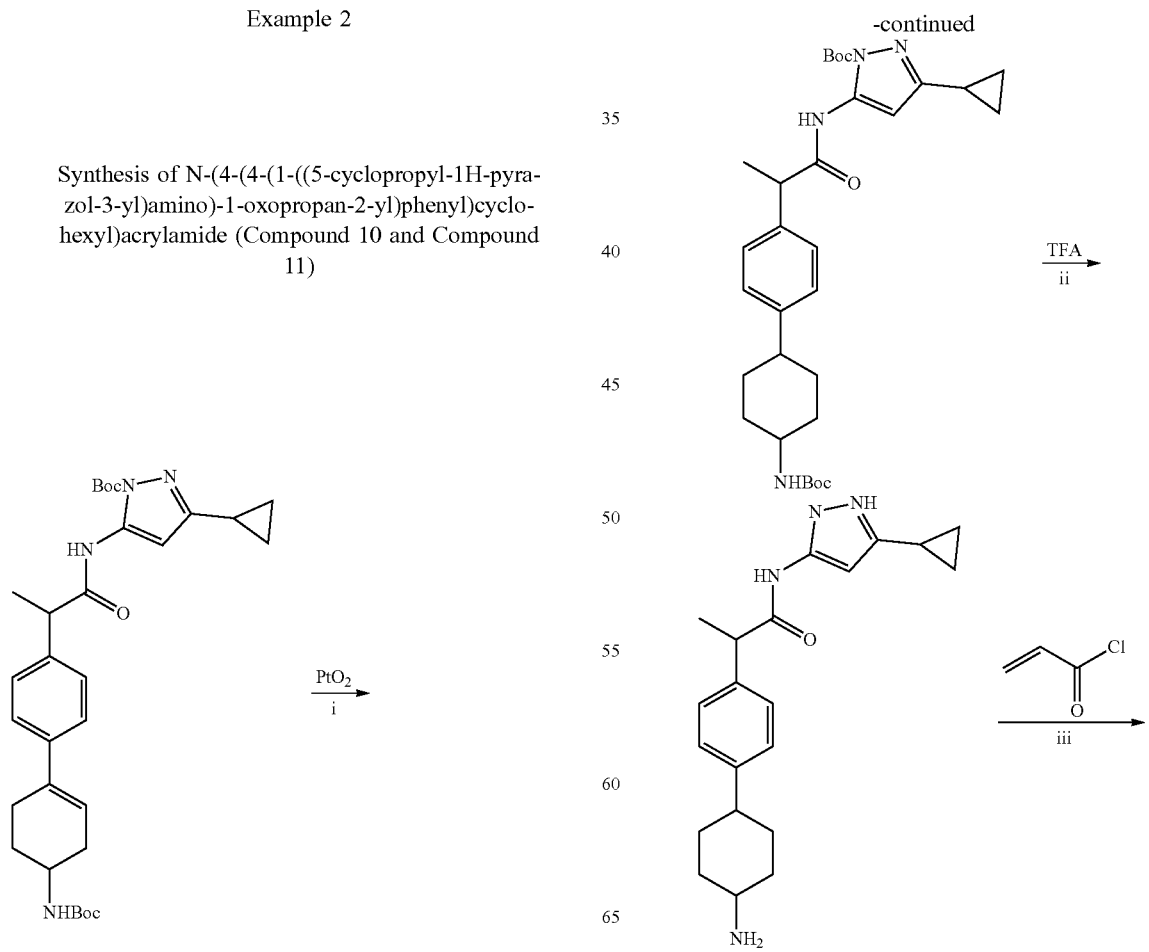

-continued

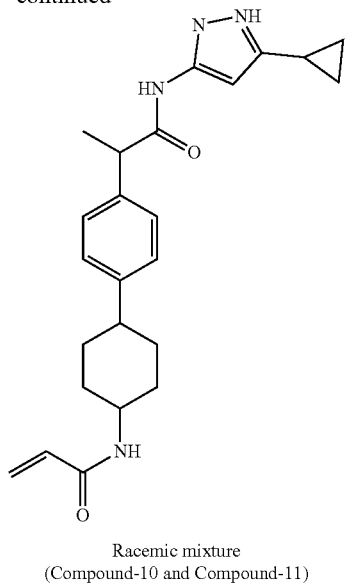

Racemic mixture
(Compound-10 and Compound-11)

Reagents and conditions:
i) H₂, PtO₂, MeOH, 60 psi, 20 h, RT;
ii) TFA, DCM, 0° C.-RT, 1 h;
iii) DIPEA, ACN:H₂O, 0° C., 0.5 h.

Step-i: Synthesis of tert-butyl 5-(2-(4-(4-((tert-butoxycarbonyl)amino)cyclohexyl)phenyl) propanamido)-3-cyclopropyl-1H-pyrazole-1-carboxylate PtO₂ (0.1 g) was added to a degassed solution of tert-butyl 5-(2-(4'-((tert-butoxycarbonyl)amino)-2',3',4',5'-tetrahydro-[1,1'-biphenyl]-4-yl)propanamido)-3-cyclopropyl-1H-pyrazole-1-carboxylate (0.3 g, 0.66 mmol) (synthesis carried out as described in Example-1) in methanol (30 mL). The reaction mixture was subjected to hydrogenation at 60 psi in Parr shaker for 20 h at room temperature. Reaction mass was filtered through celite bed and washed the celite bed with methanol. The filtrate was concentrated under reduced pressure to afford the title compound (0.2 g, 66%). LCMS: m/z=553.1 (M+H)⁺.

Step-ii: Synthesis of 2-(4-(4-aminocyclohexyl)phenyl)-N-(5-cyclopropyl-1H-pyrazol-3-yl)propanamide TFA (0.3 mL) was slowly added to a stirred solution of tert-butyl 5-(2-(4-(4-((tert-butoxycarbonyl)amino)cyclohexyl)phenyl)propanamido)-3-cyclopropyl-1H-pyrazole-1-carboxylate (0.06 g, 0.17 mmol) in dry DCM (2 mL) under argon atmosphere at 0° C. The resulting reaction mixture was allowed to warm to room temperature and stirred for 1 h. After completion of the reaction, excess of solvent was removed under reduce pressure and residue was suspended in saturated sodium bicarbonate solution. Aqueous layer was extracted thrice with ethyl acetate and combined organic layer was dried over sodium sulphate and concentrated to afford title compound (0.035 g, 76%). LCMS: m/z=353.1 (M+H)⁺.

Step-iii: Synthesis of N-(4-(4-(1-((5-cyclopropyl-1H-pyrazol-3-yl)amino)-1-oxopropan-2-yl)phenyl)cyclohexyl)acrylamide 2-(4-(4-aminocyclohexyl)phenyl)-N-(5-cyclopropyl-1H-pyrazol-3-yl)propanamide (0.4 g, 0.11 mmol) was dissolved in mixture of 5.5 mL ACN:H₂O (9:1), DIPEA (0.03 mL, 0.28 mmol) and acryloyl chloride (9.2 mg, 0.10 mmol) was added to above solution at 0° C. and resultant mixture was stir for 30 min. Reaction mass was quenched with water and diluted with DCM. Organic layer was separated and aqueous layer was further extracted with DCM. Combined organic layer was dried over sodium sulphate and concentrated to afford crude compound. Crude was further purified using flash chromatography using 0-5% MeOH in DCM mixture as eluent to afford title compound (0.03 g, 64%).

Racemic mixture of N-(4-(4-(1-((5-cyclopropyl-1H-pyrazol-3-yl)amino)-1-oxopropan-2-yl)phenyl)cyclohexyl)acrylamide (0.03 g) was separated by using chiral prep column. (Method: Column: Lux 5μ Cellulose-4(10.0×250 mm), Elution: isocratic (95:5), A=ACN, B=0.1% DEA in EtOH) to afford the pure Isomer-1 (0.01 g) and Isomer-2 (0.01 g).

Isomer-1 (Compound 10): ¹HNMR (CDCl₃, 400 MHz): δ 8.15-8.10 (m, 1H), 7.28-7.22 (m, 3H), 6.40-6.38 (m, 1H), 6.24-6.20 (m, 1H), 6.10-6.05 (m, 1H), 5.65-5.62 (m, 1H), 4.15-4.10 (m, 1H), 3.81-3.80 (m, 1H), 2.61-2.55 (m, 2H), 1.86-1.77 (m, 4H), 1.75-1.69 (m, 4H), 1.48 (d, 3H), 0.95-0.93 (m, 2H), 0.69-0.68 (m, 2H). LCMS: m/z=407.1 (M+H)⁺; HPLC: 98.06%, rt: 4.99 min Isomer-2 (Compound 11): ¹HNMR (CD₃OD, 400 MHz): δ 8.15-8.10 (m, 1H), 7.28-7.22 (m, 3H), 6.40-6.38 (m, 1H), 6.24-6.20 (m, 1H), 6.10-6.05 (m, 1H), 5.65-5.62 (m, 1H), 4.15-4.10 (m, 1H), 3.81-3.80 (m, 1H), 2.61-2.55 (m, 2H), 1.86-1.77 (m, 4H), 1.75-1.69 (m, 4H), 1.48 (d, 3H), 0.95-0.93 (m, 2H), 0.69-0.68 (m, 2H). LCMS: m/z=407.1 (M+H)⁺; HPLC: 99.04%, rt: 5.10 min.

The compounds listed in below Table 3 were prepared by procedure similar to the one described in Example 2 with appropriate variations in reactants, quantities of reagents, protections and de-protections, solvents and reaction conditions. The characterization data of the compounds are summarized herein the below table.

TABLE 3

| Comp. No. | Structure | Characterization data |
|---|---|---|
| 12 | 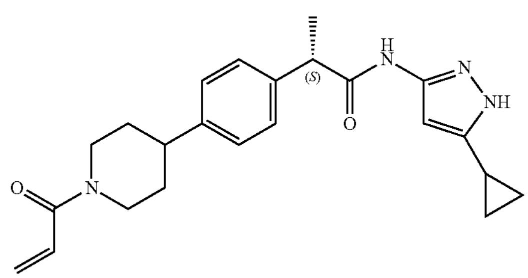 | ¹HNMR (DMSO-d₆, 400 MHz): δ 12.1 (s, 1H), 10.37 (s, 1H), 7.28-7.26 (m, 2H), 7.18-7.15 (m, 2H), 6.87-6.80 (m, 1H), 6.12-6.07 (m, 2H), 5.67-5.64 (m, 1H), 4.57-4.54 (m, 1H), 4.17-4.13 (m, 1H), 3.81-3.76 (m, 1H), 3.34-3.08 (m, 1H), 2.74-2.64 (m, 2H), 1.82-1.77 (m, 1H), 1.50-1.48 (m, 2H), 1.36 (d, 3H), 0.88-0.86 (m, 2H), 0.61-0.60 (m, 2H). LCMS: m/z = 393.0 (M + H)⁺; HPLC: 99.39%, rt: 6.90 min; Chiral HPLC: 95.91%, rt: 5.99 min. |

TABLE 3-continued

| Comp. No. | Structure | Characterization data |
|---|---|---|
| 13 | 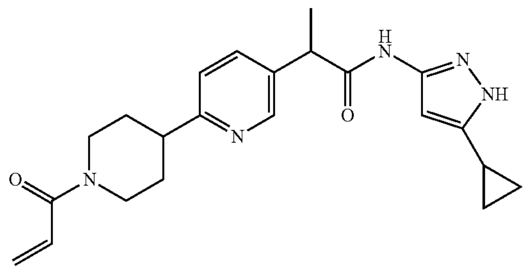 [SMILES: C=CC(=O)N1CCC(c2ccc(C(C)C(=O)Nc3cc(C4CC4)[nH]n3)cn2)CC1] | $^1$HNMR (DMSO-$d_6$, 400 MHz): δ 12.1 (s, 1H), 10.48 (s, 1H), 8.45 (d, 1H), 7.68 (m, 2H), 7.25 (d, 1H), 6.88-6.78 (m, 1H), 6.13-6.06 (m, 2H), 5.68-5.64 (m, 1H), 4.55-4.51 (m, 1H), 4.17-4.12 (m, 1H), 3.87-3.80 (m, 1H), 3.35-3.11 (m, 1H), 2.95-2.88 (m, 2H), 2.75-2.67 (m, 1H), 1.85-1.81 (m, 1H), 1.61-1.52 (m, 2H), 1.38 (d, 3H), 0.90-0.84 (m, 2H), 0.63-0.60 (m, 2H). LCMS: m/z = 394.1 (M + H)$^+$; HPLC: 99.19%, rt: 4.88 min; |
| 41 | 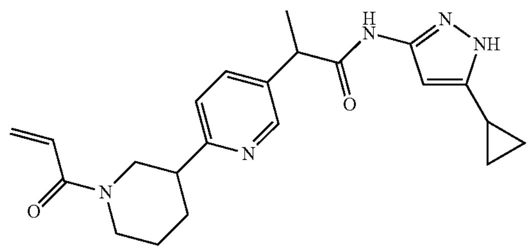 [SMILES: C=CC(=O)N1CCCC(c2ccc(C(C)C(=O)Nc3cc(C4CC4)[nH]n3)cn2)C1] | $^1$HNMR (DMSO-$d_6$, 400 MHz): δ 12.1 (s, 1H), 10.52 (s, 1H), 8.48 (s, 1H), 7.71-7.68 (m, 1H), 6.30-6.26 (m, 1H), 6.87-6.77 (m, 1H), 6.12-6.04 (m, 2H), 5.68-5.59 (m, 1H), 4.56-4.13 (m, 1H), 4.06-3.88 (m, 1H), 3.86-3.65 (m, 1H), 3.54-3.44 (m, 1H), 3.05-3.0 (m, 1H), 2.80-2.60 (m, 2H), 2.00-1.90 (m, 1H), 1.89-1.70 (m, 2H), 1.47-1.35 (m, 4H), 0.89-0.87 (m, 2H), 0.62-0.61 (m, 2H). LCMS: m/z = 394.11 (M + H)$^+$; HPLC: 94.63%, rt: 10.31 min. |
| 48 | 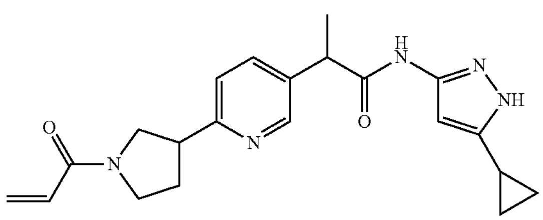 [SMILES: C=CC(=O)N1CCC(c2ccc(C(C)C(=O)Nc3cc(C4CC4)[nH]n3)cn2)C1] | $^1$HNMR (DMSO-$d_6$, 400 MHz): δ 12.03 (s, 1H), 10.45 (s, 1H), 8.46-8.46 (m, 1H), 7.69-7.66 (m, 1H), 7.31-7.27 (m, 1H), 6.61-6.53 (m, 1H), 6.13-6.08 (m, 2H), 5.65-5.60 (m, 1H), 3.97-3.81 (m, 1H), 3.77-3.72 (m, 1H), 3.66-3.54 (m, 2H), 3.47-3.30 (m, 2H), 2.30-1.97 (m, 2H), 1.82-1.75 (m, 1H), 1.36-1.34 (m, 3H), 0.86-0.84 (m, 2H), 0.61-0.57 (m, 2H); LCMS: m/z = 378 (M + H)$^+$; HPLC: 95%, rt: 5.68 min. |

Example 3

Synthesis of (S,E)-N-(5-cyclopropyl-1H-pyrazol-3-yl)-2-(4-(1-(4-(diethylamino)but-2-enoyl)-1,2,3,6-tetrahydropyridin-4-yl)phenyl)propanamide (Compound 14)

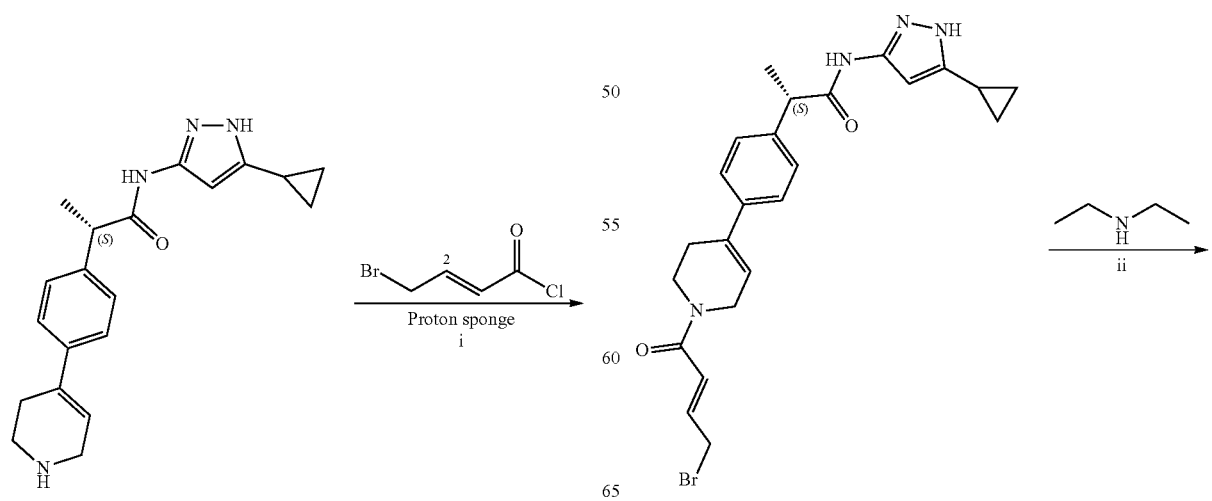

-continued

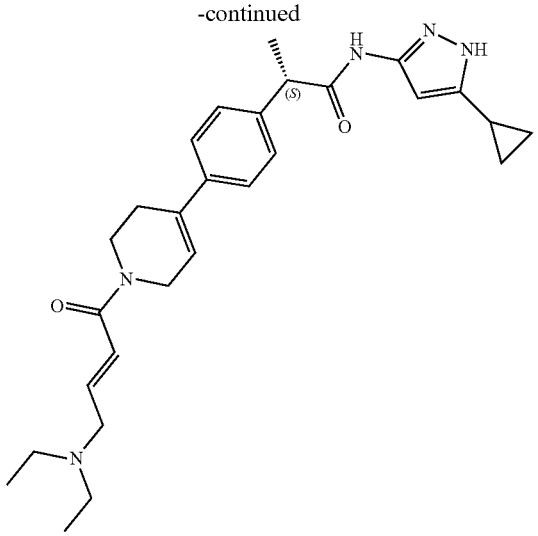

Compound-14

Reagents and conditons:
i) Proton sponge, DCM, 0° C.-RT, 1 h;
ii) DCM, RT, 8 h.
Step-i: Synthesis of (S,E)-2-(4-(1-(4-bromobut-2-enoyl)-1,2,3,6-tetrahydropyridin-4-yl)phenyl)-N-(5-cyclopropyl-1H-pyrazol-3-yl)propanamide To a solution of (S)—N-(5-cyclopropyl-1H-pyrazol-3-yl)-2-(4-(1,2,3,6-tetrahydropyridin-4-yl)phenyl)propanamide (0.25 g, 0.75 mmol) (synthesis carried out as described in Example-1) and 1,8-Bis(dimethylamino)naphthalene (Proton sponge) (0.2 g, 0.93 mmol) in DCM (20 mL) was added (E)-4-bromobut-2-enoyl chloride (0.15 g, 0.82 mmol) at 0° C. and reaction stirred for 1 h at room temperature. The reaction mass was diluted with DCM and water, organic layer was separated and aqueous layer was further extracted with DCM. Combined organic layer was dried over sodium sulphate and concentrated to afford crude compound. Crude was further purified using flash chromatography using 0-5% MeOH in DCM mixture as eluent to afford title compound (0.25 g, 38%). LCMS: m/z=484.0 (M+H)$^+$.

Step-ii: Synthesis of (S,E)-N-(5-cyclopropyl-1H-pyrazol-3-yl)-2-(4-(1-(4-(diethylamino) but-2-enoyl)-1,2,3,6-tetrahydropyridin-4-yl)phenyl)propanamide To a stirred solution of (S,E)-2-(4-(1-(4-bromobut-2-enoyl)-1,2,3,6-tetrahydropyridin-4-yl)phenyl)-N-(5-cyclopropyl-1H-pyrazol-3-yl)propanamide (0.1 g, 0.20 mmol)) in DCM (2 mL) was added N,N, Diethyl amine (0.07 g, 1 mmol) and reaction stirred at room temperature for 8 h. The reaction mass was diluted with DCM and water, organic layer was separated and aqueous layer was further extracted with DCM. Combined organic layer was dried over sodium sulphate and concentrated to afford crude compound. Crude was further purified using flash chromatography using 2-8% MeOH in DCM mixture as eluent to afford title compound (0.03 g, 30%). $^1$HNMR (CD$_3$OD, 400 MHz): δ 7.40-7.33 (m, 4H), 6.90-6.80 (m, 1H), 6.75-6.60 (m, 1H), 6.10-6.05 (m, 2H), 4.28-4.24 (m, 2H), 3.85-3.80 (m, 3H), 3.34-3.32 (m, 2H), 2.61-2.55 (m, 6H), 1.88-1.85 (m, 1H), 1.46 (d, 3H), 1.09-1.06 (m, 6H), 0.95-0.93 (m, 2H), 0.68-0.67 (m, 2H). LCMS: m/z=476.1 (M+H)$^+$; HPLC: 95.36%, rt: 5.26 min.

The compounds listed in below Table 4 were prepared by procedure similar to the one described in Example 3 with appropriate variations in reactants, quantities of reagents, protections and deprotections, solvents and reaction conditions. The characterization data of the compounds are summarized herein the below table.

TABLE 4

| Comp. No. | Structure | Characterization data |
|---|---|---|
| 15 | 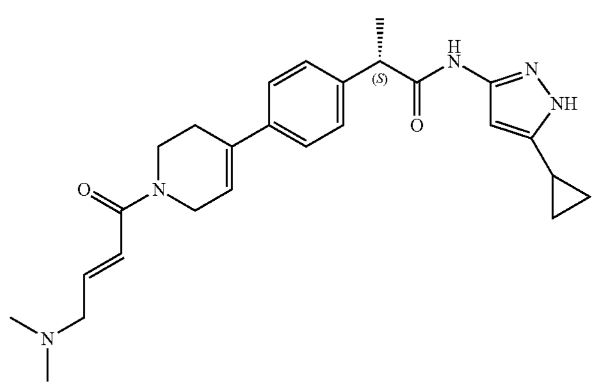 | $^1$HNMR (CD$_3$OD, 400 MHz): δ 7.40-7.33 (m, 4H), 6.76-6.73 (m, 1H), 6.75-6.60 (m, 1H), 6.15-6.10 (m, 2H), 4.29-4.24 (m, 2H), 3.85-3.84 (m, 3H), 3.22-3.12 (m, 2H), 2.61-2.56 (m, 2H), 2.31 (s, 6H), 1.88-1.80 (m, 1H), 1.48 (d, 3H), 0.95-0.93 (m, 2H), 0.68-0.67 (m, 2H). LCMS: m/z = 448.4 (M + H)$^+$; HPLC: 99.02%, rt: 5.17 min, Chiral HPLC: 97.84%, rt: 11.70 min. |

TABLE 4-continued

| Comp. No. | Structure | Characterization data |
|---|---|---|
| 16 | 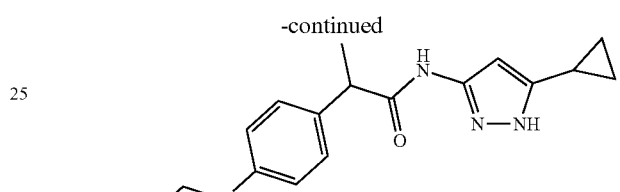 | $^1$HNMR (CD$_3$OD, 400 MHz): δ 7.40-7.33 (m, 4H), 6.77-6.74 (m, 1H), 6.70-6.65 (m, 1H), 6.12-6.09 (m, 2H), 4.28-4.23 (m, 2H), 3.84-3.79 (m, 3H), 3.72-3.70 (m, 4H), 3.22-3.19 (m, 2H), 2.60-2.55 (m, 2H), 2.50-2.49 (m, 4H), 1.86-1.83 (m, 1H), 1.48 (d, 3H), 0.95-0.93 (m, 2H), 0.68-0.67 (m, 2H). LCMS: m/z = 490.1 (M + H)$^+$; HPLC: 95.13%, rt: 6.23 min, Chiral HPLC: 97.80%, rt: 12.95 min. |

Example 4

Synthesis of 2-(4-(4-acryloylpiperazin-1-yl)phenyl)-N-(5-cyclopropyl-1H-pyrazol-3-yl) propanamide (Compound 17)

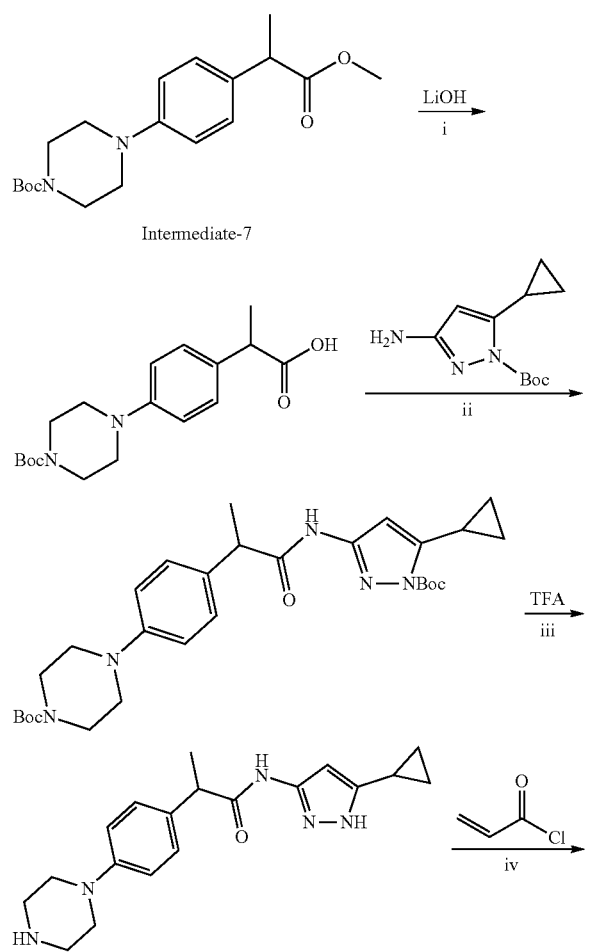

Compound-17

Reagents and conditions:
i) LiOH, MeOH, THF, water, RT, 12 h;
ii) HATU, DIPEA, DMF, 0° C.-RT, 12 h;
iii) TFA, CH$_2$Cl$_2$, 0° C., 1 h-RT;
iv) DIPEA, ACN:H$_2$O 0° C.-RT, 0.5 h.

Step-i: Synthesis of 2-(4-(4-(tert-butoxycarbonyl) piperazin-1-yl)phenyl)propanoic acid A suspension of tert-butyl 4-(4-(1-methoxy-1-oxopropan-2-yl)phenyl)piperazine-1-carboxylate (11 g, 31.5 mmol) (Intermediate-7), LiOH.H$_2$O (1.51 g, 63.13 mmol) in THF (60 mL), methanol (40 mL) and water (20 mL) mixture was stirred at room temperature for 12 h. Reaction mixture was concentrated under reduced pressure to remove solvent completely. The solid residue was dissolved in minimum quantity of water (50 mL) and washed with diethyl ether to remove non polar impurities. The aqueous layer was separated and cooled to 0° C. followed by adjusting pH 2 using aq. 1N HCl. The product was extracted with DCM thrice and obtained organic layer was washed with saturated brine, and dried over anhydrous sodium sulfate, and the solvent was distilled off under reduced pressure to get the desired product (7.4 g, 72%). LCMS: m/z=335 (M+H)$^+$.

Step-ii: Synthesis of tert-butyl 4-(4-(1-((1-(tert-butoxycarbonyl)-5-cyclopropyl-1H-pyrazol-3-yl) amino)-1-oxopropan-2-yl)phenyl)piperazine-1-carboxylate To a solution of 2-(4-(4-(tert-butoxycarbonyl)piperazin-1-yl)phenyl)propanoic acid (1 g, 2.99 mmol) in DCM (12 mL) was added HATU (1.47 g, 38.9 mmol) at 0° C. followed by DIPEA (0.77 g, 5.98 mmol) and finally added tert-butyl 3-amino-5-cyclopropyl-1H-pyrazole-1-carboxylate (0.56 g, 2.54 mmol) (synthesis carried out as described in reference Tetrahedron Letters, 2005, vol. 46, #6 p. 933-935). The reaction mass was stirred for 12 h at room temperature. The reaction mixture was quenched with ice-water and diluted with ethyl acetate. The aqueous layer was separated and extracted with ethyl acetate (2×25 mL). The combined organic phase was washed with brine, dried over Na$_2$SO$_4$, filtered and concentrated under reduced pressure. Crude compound was further purified by column chromatography (3% of methanol in DCM) to get the pure compound (0.7 g, 43%). LCMS: m/z=540.1 (M+H)$^+$.

Step-iii: Synthesis of N-(5-cyclopropyl-1H-pyrazol-3-yl)-2-(4-(piperazin-1-yl)phenyl) propanamide To a solution of tert-butyl 4-(4-(1-((1-(tert-butoxycarbonyl)-5-cyclopropyl-1H-pyrazol-3-yl)amino)-1-oxopropan-2-yl)phenyl)piperazine-1-carboxylate (0.24 g, 0.44 mmol) in DCM (5 mL) was added TFA (1 mL) at room temperature and stirred at the same temperature for further 1 h under argon atmosphere. After completion of reaction distilled out the solvent and diluted the reaction mixture with water (30 mL) and then further it was basified with saturated sodium bicarbonate solution. The aqueous layer was extracted with DCM (10 mL×3). The combined organic layer were washed with water, brine solution and dried over anhydrous Na$_2$SO$_4$ and concentrated under reduced pressure to get 0.18 g (92%) of N-(5-cyclopropyl-1H-pyrazol-3-yl)-2-(4-(piperazin-1-yl)phenyl)propanamide. LCMS: m/z=440.1 (M+H)$^+$.

Step-iv: Synthesis of 2-(4-(4-acryloylpiperazin-1-yl)phenyl)-N-(5-cyclopropyl-1H-pyrazol-3-yl)propanamide To a solution of N-(5-cyclopropyl-1H-pyrazol-3-yl)-2-(4-(piperazin-1-yl)phenyl)propanamide (0.20 g, 0.58 mmol) in ACN (10 mL) was added water (2 mL), DIPEA (0.15 mL, 1.17 mmol) and acryloyl chloride (0.042 g, 0.47 mmol) at 0° C. After 30 min, the reaction mixture was quenched with ice-water and diluted with DCM. The aqueous layer was separated and extracted with DCM (2×10 mL). The combined organic phase was washed with brine, dried over Na$_2$SO$_4$, filtered and concentrated. The crude residue was purified by silica column chromatography by eluting with 0-5% MeOH-DCM to afford the title compound (0.06 g, 25%). $^1$HNMR (DMSO-d$_6$, 300 MHz): δ 11.89 (s, 1H), 10.30 (s, 1H), 7.23 (d, 2H), 6.91-6.88 (m, 2H), 6.85-6.80 (m, 1H), 6.16-6.09 (m, 2H), 5.72-5.67 (m, 1H), 3.73-3.67 (m, 5H), 3.08 (s, 4H), 1.85-1.80 (m, 1H), 1.32 (d, 3H), 0.88-0.85 (d, 2H), 0.61-0.59 (m, 2H); LCMS: m/z=394.10 (M+H)$^+$; HPLC: 97.41%, rt: 6.57 min.

Racemic of 2-(4-(4-acryloylpiperazin-1-yl)phenyl)-N-(5-cyclopropyl-1H-pyrazol-3-yl)propanamide (0.06 g) was separated by using chiral prep column. (Method: Column: Lux 5µ Cellulose-4(10.0×250 mm), Elution: isocratic (95:5), A=Hexane, B=IPA:Methanol (1:1) to afford the pure Isomer-1 (0.02 g) and Isomer-2 (0.02 g).

Isomer-1 (Compound 18): $^1$HNMR (DMSO-d$_6$, 300 MHz): δ 11.89 (s, 1H), 10.30 (s, 1H), 7.23 (d, 2H), 6.91-6.88 (m, 2H), 6.85-6.80 (m, 1H), 6.16-6.09 (m, 2H), 5.72-5.67 (m, 1H), 3.73-3.67 (m, 5H), 3.08 (s, 4H), 1.85-1.80 (m, 1H), 1.32 (d, 3H), 0.88-0.85 (d, 2H), 0.61-0.59 (m, 2H); LCMS: m/z=394.10 (M+H)$^+$; HPLC: 99.68%, rt: 6.54 min; Chiral HPLC: 99.20%, rt: 25.79 min.

Isomer-2 (Compound 19): $^1$HNMR (DMSO-d$_6$, 300 MHz): δ 11.89 (s, 1H), 10.30 (s, 1H), 7.23 (d, 2H), 6.91-6.88 (m, 2H), 6.85-6.80 (m, 1H), 6.16-6.09 (m, 2H), 5.72-5.67 (m, 1H), 3.73-3.67 (m, 5H), 3.08 (s, 4H), 1.85-1.80 (m, 1H), 1.32 (d, 3H), 0.88-0.85 (d, 2H), 0.61-0.59 (m, 2H); LCMS: m/z=394.10 (M+H)$^+$; HPLC: 99.27%, rt: 6.54 min; Chiral HPLC: 98.65%, rt: 29.98 min.

The compounds listed in below Table 5 were prepared by procedure similar to the one described in Example 4 with appropriate variations in reactants, quantities of reagents, protections and de-protections, solvents and reaction conditions. The characterization data of the compounds are summarized herein the below table.

TABLE 5

| Comp. No. | Structure | Characterization data |
|---|---|---|
| 20 | 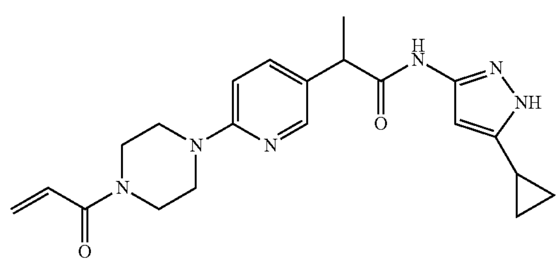 [SMILES: C=CC(=O)N1CCN(c2ccc(C(C)C(=O)Nc3cc(C4CC4)[nH]n3)cn2)CC1] | $^1$HNMR (DMSO-d$_6$, 400 MHz): δ 11.98 (s, 1H), 10.30 (s, 1H), 8.09 (d, 1H), 7.55-7.52 (m, 1H), 6.87-6.80 (m, 2H), 6.15-6.10 (m, 2H), 5.71-5.68 (m, 1H), 3.73-3.71 (m, 1H), 3.65-3.60 (m, 4H), 3.46-3.34 (m, 4H), 1.83-1.80 (m, 1H), 1.34 (d, 3H), 0.90-0.85 (m, 2H), 0.63-0.59 (m, 2H); LCMS: m/z = 394.9 (M + H)$^+$; HPLC: 94.27%, rt: 5.57 min. |
| 21 | 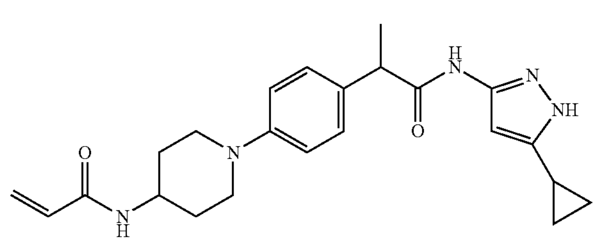 [SMILES: C=CC(=O)NC1CCN(c2ccc(C(C)C(=O)Nc3cc(C4CC4)[nH]n3)cc2)CC1] | $^1$HNMR (DMSO-d$_6$, 400 MHz): δ 11.98 (s, 1H), 10.28 (s, 1H), 8.04 (d, 1H), 7.19 (d, 2H), 6.88 (d, 2H), 6.21-6.04 (m, 3H), 5.57-5.54 (m, 1H), 3.80-3.60 (m, 4H), 2.79-2.66 (m, 2H), 1.83-1.77 (m, 3H), 1.51-1.42 (m, 2H), 1.30 (d, 3H), 0.90-0.85 (m, 2H), 0.62-0.59 (m, 2H); LCMS: m/z = 408.05 (M + H)$^+$; HPLC: 98.14%, rt: 5.08 min. |

Example 5

Synthesis of N-(5-cyclopropyl-1H-pyrazol-3-yl)-2-(1'-propioloyl-1',2',3',6'-tetrahydro-[2,4'-bipyridin]-5-yl)propanamide (Compound 50)

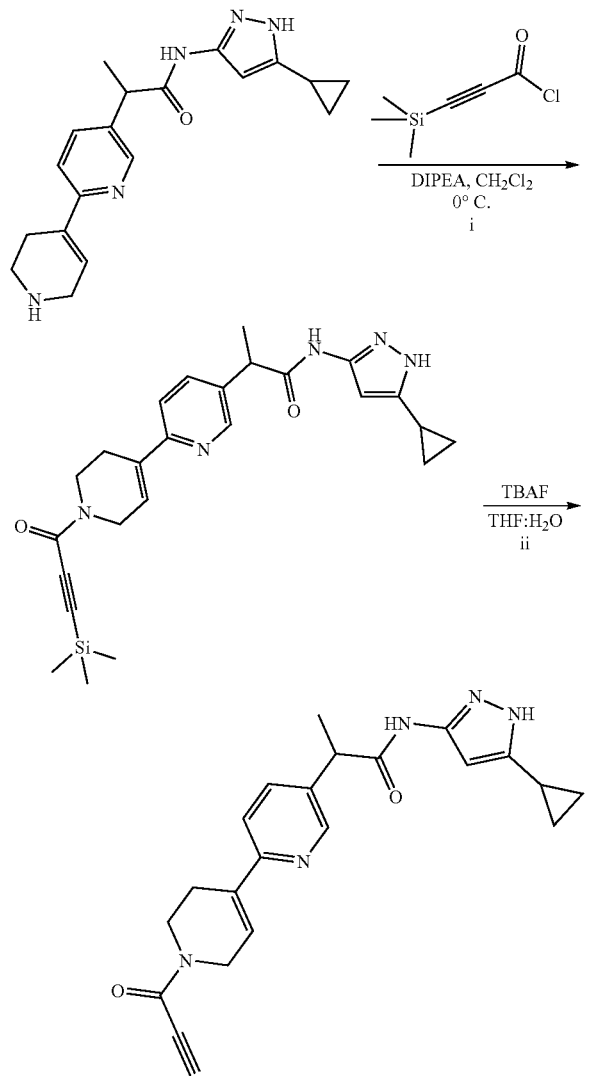

Reagents and conditions:
i) DIPEA, CH$_2$Cl$_2$ 0° C.-RT, 0.5 h;
ii) TBAF, THF:H$_2$O, 0° C.-RT, 1 h.

Step-i: Synthesis N-(5-cyclopropyl-1H-pyrazol-3-yl)-2-(1'-(3-(trimethylsilyl)propioloyl)-1',2',3',6'-tetrahydro-[2,4'-bipyridin]-5-yl)propanamide To a solution of N-(5-cyclopropyl-1H-pyrazol-3-yl)-2-(1',2',3',6'-tetrahydro-[2,4'-bipyridin]-5-yl)propanamide (0.384 g, 1.14 mmol) (synthesis carried out as described in Example-1) in DCM (15 mL) was added DIPEA (0.5 mL, 3.87 mmol) and 3-(trimethylsilyl)propioloyl chloride (0.20 g, 1.25 mmol) at 0° C. After 30 min, the reaction mixture was quenched with ice-water and diluted with DCM. The aqueous layer was separated and extracted with DCM (2×10 mL). The combined organic phase was washed with brine, dried over Na$_2$SO$_4$, filtered and concentrated. The crude residue was purified by silica column chromatography by eluting with 0-5% MeOH-DCM to afford the title compound (0.28 g, 53%). LCMS: m/z=462.1 (M+H)$^+$.

Step-ii: Synthesis N-(5-cyclopropyl-1H-pyrazol-3-yl)-2-(1'-propioloyl-1',2',3',6'-tetrahydro-[2,4'-bipyridin]-5-yl)propanamide To a solution of N-(5-cyclopropyl-1H-pyrazol-3-yl)-2-(1'-(3-(trimethylsilyl) propioloyl)-1',2',3',6'-tetrahydro-[2,4'-bipyridin]-5-yl)propanamide in THF (4 m L) and water (1 mL) mixture was added TBAF (1M) (0.65 mL) at 0° C. After stirring at room temperature for 1 h, the reaction mixture was quenched with ice-water and diluted with DCM. The aqueous layer was separated and extracted with DCM (2×10 mL). The combined organic phase was washed with brine, dried over Na$_2$SO$_4$, filtered and concentrated. The crude residue was purified by silica column chromatography by eluting with 0-5% MeOH-DCM to afford the title compound (0.12 g, 50%). $^1$HNMR (CDCl$_3$, 400 MHz): δ 8.50 (s, 1H), 7.81-7.82 (m, 1H), 7.71-7.69 (m, 1H), 7.39-7.35 (m, 1H), 6.53-6.51 (m, 2H), 6.30 (s, 1H), 4.48-4.47 (m, 1H), 4.31-4.30 (m, 1H), 3.88-3.84 (m, 1H), 3.69-3.68 (m, 1H), 3.18 (s, 1H), 2.81-2.45 (m, 2H), 1.80-1.78 (m, 1H), 1.57 (s, 2H), 0.96-0.93 (m, 2H), 0.72-0.71 (m, 2H). LCMS: m/z=390.15 (M+H)$^+$; HPLC: 98.16%, rt: 8.23 min.

The compounds listed in below Table 6 were prepared by procedure similar to the one described in Example 5 with appropriate variations in reactants, quantities of reagents, protections and de-protections, solvents and reaction conditions. The characterization data of the compounds are summarized herein the below table.

TABLE 6

| Comp. No. | Structure | Characterization data |
|---|---|---|
| 58 | 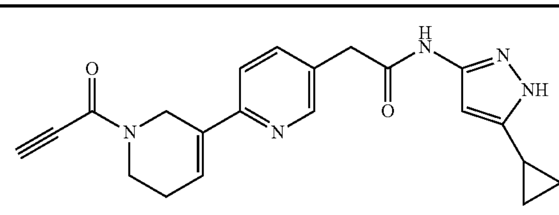 | $^1$HNMR (DMSO-d$_6$, 400 MHz): δ 12.1 (s, 1H), 10.55 (s, 1H), 8.43 (s, 1H), 7.71-7.61 (m, 1H), 6.75 (s, 1H), 6.11 (s, 1H), 4.72-4.70 (m, 1H), 4.47-4.35 (m, 1H), 3.86-3.83 (m, 1H), 3.67-3.61 (m, 1H), 3.60 (s, 2H), 2.52 (s, 1H), 2.32-2.08 (m, 2H), 1.84-1.79 (m, 1H), 0.87-0.85 (m, 2H), 0.63-0.61 (m, 2H). LCMS: m/z = 376.15 (M + H)$^+$; HPLC: 95.57%, rt: 6.56 min. |

TABLE 6-continued

| Comp. No. | Structure | Characterization data |
|---|---|---|
| 60 | 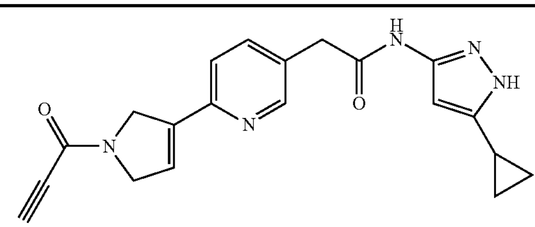 | $^1$HNMR (DMSO-$d_6$, 400 MHz): δ 12.1 (s, 1H), 10.55 (s, 1H), 8.46-8.45 (m, 1H), 7.67-7.65 (m, 3H), 6.68-6.07 (m, 1H), 6.11 (s, 1H), 4.79-4.60 (m, 1H), 4.61-4.60 (m, 1H), 4.55-4.51 (m, 1H), 4.34-4.33 (m, 1H), 3.64-3.62 (s, 2H), 1.84-1.80 (m, 1H), 0.87-0.80 (m, 2H), 0.63-0.61 (m, 2H). LCMS: m/z = 362.10 (M + H)$^+$; HPLC: 94%, rt: 7.32 min. |

Example 6

Synthesis of 2-(1'-cyano-1',2',3',6'-tetrahydro-[2,4'-bipyridin]-5-yl)-N-(5-cyclopropyl-1H-pyrazol-3-yl)acetamide (Compound 62)

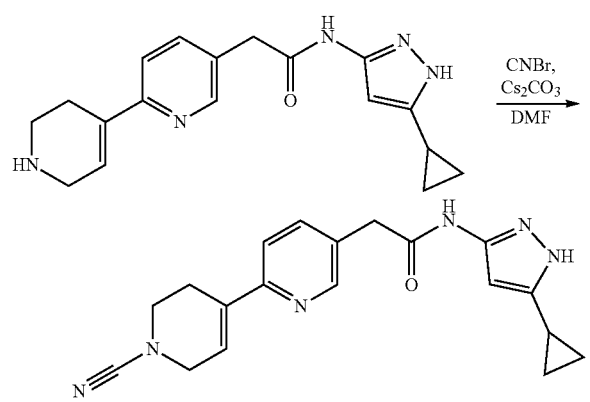

To a solution of N-(5-cyclopropyl-1H-pyrazol-3-yl)-2-(1',2',3',6'-tetrahydro-[2,4'-bipyridin]-5-yl)acetamide (0.30 g, 0.92 mmol) (synthesis carried out as described in Example-1) in DMF was added Cesium carbonate (0.50 g, 1.53 mmol) at 0° C., stirred for 15 min and cyanogen bromide (0.093 g, 0.89 mmol) in THF (1 mL) was added dropwise. After the addition, mixture was stirred for 8 hour at ambient temperature then the reaction mixture was quenched with ice water and diluted with DCM. The aqueous layer was separated and extracted with DCM (2×10 mL). The combined organic phase was washed with brine, dried over Na$_2$SO$_4$, filtered and concentrated. The crude residue was purified by silica column chromatography by eluting with 0-5% MeOH-DCM to afford the title compound (0.08 g, 25%). $^1$HNMR (DMSO-$d_6$, 400 MHz): δ 12.1 (s, 1H), 10.55 (s, 1H), 8.44 (s, 1H), 7.71-7.68 (m, 1H), 7.54-7.52 (m, 1H), 6.63 (s, 1H), 6.21-6.20 (m, 1H), 3.98-3.97 (m, 2H), 3.61 (s, 2H), 3.45-3.42 (m, 2H), 2.69-2.67 (m, 2H), 1.84-1.80 (m, 1H), 0.89-0.87 (m, 2H), 0.64-0.60 (m, 2H). LCMS: m/z=349.05 (M+H)$^+$; HPLC: 96.85%, rt: 5.65 min.

The compound in below Table 7 was prepared by procedure similar to the one described in Example 6 with appropriate variations in reactants, quantities of reagents, protections and de-protections, solvents and reaction conditions. The characterization data of the compound is summarized herein the below table.

TABLE 7

| Comp. No. | Structure | Characterization data |
|---|---|---|
| 61 | 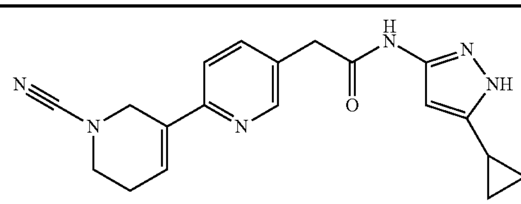 | $^1$HNMR (DMSO-$d_6$, 400 MHz): δ 12.1 (s, 1H), 10.55 (s, 1H), 8.42 (s, 1H), 7.70-7.68 (m, 1H), 7.60-7.58 (m, 1H), 6.71 (s, 1H), 6.31-6.21 (m, 1H), 4.25-4.20 (m, 2H), 3.61 (s, 2H), 2.48-2.35 (m, 4H), 1.84-1.80 (m, 1H), 0.89-0.87 (m, 2H), 0.64-0.60 (m, 2H). LCMS: m/z = 349.20 (M + H)$^+$; HPLC: 98.91%, rt: 6.03 min. |

Although the present application has been illustrated by certain of the preceding examples, it is not to be construed as being limited thereby; but rather, the present application encompasses the generic area as hereinbefore disclosed. For example, the compounds in the below. which can be prepared by following similar procedure as described in above Schemes/Examples with suitable modifications known to the one ordinary skilled in the art are also included in the scope of the present invention.

TABLE 8

| Comp. No. | Structure |
|---|---|
| 22 | 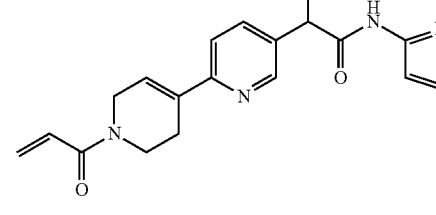 |
| 23 | 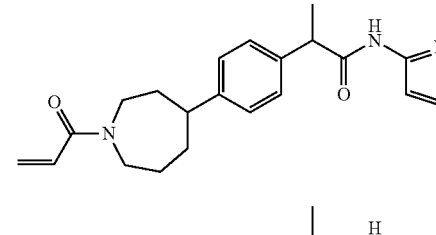 |
| 24 | 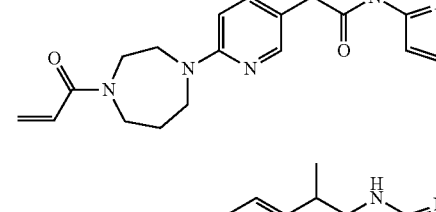 |
| 25 | 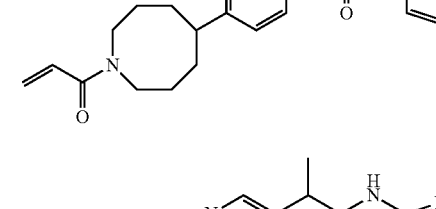 |
| 26 | 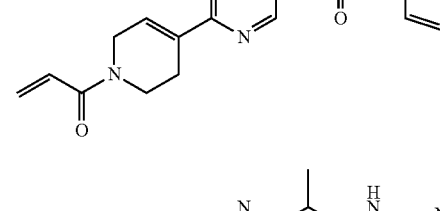 |
| 27 | 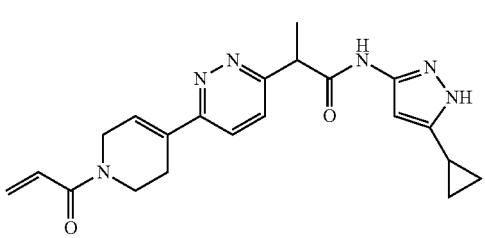 [SMILES: C=CC(=O)N1CC=C(c2ccc(C(C)C(=O)Nc3cc(C4CC4)[nH]n3)nn2)CC1] |
| 28 | 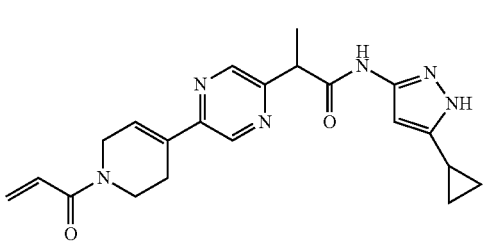 [SMILES: C=CC(=O)N1CC=C(c2cnc(C(C)C(=O)Nc3cc(C4CC4)[nH]n3)cn2)CC1] |

TABLE 8-continued

| Comp. No. | Structure |
|---|---|
| 30 | 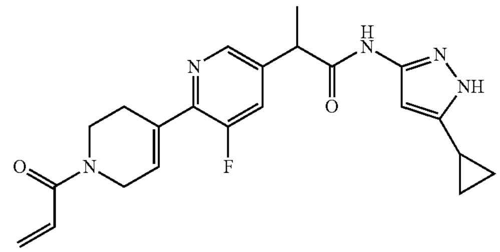 [SMILES: C=CC(=O)N1CC=C(c2ncc(C(C)C(=O)Nc3cc(C4CC4)[nH]n3)cc2F)CC1] |
| 31 | 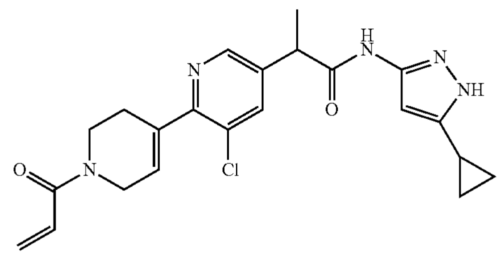 [SMILES: C=CC(=O)N1CC=C(c2ncc(C(C)C(=O)Nc3cc(C4CC4)[nH]n3)cc2Cl)CC1] |
| 32 | 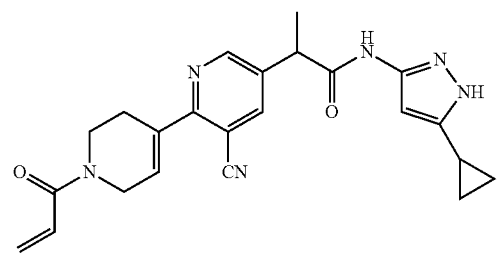 [SMILES: C=CC(=O)N1CC=C(c2ncc(C(C)C(=O)Nc3cc(C4CC4)[nH]n3)cc2C#N)CC1] |
| 33 | 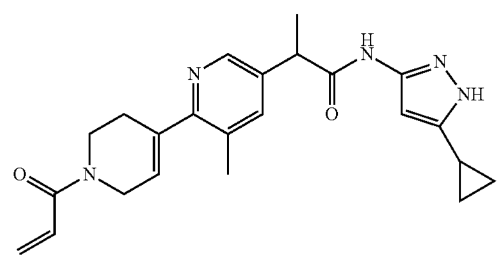 [SMILES: C=CC(=O)N1CC=C(c2ncc(C(C)C(=O)Nc3cc(C4CC4)[nH]n3)cc2C)CC1] |

Example 7

CDKs Assays

CDK12 Plate Based Target Engagement Assay:

Jurkat cells were treated with varying concentrations of the compound for 6 hours. The DMSO concentration was maintained at 0.1%. Cells were harvested and lysed. 200 μg of the lysate was incubated with 1 μM Bio-THZ531 in the presence of 1 mM DTT and incubated on a rocker at 4° C. overnight. 100 μL of this sample was added to pre-washed streptavidin coated plates and incubated at room temperature on a rocker for 2 hours. The plates were washed and incubated with CDK12 antibody for overnight at 4° C. Next day the plate was washed and incubated for 2 hours with HRP labelled anti rabbit secondary antibody. Bio-THZ531 bound CDK12 was determined using TMB substrate. The plates were read using the M3 spectrophotometer at 450 nM and 570 nM. Percentage CDK12 occupancy with the test compound was calculated over untreated control. Occupancy 50 was calculated by fitting the dose response data to sigmoidal curve fitting equation using GraphPad Prism software V5.

Jurkat Cell Proliferation Assay:

Jurkat cells were seeded in a 96-well round-bottom plate and treated with varying concentration of compound. The final DMSO concentration was maintained at 0.1%. Compounds were screened in a 9-point dose response format starting with 10 µM and ⅓$^{rd}$ serial dilution. At the end of 72 h, cells were spun down and media was aspirated. 50 µL of XTT containing media was added to the wells. The plates were read using the M3 spectrophotometer at 465 nM. $EC_{50}$ was calculated by fitting the dose response data to sigmoidal curve fitting equation using GraphPad Prism software V5.

Biochemical Assay for CDK12 (Kd Determination):

Kinase-tagged T7 phage strains were grown in parallel in 24-well blocks in an E. coli host derived from the BL21 strain. E. coli were grown to log-phase and infected with T7 phage from a frozen stock (multiplicity of infection=0.4) and incubated with shaking at 32° C. until lysis (90-150 minutes). The lysates were centrifuged (6,000xg) and filtered (0.2 µm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1x binding buffer (20% SeaBlock, 0.17xPBS, 0.05% Tween 20, 6 mM DTT). Test compounds were prepared as 40x stocks in 100% DMSO and directly diluted into the assay. All reactions were performed in polypropylene 384-well plates in a final volume of 0.02 ml. The assay plates were incubated at room temperature with shaking for 1 hour and the affinity beads were washed with wash buffer (1xPBS, 0.05% Tween 20). The beads were then re-suspended in elution buffer (1xPBS, 0.05% Tween 20, 0.5 µM non-biotinylated affinity ligand) and incubated at room temperature with shaking for 30 minutes. The kinase concentration in the eluates was measured by qPCR.

Biochemical Assay for CDK13:

LanthaScreen Eu Kinase Binding Assays are based on the binding and displacement of Alexa Fluor 647-labeled, ATP-competitive kinase inhibitor scaffold (kinase tracer) to the kinase of interest. Binding of the kinase tracer 236 (100 nM) to the CDK13 (5 nM) kinase is detected using a europium-labelled anti-GST tag antibody (2 nM), which binds to the kinase. Simultaneous binding of the tracer and antibody to the kinase results in a high degree of FRET (fluorescence resonance energy transfer) from the europium (Eu) donor fluorophore to the Alexa Fluor™ 647 acceptor fluorophore on the kinase tracer. Binding of an inhibitor to the kinase competes for binding with the tracer, resulting in a loss of FRET signal.

Biochemical Assay for CDK12 ($IC_{50}$ Determination):

The inhibitory activity of the test compounds was assessed by the LANCE TR-FRET assay, which detects the ATP-dependent phosphorylation of an ULight-4E-BP1 (Thr37/Thr46) substrate peptide (100 nM) by CDK12 (30 nM). Briefly, the enzyme reaction was run in reaction buffer (25 mM HEPES (pH 7.5), 10 mM MgCl2, 0.01% BSA, 0.01% Triton x, 1 mM DTT). The assay was performed in 384-well plate format. The end concentration of the ATP substrate was 100 µM, and that of the ULight-4E-BP1 (Thr37/Thr46) substrate peptide was 100 nM, and of CDK12 was 30 nM. Pre-incubation of the compound and enzyme was performed for 60 min at room temperature. After 60 min incubation at room temperature, the reaction was terminated by the addition of 40 mM EDTA and 0.5 nM Eu-labeled anti-phospho-eIF4E-binding protein (Thr37/46) antibody in LANCE detection buffer. Time-resolved fluorescence (excitation, 320 nm; emission donor, 615 nm; emission acceptor, 665 nm) was monitored by using 2030 multilabel reader Victor5 (PerkinElmer). The readout was calculated as (acceptor counts/donor counts)x1000. The $IC_{50}$ values were derived by fitting a sigmoidal dose-response curve to a plot of assay readout over inhibitor concentration. All fits were computed with the program Prism 5.03 (Graph Pad Software, San Diego, Calif.).

Biochemical Assay for CDK7:

The inhibitory activity of the test compounds was assessed by the LANCE TR-FRET assay, which detects the ATP-dependent phosphorylation of an ULight-myelin basic protein (MBP) substrate peptide (100 nM) by CDK7 (10 nM). Briefly, the enzyme reaction was run in reaction buffer (20 mM HEPES (pH 7.5), 10 mM MgCl2, 0.01% Triton x, 100 µM Sodium Orthovanadate, 1 mM DTT). The assay was performed in 384-well plate. The end concentration of the ATP substrate was 1 mM/100 µM, and that of the ULight-MBP substrate peptide was 100 nM, and of CDK7 was 10 nM. Pre-incubation of the compound and enzyme was performed for 60 min at room temperature. After 60 min incubation at room temperature, the reaction was terminated by the addition of 40 mM EDTA and 1 nM Eu-labeled anti-phospho-MBP-binding protein antibody in the buffer. Time-resolved fluorescence (excitation, 320 nm; emission donor, 615 nm; emission acceptor, 665 nm) was monitored by using 2030 multilabel reader Victor5 (PerkinElmer). The readout was calculated as (acceptor counts/donor counts)x 1000. The $IC_{50}$ values were derived by fitting a sigmoidal dose-response curve to a plot of assay readout over inhibitor concentration. All fits were computed with the program Prism 5.03 (Graph Pad Software, San Diego, Calif.).

Exemplary compounds of the present invention were screened by the above-mentioned assays and the results are tabulated; the Kd values of the selected compounds are set forth below in table-9 wherein "A" refers to a Kd value less than 0.025 µM, "B" refers to a Kd value in range of 0.025 µM to 0.1 µM and "C" refers to a Kd value greater than 0.1 µM.

TABLE 9

Kd values for CDK12 activity

| CDK12 Kd (µM) | Compound No. |
|---|---|
| A | 4, 6, 10, 12-16, 20-21, 34-35 and 37. |
| B | 1, 2, 5, 8, 9, 11, 18 and 36. |
| C | 3, 7, 17 and 19. |

Comparisons:

Compounds with greater selectivity are expected to provide a higher therapeutic index. The compounds of the present invention have better or substantially better selectivity for CDK12/13 vs. CDK7 and the comparison data is given in the below table-10.

TABLE 10

Comparison data between CDK12, CDK13 and CDK7

| Comp. No | CDK12 IC$_{50}$ µM | CDK13 IC$_{50}$ µM | CDK 7 IC$_{50}$ µM | Ratio CDK7/ CDK12 | Ratio CDK7/ CDK13 |
| --- | --- | --- | --- | --- | --- |
| 1 | 0.084 | 0.012 | 3.3 | 39.28 | 275.0 |
| 2 | 0.06 | 0.005 | 2.29 | 38.16 | 458.0 |
| 3 | NA | 0.101 | 0.506 | — | 5.0 |
| 4 | 0.072 | 0.003 | 1.71 | 23.75 | 570.0 |
| 5 | 1.309 | 0.077 | >10 | 7.64 | 129.87 |
| 6 | 0.04 | 0.006 | 1.30 | 32.5 | 216.66 |
| 7 | NA | 0.398 | 0.744 | — | 1.86 |
| 8 | 0.38 | 0.019 | NA | — | — |
| 9 | 0.24 | 0.021 | 6.585 | 27.43 | 313.57 |
| 10 | 0.74 | 0.018 | 5.492 | 7.42 | 305.11 |
| 11 | 1.019 | 0.045 | 3.646 | 3.57 | 81.02 |
| 12 | 0.151 | 0.007 | 2.83 | 18.74 | 404.28 |
| 13 | 0.058 | 0.028 | >10 | 172.41 | 357.14 |
| 14 | 0.895 | 0.072 | NA | — | — |
| 15 | 0.235 | 0.0188 | 0.621 | 2.64 | 33.03 |
| 16 | 0.646 | 0.035 | NA | — | — |
| 17 | 0.59 | 0.081 | 7.96 | 13.49 | 98.27 |
| 18 | 0.238 | 0.0117 | 2.322 | 9.75 | 198.46 |
| 19 | NA | 5.81 | NA | — | — |
| 20 | 0.099 | 0.094 | 2.09 | 21.11 | 22.23 |
| 21 | 0.235 | 0.073 | NA | — | — |
| 34 | 0.189 | 0.0043 | NA | — | — |
| 35 | 0.03 | 0.006 | 0.153 | 5.1 | 25.5 |
| 36 | 0.686 | 0.153 | NA | — | — |
| 37 | 0.029 | 0.003 | NA | — | — |
| 38 | 0.034 | 0.10 | 1.01 | 29.7 | 10.1 |
| 39 | 0.041 | 0.093 | NA | — | — |
| 40 | 0.16 | 0.279 | NA | — | — |
| 41 | 0.354 | 0.029 | 3.51 | 9.91 | 121.03 |
| 42 | 0.014 | 0.087 | 0.44 | 31.42 | 5.05 |
| 43 | 0.178 | 0.054 | NA | — | — |
| 44 | 0.009 | 0.0058 | 0.88 | 97.77 | 151.72 |
| 45 | 0.445 | 0.26 | 5.76 | 12.94 | 22.15 |
| 46 | 0.032 | 0.0069 | NA | — | — |
| 47 | 0.676 | 0.006 | NA | — | — |
| 48 | 0.055 | 0.006 | NA | — | — |
| 49 | 0.023 | 0.004 | 1.73 | 75.21 | 432.5 |
| 50 | NA | 0.007 | 0.012 | — | 1.71 |
| 51 | 0.203 | 0.025 | 1.692 | 8.33 | 67.68 |
| 52 | 0.227 | 0.019 | 2.19 | 9.64 | 115.26 |
| 53 | 0.01 | 0.0009 | 7.79 | 779 | 8655.55 |
| 54 | 0.094 | 0.003 | NA | — | — |
| 55 | 0.178 | NA | NA | — | — |
| 56 | 0.037 | 0.005 | NA | — | — |
| 57 | 0.140 | 0.01 | NA | — | — |
| 58 | 0.049 | 0.084 | NA | — | — |
| 59 | 0.040 | 0.019 | NA | — | — |
| 60 | 0.012 | NA | NA | — | — |
| 61 | 0.006 | NA | NA | — | — |
| 62 | 0.004 | NA | NA | — | — |

*NA—Not Available.

TABLE 11

Target Occupancy (Tocc$_{50}$) in Jurkat cells

| Compound No. | CDK12 Target Occupancy (Tocc$_{50}$) µM in Jurkat cells |
| --- | --- |
| 1 | 0.273 |
| 2 | 0.014 |
| 6 | 0.012 |
| 12 | 0.080 |
| 15 | 0.204 |
| 17 | 0.030 |
| 34 | 0.050 |
| 37 | 0.012 |
| 44 | 0.009 |
| 46 | 0.003 |
| 49 | 0.016 |
| 50 | 0.038 |
| 52 | 0.179 |
| 53 | 0.014 |
| 58 | 0.0097 |
| 59 | 0.025 |
| 60 | 0.0088 |
| 61 | 0.007 |

We claim:

1. A compound of formula (I):

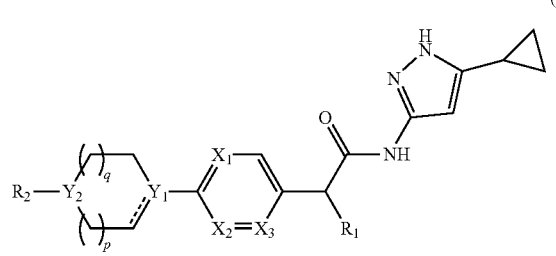

or a pharmaceutically acceptable salt, a N-oxide or a stereoisomer thereof;

wherein,

------ is an optional bond;

each $X_1$, $X_2$ and $X_3$ are independently $CR_3$ or N;

each $Y_1$ and $Y_2$ are independently C, CH or N;

$R_1$ is hydrogen or alkyl;

$R_2$ is

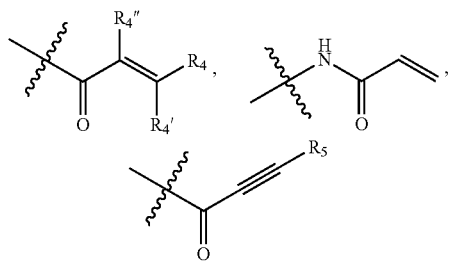

or —C≡N;

each $R_3$ is independently selected from hydrogen, halogen, cyano and alkyl;

$R_4$ is hydrogen, alkyl or —$(CH_2)_n$—$NR_aR_b$;

$R_4'$ & $R_4''$ are each independently hydrogen or alkyl;

$R_5$ is hydrogen or alkyl;

$R_a$ and $R_b$ are each independently hydrogen or alkyl; alternatively, $R_a$ and $R_b$ together with the nitrogen atom to which they are attached form an optionally substituted heterocyclic ring containing 0-2 additional heteroatoms independently selected from N, O and S;

n is 1 to 3; and p and q are each independently selected from 0 to 2.

2. The compound of claim 1, having a compound of formula (IA):

(IA)

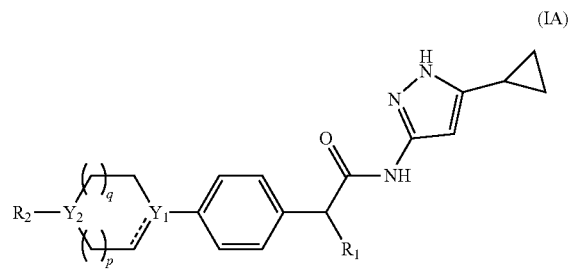

or a pharmaceutically acceptable salt or a stereoisomer thereof.

3. The compound of claim 1, having a compound of formula (IB):

(IB)

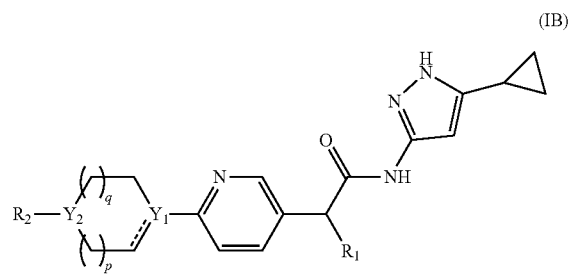

or a pharmaceutically acceptable salt, a N-oxide or a stereoisomer thereof.

4. The compound of claim 1, having a compound of formula (IC):

(IC)

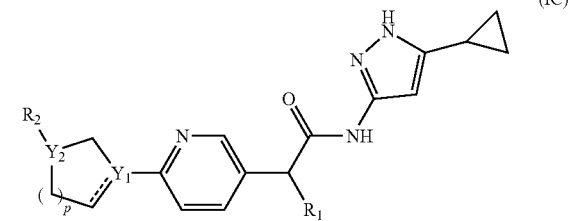

or a pharmaceutically acceptable salt, a N-oxide or a stereoisomer thereof.

5. The compound of claim 1, having compounds of formula (ID) to (IG), (IJ) and (IK):

(ID)

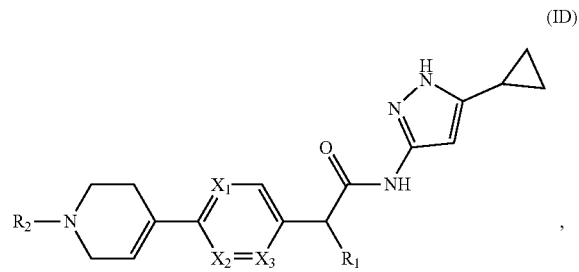

, (IE)

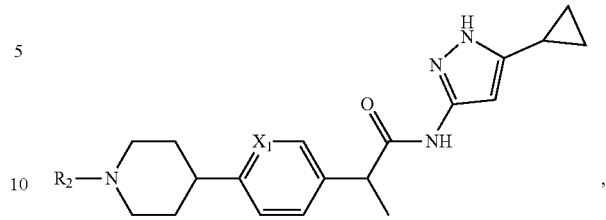

, (IF)

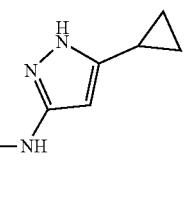

, (IG)

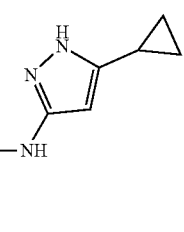

, (IJ)

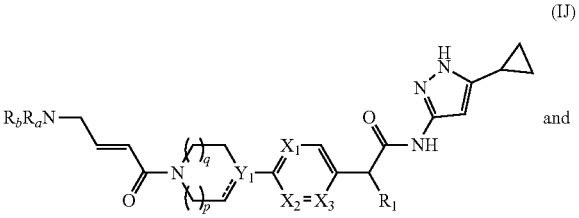 and (IK)

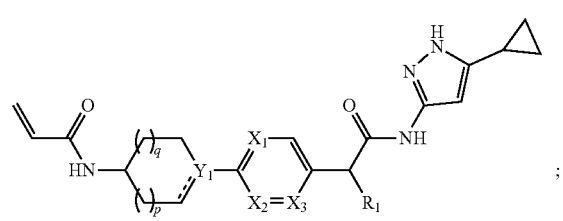 ;

or a pharmaceutically acceptable salt, a N-oxide or a stereoisomer thereof.

6. The compound of claim 1, having a compound of formula (IH):

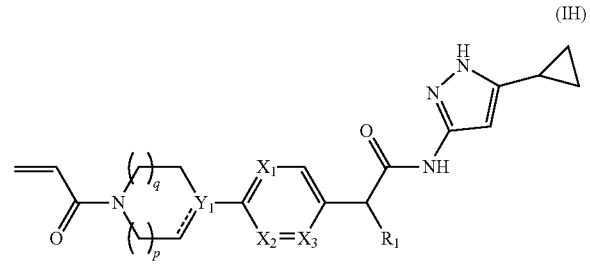

(IH)

or a pharmaceutically acceptable salt, a N-oxide or a stereoisomer thereof.

7. The compound of claim 1, having a compound of formula (IL):

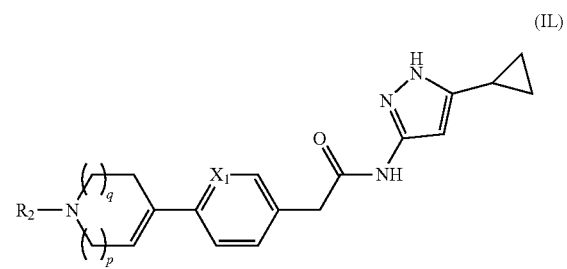

(IL)

or a pharmaceutically acceptable salt, a N-oxide or a stereoisomer thereof.

8. The compound of claim 1, having a compound of formula (IM):

(IM)

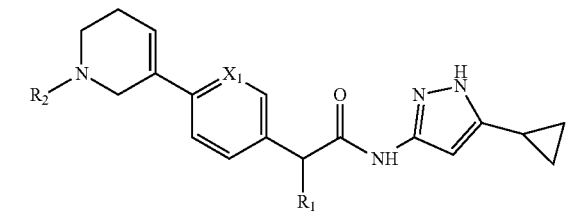

or a pharmaceutically acceptable salt, a N-oxide or a stereoisomer thereof.

9. The compound of claim 1, wherein, ring

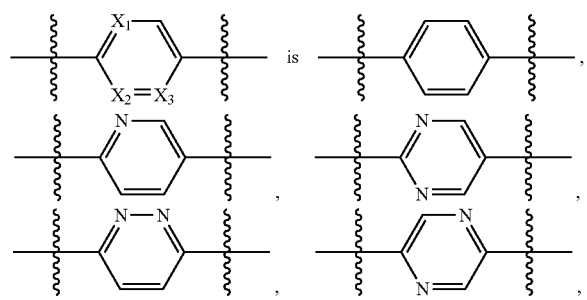

is

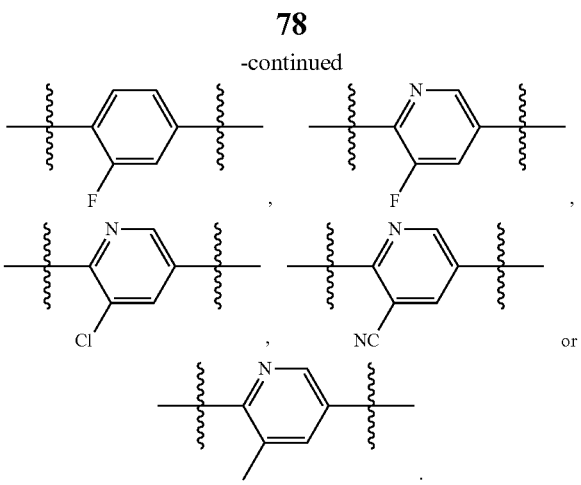

10. The compound of claim 1, wherein, ring

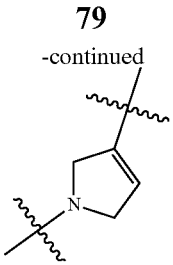

11. The compound of claim 1, wherein $R_1$ is hydrogen.

12. The compound of claim 1, wherein,

------ is a bond;

$X_1$ is N; $X_2$ and $X_3$ are each $CR_3$;

$Y_1$ is C; $Y_2$ is N;

$R_1$ is hydrogen;

$R_2$ is

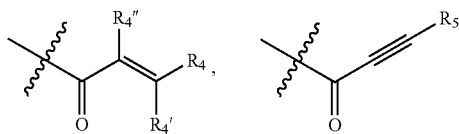

or —C≡N, each $R_3$ independently is hydrogen or halogen; and $R_4$, $R_4'$, $R_4''$ and $R_5$ are each independently hydrogen or alkyl.

13. The compound of claim 1, wherein, $R_1$ is alkyl; the said alkyl is methyl, ethyl or isopropyl.

14. The compound of claim 1, wherein, ring

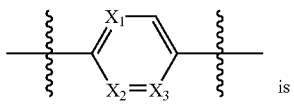 is

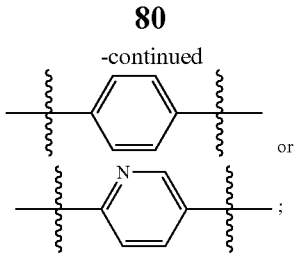

ring

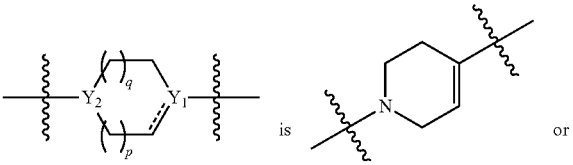

is

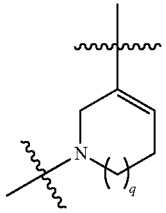 or $R_1$ is hydrogen or methyl;

$R_2$ is and $R_4$ is hydrogen.

15. The compound of claim 1 selected from:

| Comp. No. | IUPAC Name |
|---|---|
| 1 | 2-(4-(1-acryloyl-1,2,3,6-tetrahydropyridin-4-yl)phenyl)-N-(5-cyclopropyl-1H-pyrazol-3-yl)propanamide; |
| 2 | (S)-2-(4-(1-acryloyl-1,2,3,6-tetrahydropyridin-4-yl)phenyl)-N-(5-cyclopropyl-1H-pyrazol-3-yl)propanamide; |
| 3 | 2-(4-(1-acryloyl-1,2,3,6-tetrahydropyridin-4-yl)phenyl)-N-(5-cyclopropyl-1H-pyrazol-3-yl)-3-methylbutanamide; |
| 4 | 2-(1'-acryloyl-1',2',3',6'-tetrahydro-[2,4'-bipyridin]-5-yl)-N-(5-cyclopropyl-1H-pyrazol-3-yl)propanamide; |
| 5 | 2-(1'-acryloyl-1',2',3',6'-tetrahydro-[2,4'-bipyridin]-5-yl)-N-(5-cyclopropyl-1H-pyrazol-3-yl)propanamide (Isomer-1 of compound-4); |
| 6 | 2-(1'-acryloyl-1',2',3',6'-tetrahydro-[2,4'-bipyridin]-5-yl)-N-(5-cyclopropyl-1H-pyrazol-3-yl)propanamide (Isomer-2 of compound-4); |
| 7 | 2-(1'-acryloyl-1',2',3',6'-tetrahydro-[2,4'-bipyridin]-5-yl)-N-(5-cyclopropyl-1H-pyrazol-3-yl)-3-methylbutanamide; |
| 8 | N-(4'-(1-((5-cyclopropyl-1H-pyrazol-3-yl)amino)-1-oxopropan-2-yl)-2,3,4,5-tetrahydro-[1,1'-biphenyl]-4-yl)acrylamide; |
| 9 | 2-(4-(1-acryloyl-2,3,6,7-tetrahydro-1H-azepin-4-yl)phenyl)-N-(5-cyclopropyl-1H-pyrazol-3-yl)propanamide; |
| 10 | N-(4-(4-(1-((5-cyclopropyl-1H-pyrazol-3-yl)amino)-1-oxopropan-2-yl)phenyl)cyclohexyl)acrylamide (Isomer-1); |
| 11 | N-(4-(4-(1-((5-cyclopropyl-1H-pyrazol-3-yl)amino)-1-oxopropan-2-yl)phenyl)cyclohexyl)acrylamide (Isomer-2); |
| 12 | (S)-2-(4-(1-acryloylpiperidin-4-yl)phenyl)-N-(5-cyclopropyl-1H-pyrazol-3-yl)propanamide; |

-continued

| Comp. No. | IUPAC Name |
|---|---|
| 13 | 2-(6-(1-acryloylpiperidin-4-yl)pyridin-3-yl)-N-(5-cyclopropyl-1H-pyrazol-3-yl)propanamide; |
| 14 | (S,E)-N-(5-cyclopropyl-1H-pyrazol-3-yl)-2-(4-(1-(4-(diethylamino)but-2-enoyl)-1,2,3,6-tetrahydropyridin-4-yl)phenyl)propanamide; |
| 15 | (S,E)-N-(5-cyclopropyl-1H-pyrazol-3-yl)-2-(4-(1-(4-(dimethylamino)but-2-enoyl)-1,2,3,6-tetrahydropyridin-4-yl)phenyl)propanamide; |
| 16 | (S,E)-N-(5-cyclopropyl-1H-pyrazol-3-yl)-2-(4-(1-(4-morpholinobut-2-enoyl)-1,2,3,6-tetrahydropyridin-4-yl)phenyl)propanamide; |
| 17 | 2-(4-(4-acryloylpiperazin-1-yl)phenyl)-N-(5-cyclopropyl-1H-pyrazol-3-yl)propanamide; |
| 18 | 2-(4-(4-acryloylpiperazin-1-yl)phenyl)-N-(5-cyclopropyl-1H-pyrazol-3-yl)propanamide (Isomer-1 of compound-17); |
| 19 | 2-(4-(4-acryloylpiperazin-1-yl)phenyl)-N-(5-cyclopropyl-1H-pyrazol-3-yl)propanamide (Isomer-2 of compound-17); |
| 20 | 2-(6-(4-acryloylpiperazin-1-yl)pyridin-3-yl)-N-(5-cyclopropyl-1H-pyrazol-3-yl)propanamide; |
| 21 | N-(1-(4-(1-((5-cyclopropyl-1H-pyrazol-3-yl)amino)-1-oxopropan-2-yl)phenyl)piperidin-4-yl)acrylamide; |
| 22 | 2-(1'-acryloyl-1',2',3',6'-tetrahydro-[2,4'-bipyridin]-5-yl)-N-(5-cyclopropyl-1H-pyrazol-3-yl)butanamide; |
| 23 | 2-(4-(1-acryloylazepan-4-yl)phenyl)-N-(5-cyclopropyl-1H-pyrazol-3-yl)propanamide; |
| 24 | 2-(6-(4-acryloyl-1,4-diazepan-1-yl)pyridin-3-yl)-N-(5-cyclopropyl-1H-pyrazol-3-yl)propanamide; |
| 25 | 2-(4-(1-acryloylazocan-5-yl)phenyl)-N-(5-cyclopropyl-1H-pyrazol-3-yl)propanamide; |
| 26 | 2-(2-(1-acryloyl-1,2,3,6-tetrahydropyridin-4-yl)pyrimidin-5-yl)-N-(5-cyclopropyl-1H-pyrazol-3-yl)propanamide; |
| 27 | 2-(6-(1-acryloyl-1,2,3,6-tetrahydropyridin-4-yl)pyridazin-3-yl)-N-(5-cyclopropyl-1H-pyrazol-3-yl)propanamide; |
| 28 | 2-(5-(1-acryloyl-1,2,3,6-tetrahydropyridin-4-yl)pyrazin-2-yl)-N-(5-cyclopropyl-1H-pyrazol-3-yl)propanamide; |
| 29 | 2-(4-(1-acryloyl-1,2,3,6-tetrahydropyridin-4-yl)-3-fluorophenyl)-N-(5-cyclopropyl-1H-pyrazol-3-yl)propanamide; |
| 30 | 2-(1'-acryloyl-3-fluoro-1',2',3',6'-tetrahydro-[2,4'-bipyridin]-5-yl)-N-(5-cyclopropyl-1H-pyrazol-3-yl)propanamide; |
| 31 | 2-(1'-acryloyl-3-chloro-1',2',3',6'-tetrahydro-[2,4'-bipyridin]-5-yl)-N-(5-cyclopropyl-1H-pyrazol-3-yl)propanamide; |
| 32 | 2-(1'-acryloyl-3-cyano-1',2',3',6'-tetrahydro-[2,4'-bipyridin]-5-yl)-N-(5-cyclopropyl-1H-pyrazol-3-yl)propanamide; |
| 33 | 2-(1'-acryloyl-3-methyl-1',2',3',6'-tetrahydro-[2,4'-bipyridin]-5-yl)-N-(5-cyclopropyl-1H-pyrazol-3-yl)propanamide; |
| 34 | (S)-2-(4-(1-acryloyl-1,2,5,6-tetrahydropyridin-3-yl)phenyl)-N-(5-cyclopropyl-1H-pyrazol-3-yl)propanamide; |
| 35 | 2-(1'-acryloyl-1',2',5',6'-tetrahydro-[2,3'-bipyridin]-5-yl)-N-(5-cyclopropyl-1H-pyrazol-3-yl)propanamide; |
| 36 | 2-(1'-acryloyl-1',2',5',6'-tetrahydro-[2,3'-bipyridin]-5-yl)-N-(5-cyclopropyl-1H-pyrazol-3-yl)propanamide (Isomer-1 of compound-35); |
| 37 | 2-(1'-acryloyl-1',2',5',6'-tetrahydro-[2,3'-bipyridin]-5-yl)-N-(5-cyclopropyl-1H-pyrazol-3-yl)propanamide (Isomer-2 of compound-35); |
| 38 | 2-(6-(1-acryloyl-2,5-dihydro-1H-pyrrol-3-yl)pyridin-3-yl)-N-(5-cyclopropyl-1H-pyrazol-3-yl)propanamide; |
| 39 | 2-(1'-acryloyl-1',2',5',6'-tetrahydro-[2,3'-bipyridin]-5-yl)-N-(5-cyclopropyl-1H-pyrazol-3-yl)butanamide; |
| 40 | 2-(4-(1-acryloyl-1,2,5,6-tetrahydropyridin-3-yl)phenyl)-N-(5-cyclopropyl-1H-pyrazol-3-yl)-3-methylbutanamide; |
| 41 | 2-(6-(1-acryloylpiperidin-3-yl)pyridin-3-yl)-N-(5-cyclopropyl-1H-pyrazol-3-yl)propanamide; |
| 42 | 2-(4-(1-acryloyl-1,2,5,6-tetrahydropyridin-3-yl)-3-fluorophenyl)-N-(5-cyclopropyl-1H-pyrazol-3-yl)propanamide; |
| 43 | 2-(1'-acryloyl-1',2',5',6'-tetrahydro-[2,3'-bipyridin]-5-yl)-N-(5-cyclopropyl-1H-pyrazol-3-yl)-3-methylbutanamide; |
| 44 | 2-(4-(1-acryloyl-1,2,3,6-tetrahydropyridin-4-yl)-3-fluorophenyl)-N-(5-cyclopropyl-1H-pyrazol-3-yl)propanamide; |
| 45 | 2-(4-(1-acryloyl-1,2,3,6-tetrahydropyridin-4-yl)-3-fluorophenyl)-N-(5-cyclopropyl-1H-pyrazol-3-yl)propanamide; |
| 46 | 2-(6-(1-acryloyl-2,5-dihydro-1H-pyrrol-3-yl)pyridin-3-yl)-N-(5-cyclopropyl-1H-pyrazol-3-yl)propanamide; |
| 47 | 2-(6-(1-acryloyl-2,5-dihydro-1H-pyrrol-3-yl)pyridin-3-yl)-N-(5-cyclopropyl-1H-pyrazol-3-yl)propanamide; |
| 48 | 2-(6-(1-acryloylpyrrolidin-3-yl)pyridin-3-yl)-N-(5-cyclopropyl-1H-pyrazol-3-yl)propanamide; |
| 49 | 2-(1'-acryloyl-1',2',5',6'-tetrahydro-[2,3'-bipyridin]-5-yl)-N-(5-cyclopropyl-1H-pyrazol-3-yl)acetamide; |
| 50 | N-(5-cyclopropyl-1H-pyrazol-3-yl)-2-(1'-propioloyl-1',2',3',6'-tetrahydro-[2,4'-bipyridin]-5-yl)propanamide; |

| Comp. No. | IUPAC Name |
|---|---|
| 51 | 2-(1'-(but-2-ynoyl)-1',2',3',6'-tetrahydro-[2,4'-bipyridin]-5-yl)-N-(5-cyclopropyl-1H-pyrazol-3-yl)propanamide; |
| 52 | 2-(1'-(but-2-ynoyl)-1',2',5',6'-tetrahydro-[2,3'-bipyridin]-5-yl)-N-(5-cyclopropyl-1H-pyrazol-3-yl)propanamide; |
| 53 | 2-(6-(1-acryloyl-2,5-dihydro-1H-pyrrol-3-yl)pyridin-3-yl)-N-(5-cyclopropyl-1H-pyrazol-3-yl)acetamide; |
| 54 | (E)-2-(1'-(but-2-enoyl)-1',2',5',6'-tetrahydro-[2,3'-bipyridin]-5-yl)-N-(5-cyclopropyl-1H-pyrazol-3-yl)acetamide; |
| 55 | N-(5-cyclopropyl-1H-pyrazol-3-yl)-2-(1'-(3-methylbut-2-enoyl)-1',2',5',6'-tetrahydro-[2,3'-bipyridin]-5-yl)acetamide; |
| 56 | 2-(1'-(but-2-ynoyl)-1',2',5',6'-tetrahydro-[2,3'-bipyridin]-5-yl)-N-(5-cyclopropyl-1H-pyrazol-3-yl)acetamide; |
| 57 | N-(5-cyclopropyl-1H-pyrazol-3-yl)-2-(1'-methacryloyl-1',2', 5',6'-tetrahydro-[2,3'-bipyridin]-5-yl)acetamide; |
| 58 | N-(5-cyclopropyl-1H-pyrazol-3-yl)-2-(1'-propioloyl-1',2',5',6'-tetrahydro-[2,3'-bipyridin]-5-yl)acetamide; |
| 59 | 2-(1'-acryloyl-1',2',3',6'-tetrahydro-[2,4'-bipyridin]-5-yl)-N-(5-cyclopropyl-1H-pyrazol-3-yl)acetamide; |
| 60 | N-(5-cyclopropyl-1H-pyrazol-3-yl)-2-(6-(1-propioloyl-2,5-dihydro-1H-pyrrol-3-yl)pyridin-3-yl)acetamide; |
| 61 | 2-(1'-cyano-1',2',5',6'-tetrahydro-[2,3'-bipyridin]-5-yl)-N-(5-cyclopropyl-1H-pyrazol-3-yl)acetamide; and |
| 62 | 2-(1'-cyano-1',2',3',6'-tetrahydro-[2,4'-bipyridin]-5-yl)-N-(5-cyclopropyl-1H-pyrazol-3-yl)acetamide; | or a pharmaceutically acceptable salt, a N-oxide or a stereoisomer thereof.

16. A pharmaceutical composition comprising a compound of claim 1, or a pharmaceutically acceptable salt or a stereoisomer thereof and at least one pharmaceutically acceptable carrier or excipient.

17. A method of treating a subject suffering from a disease or condition associated with aberrant activity of CDK12/13, comprising administering to the subject the pharmaceutical composition of claim 16.

18. A method of inhibiting CDK12/13 in a subject, comprising administering to the subject a compound of claim 1.

19. A method of treating diseases and/or disorder or condition mediated by CDK12/13 in a subject comprising administering a therapeutically effective amount of a compound of claim 1.

20. The method of claim 19, wherein the CDK12/13 mediated disorder or disease or condition is selected from the group consisting of a cancer, an inflammatory disorder, an auto-inflammatory disorder and an infectious disease.

21. The method of claim 20, wherein the CDK12/13 mediated disorder or disease or condition is cancer.

22. The method of claim 21, wherein the cancer is selected from the group consisting of breast cancer, liver cancer, colon cancer, kidney cancer, bladder cancer, small cell lung cancer, non-small cell lung cancer, head and neck cancer, thyroid cancer, esophagus cancer, stomach cancer, pancreatic cancer, ovarian cancer, gall bladder cancer, cervical cancer, prostate cancer, squamous cell carcinoma, leukemia, acute lymphoblastic leukemia, acute lymphocytic leukemia, Hodgkins lymphoma, non-Hodgkins lymphoma, B-cell lymphoma, T-cell lymphoma, hairy cell lymphoma, myeloma, mantle cell lymphoma, Burkett's lymphoma, acute and chronic myelogenous leukemias, myelodysplastic syndrome, promyelocytic leukemia, fibrosarcoma, rhabdomyosarcoma, tumors of the central and peripheral nervous system, including astrocytoma, neuroblastoma, glioma, schwannomas, seminoma, melanoma, osteosarcoma, teratocarcinoma, keratoacanthoma, xenoderoma pigmentosum, thyroid follicular cancer and Kaposi's sarcoma.

23. The method of claim 19, wherein the disorder or condition mediated by CDK12/13 is Myotonic Dystrophy type 1, Myotonic Dystrophy type 2, Fragile X associated tremor/ataxia syndrome, amylotrophic lateral sclerosis (ALS) and frontotemporal dementia, Huntington's Disease like 2, Huntington's Disease, several types of Spinocerebellar Ataxia, Dentatorubral-pallidoluysian atrophy and Spinal and Bulbar Muscular Atrophy.

24. The method of claim 19, comprising an additional step of administering to the subject in need thereof one or more additional chemotherapeutic agents independently selected from anti-proliferative agents, anti-cancer agents, immunosuppressant agents and pain-relieving agents.

25. The method of claim 19, wherein the subject is a human or other mammal.

* * * * *